United States Patent
Moller et al.

(10) Patent No.: US 9,375,482 B2
(45) Date of Patent: *Jun. 28, 2016

(54) POLYLACTIDE COMPOSITIONS AND USES THEREOF

(71) Applicant: UNIVERSITY OF GENEVA, Geneva (CH)

(72) Inventors: Michael Moller, Geneva (CH); Thomas Trimaille, Marseilles (FR); Robert Gurny, Geneva (CH)

(73) Assignee: University of Geneva, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/258,357

(22) Filed: Apr. 22, 2014

(65) Prior Publication Data

US 2015/0073060 A1 Mar. 12, 2015

Related U.S. Application Data

(60) Division of application No. 13/778,038, filed on Feb. 26, 2013, now Pat. No. 8,741,877, which is a continuation of application No. 11/912,102, filed as application No. PCT/IB2006/002849 on Apr. 21, 2006, now Pat. No. 8,466,133.

(60) Provisional application No. 60/750,141, filed on Dec. 14, 2005, provisional application No. 60/674,103, filed on Apr. 22, 2005.

(51) Int. Cl.

| | |
|---|---|
| *A01N 37/18* | (2006.01) |
| *A61K 31/65* | (2006.01) |
| *A61K 47/34* | (2006.01) |
| *A61K 9/00* | (2006.01) |
| *A61K 9/107* | (2006.01) |
| *C08G 63/08* | (2006.01) |
| *C08G 63/82* | (2006.01) |

(52) U.S. Cl.
CPC .............. *A61K 47/34* (2013.01); *A61K 9/0024* (2013.01); *A61K 9/1075* (2013.01); *C08G 63/08* (2013.01); *C08G 63/823* (2013.01)

(58) Field of Classification Search
CPC ... A61K 47/34; A61K 9/0024; A61K 9/1075; C08G 63/08; C08G 63/823
See application file for complete search history.

(56) References Cited

U.S. PATENT DOCUMENTS

| | | | |
|---|---|---|---|
| 5,410,016 A | 4/1995 | Hubbell et al. | |
| 5,434,241 A | 7/1995 | Kim et al. | |
| 5,686,630 A | 11/1997 | Miao et al. | |
| 5,858,746 A | 1/1999 | Hubbell et al. | |
| 6,007,845 A | 12/1999 | Domb et al. | |
| 6,126,919 A | 10/2000 | Stefely et al. | |
| 6,469,133 B2 | 10/2002 | Baker et al. | |
| 2003/0099709 A1* | 5/2003 | Shah | A61K 9/06 424/469 |

FOREIGN PATENT DOCUMENTS

| | | |
|---|---|---|
| JP | S53-145905 | 9/1978 |
| JP | H05-295120 | 11/1993 |
| WO | WO 2004/014453 | 2/2004 |
| WO | WO 2004/028583 | 4/2004 |

OTHER PUBLICATIONS

"Novel Functionalized Poly (lactides) for Drug Delivery," (Apr. 3, 2005) retrieved Apr. 11, 2008 from http://www.unige.ch/sciences/pharm/fagal/Anglais/projet5_EN.htm.
Chrisholm and Delbridge, "A study of the ring-opening of lactides and related cyclic esters bu Ph(2)SnX(2) and Ph(3)SnX compounds (X=NMe(2), OR)," *J. Chem.*, 27:1167-1176, 2003.
Dechy-Cabaret et al., "Controlled ring-opening polymerization of lactide and glycolide," *Chem. Rev.*, 104:6147-6176, 2004.
Degée et al., "Beneficial effect of triphenylphosphine on the bulk polymerization of L,L-lactide promoted by 2-ethylhexanoic acid tin (II) salt," *J. Polym. Sci. A. Polym. Chem.*, 37:2413-2420, 1999.
Drumright et al., "Polylactic acid technology," *Advanced Materials*, 12:1941-1946, 2000.
Edlund and Albertsson, "Degradable polymer microspheres for controlled drug delivery," *Advances in Polymer Science*, vol. 157:67-112, 2002.
Jamshidi et al., "Thermal characterization of polylactides," *Polymer*, 29:2229-2234, 1988.
Kowalski et al., "Kinetics and mechanism of cyclic esters polymerization initiated with tin (II) octoate, 1," *Macromol. Rapid Commun.*, 19:567-572, 1998.
Kricheldorf et al., "Polyactones 48. SnOct(2)-initiated polymerizations of lactide: a mechanistic study," *Macrromolcules*, 33:702-709, 2000.
Kricheldorf et al., "Polylactones: 31. Sn(II)octoate-initiated polymerization of L-lactide: a mechanistic study," *Polymer.*, 36:1253-1259, 1995.
Lin et al., "Stability and release performance of a series of pegylated copolymeric micelles," *Pharm Res.*, 20:668-673, 2003.
Liu and Ma, "Polymeric scaffolds for bone tissue engineering," *Ann. Biomed. Eng.*, 32:477-486, 2004.
Lou et al., "Novel aliphatic polyesters based on functional cyclic (Di)esters," *Macromol. Rapid. Commun.*, 24:161-172, 2003.
Möller et al., Stannous(II) trifluoromethane sulfonate: a versatile catalyst for the controlled ring-opening polymerization of lactides: formation of stereoregular surfaces from polylactide "brushes," *J. Poly. Sci. A. Polym. Chem.*, 39:3529-3538, 2001.

(Continued)

*Primary Examiner* — Wu-Cheng Winston Shen
*Assistant Examiner* — Jean Cornet
(74) *Attorney, Agent, or Firm* — Parker Highlander PLLC

(57) ABSTRACT

The present invention provides compositions and methods relating to polylactides which may be used for drug delivery (e.g., parenteral delivery), wherein an organic solvent is not required.

31 Claims, 11 Drawing Sheets

(56) References Cited

OTHER PUBLICATIONS

Mu and Feng, "A novel controlled release formulation for the anticancer drug paclitaxel (Taxol): PLGA nanoparticles containing vitamin E TPGS," *J. Control. Release*, 86:33-48, 2003.

Nederberg et al., "New paradigms for organic catalysts: the first organocatalytic living polymerization," *Chem. Int. Ed.*, 40:2712-2715, 2001.

Office Communication issued in Canadian Patent Application No. 2,605,652, dated May 7, 2012.

Office Communication issued in Canadian Patent Application No. 2,605,652, dated Jan. 10, 2013.

Office Communication issued in Canadian Patent Application No. 2,605,652, dated Aug. 26, 2013.

Office Communication issued in Japanese Patent Application No. 2008-507201, dated Sep. 12, 2012.

Office Communication issued in Japanese Patent Application No. 2008-507201, dated Jul. 29, 2013.

Office Communication issued in Japanese Patent Application No. 2008-507201, dated Jan. 29, 2014.

Office Communication issued in U.S. Appl. No. 11/912,102, dated Aug. 23, 2012.

Office Communication issued in U.S. Appl. No. 11/912,102, dated Jan. 30, 2012.

Office Communication issued in U.S. Appl. No. 11/912,102, dated Oct. 21, 2011.

Office Communication issued in U.S. Appl. No. 11/912,102, dated Jun. 21, 2011.

Office Communication issued in U.S. Appl. No. 13/778,038, dated Oct. 22, 2013.

PCT International Preliminary Report on Patentability issued in International Application No. PCT/IB2006/002849, issued Jul. 20, 2007.

PCT International Search Report and Written Opinion, issued in International Application No. PCT/IB2006/002849, dated Feb. 22, 2007.

Penning et al., "Preparation and properties of absorbable fibres from L-lactide copolymers," *Polymer*, 34:942-951, 1993.

Ryner et al., "L-lactide macromonomer synthesis initiated by new cyclic tin alkoxides functiUGENonalized for brushlike structures," *Macromolecules*, 34:7281-7287, 2001.

Schwach et al., "More about the polymerization of lactides in the presence of stannous octoate," *J. Polym. Sci. A. Polym. Chem.*, 35:3431-3440, 1997.

Schwach-Abdellaoui et al., "Hydrolysis and erosion studies of autocatalyzed poly(ortho esters) containing lactoyl-lactyl acid dimers," *Macromolecules*, 32:301-307, 1999.

Simmons and Baker, "Poly(phenyllactide): synthesis, characterization, and hydrolytic degradation," *Biomacromolecules*, 2:658-663, 2001.

Simmons et al., "Polymerization of phenyllactide," *Papers Presented at the Meeting—American Chemical Society*, 40(2):928, 1999.

Trimaille et al., "Novel polymeric micelles for hydrophobic drug delivery based on biodegradable poly(hexyl-substituted lactides)," *International Journal of Pharmaceutics*, 319(1-2):147-157, 2006.

Trimaille et al., "Synthesis and Properties of Novel Poly(Hexyl-Substituted Lactides) for Pharmaceutical Applications," *Chimia*, 59:348-352, 2005.

Trimaille et al., "Synthesis and ring-opening polymerization of new monoalkyl-substituted lactides," *J. Polym. Sci. A. Polym. Chem.*, 42:4379-4391, 2004.

Uhrich et al., "Polymeric systems for controlled drug release," *Chem. Rev.*, 99:3181-3198, 1999.

Vert et al., "Bioresorable plastic materials for bone surgery," *Macromolecular Biomaterials*, Hastings et al. (Eds.), CRS Press, F1, 119-142, 1984.

Vink et al., "Applications of life cycle assessment to NatureWorks™ polylactide (PLA) production," *Polym. Deg. Stab.*, 80:403-419, 2003.

Ye et al., "In vitro degradation of pol(caprolactone), poly(lactide) and their block copolymers: influence of composition, temperature and morphology," *React. Funct. Polym.*, 32:161-168, 1997.

Yin and Baker, "Preparation and characterization of substituted polylactides," *Macromolecules*, 32:7711-7718, 1999.

Office Communication issued in Japanese Patent Application No. 2013-243625, dated Nov. 19, 2015. (English translation of Japanese text).

Merkli et al., "Semi-solid hydrophobic bioerodible poly(ortho ester) for potential application in glaucoma filtering surgery," *J. Control. Release*, 29(2):105-112, 1994.

Office Communication issued in Japanese Patent Application No. 2014-207007, dated Sep. 17, 2015. (English translation of Japanese text).

Schwach-Abdellaoui et al., "Optimization of a novel bioerodible device based on auto-catalyzed poly(ortho esters) for controlled delivery of tetracycline to periodontal pocket ," *Biomaterials*, 22(12):1659-1666, 2001.

* cited by examiner

FIG. 6C
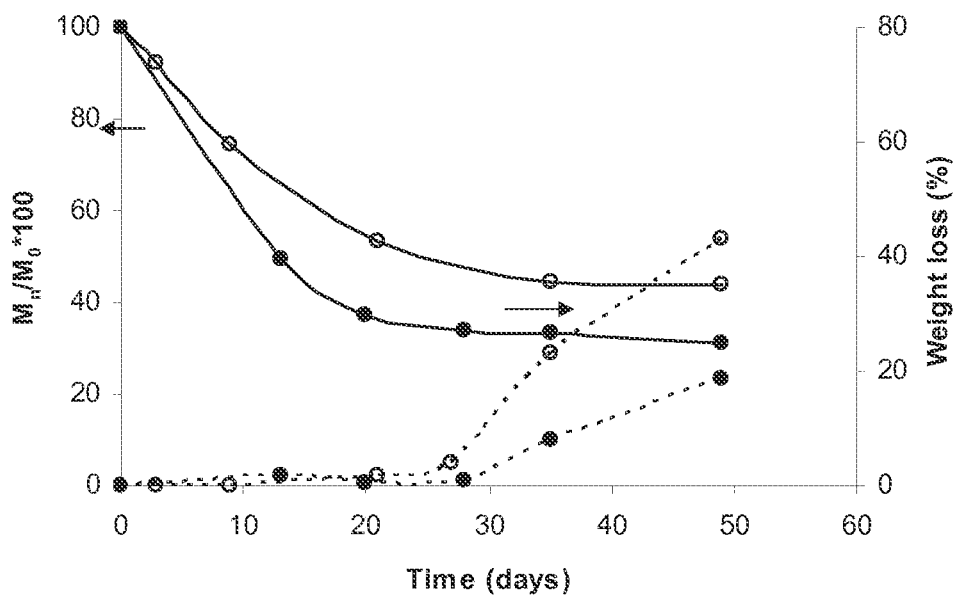
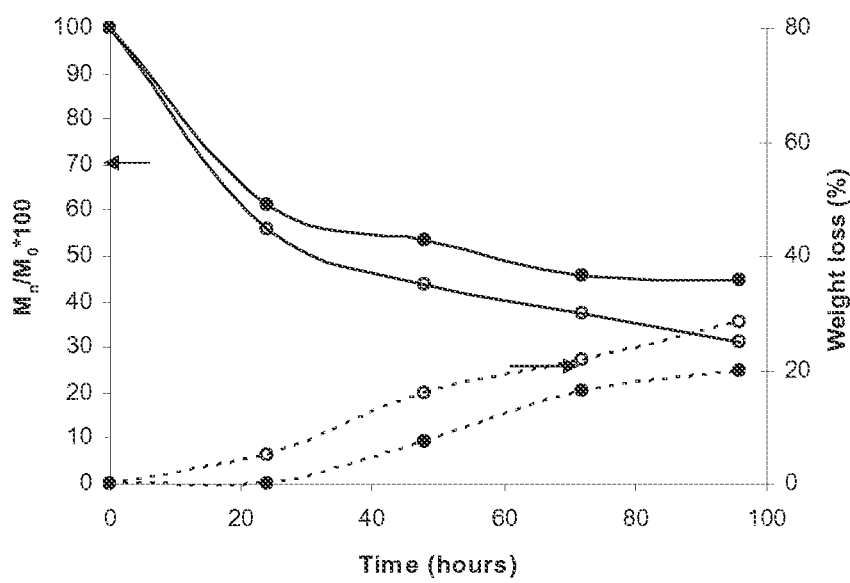
FIG. 7

POLYLACTIDE COMPOSITIONS AND USES THEREOF

This application is a divisional of U.S. patent application Ser. No. 13/778,038, filed Feb. 26, 2013, now U.S. Pat. No. 8,741,877, which is a continuation of U.S. patent application Ser. No. 11/912,102, filed Apr. 23, 2008, now U.S. Pat. No. 8,466,133, which is a national phase application under 35 U.S.C. §371 of International Application No. PCT/IB2006/002849, filed Apr. 21, 2006, which claims the benefit of U.S. Provisional Application Ser. No. 60/674,103 filed Apr. 22, 2005 and U.S. Provisional Application Ser. No. 60/750,141 filed Dec. 14, 2005, the entire contents and disclosures of which are specifically incorporated by reference herein without disclaimer.

BACKGROUND OF THE INVENTION

1. Field of the Invention

The present invention relates generally to the fields of pharmaceutics and drug delivery. More particularly, it concerns alkyl substituted polylactides which may be used to deliver a drug without the need for an organic solvent.

2. Description of Related Art

Biocompatible and biodegradable polylactides/glycolides (PLA/PLGA) have received high attention over the last thirty years in the biomedical field as sutures, implants, colloidal drug delivery systems (Penning et al., 1993; Uhrich et al., 1999), and more recently also in tissue repairing and engineering (Liu and Ma, 2004; Stock and Mayer, 2001) and anti-cancer drug delivery (Mu and Feng, 2003; Jiang et al., 2005). Next to the medical field they are also widely used in the packaging area. As biodegradable "green polymers" they are preferable to the commodity polymers currently used (Drumright et al., 2000; Vink et al., 2003).

There is a crucial need of well-defined polylactide-based materials with advanced properties to fit all the requirements for the different applications. For example, PLA/PLGA homo- and co-polymers synthesized by the well-established ring opening polymerization (ROP) process (Dechy-Cabaret et al., 2004; Kricheldorf et al., 1995; Schwach et al., 1997; Degee et al., 1999; Ryner et al., 2001) have a glass transition temperature ($T_g$) limited to a range of only 40-60° C. (Jamshidi et al., 1988; Vert et al., 1984), independent of the polymer molecular weight and chemical composition. This combined with interesting mechanical properties makes them suitable in medical applications as biodegradable implants, bone fracture fixation devices, scaffolds for living cells.

These polylactides, however, have significant limitations for drug delivery purposes. For drug delivery purposes, polylactides need to be formulated with organic solvents and administered as solutions or in form of nano- and microparticles, and polylactides can not be injected on their own. Thus there is a significant need for a polylactide which may be used for drug delivery that does not require the use of an organic solvent or to form nano- and micro-particles.

SUMMARY OF THE INVENTION

The present invention provides compositions and methods relating to polylactides which may be used for drug delivery which do not require the use of an organic solvent or to form nano- and micro-particles prior to injection. These polylactides may be used, for example, to administer a drug to a subject (e.g., a human patient) parenterally without the use of a solvent.

An aspect of the present invention relates to a method of preparing a pharmaceutical preparation comprising admixing a drug with an alkyl substituted polylactide; wherein the alkyl substituted polylactide is viscous; and wherein a solvent is not required for said admixing. The pharmaceutical preparation may be injectable. The pharmaceutical preparation may be formulated for parenteral administration to a subject. The subject may be a mammal, such as a human, a mouse, rat, a sheep, a goat, a horse, a dog, a cat, a monkey, a cow, or a pig.

In certain embodiments, the alkyl substituted polylactide has the structure:

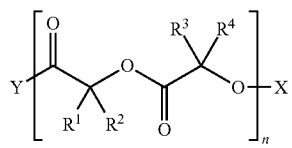

wherein $R^1$, $R^2$, $R^3$, and $R^4$ are each independently chosen from the group consisting of unsubstituted alkyl, H, alkenyl and unsubstituted alkylaryl; wherein n is 1 to 100; wherein X is hydrogen, —C(O)—CH=$CH_2$ or any other functional or crosslinking group; and Y is selected from the group consisting of —OH, an alkoxy, benzyloxy and —O—($CH_2$—$CH_2$—O)$_p$—$CH_3$, and wherein p is 1 to 700. In certain embodiments, n is 1 to 100, more preferably 1 to 75, more preferably 1 to 50, more preferably 1 to 25, more preferably 1 to 10. In certain embodiments, $R^1$ and $R^3$ are hydrogen and $R^2$ and $R^4$ are lower alkyl. For example, $R^2$ and $R^4$ may be —($CH_2$)$_m$—$CH_3$, wherein m is from 0 to 20. In certain embodiments, m is from 0 to 12.

The alkyl substituted polylactide may be synthesized from alkyl substituted lactide monomers, for example, 3-Methyl-6-hexyl-1,4-dioxane-2,5-dione, 3-6-Dihexyl-1,4-dioxane-2,5-dione, 3,6,6-Trimethyl-1,4-dioxane-2,5-dione, 3-Methyl-6-isopropyl-1,4-dioxane-2,5-dione, 3-Methyl-6-butyl-1,4-dioxane-2,5-dione, 3-Benzyl-6-methyl-1,4-dioxane-2,5-dione. In certain embodiments, the alkyl substituted polylactide has 1-, 2-, 3- or 4 substituents on the lactide-repeating-unit in the polymer chain. In certain embodiments, the alkyl substituted polylactide has 1-, 2-, 3- or 4 substituents on the lactide-repeating-unit in the polymer chain (i.e., 1, 2, 3 or all of $R^1$, $R^2$, $R^3$ and $R^4$ are substituents that are not —H).

The solvent may not be used for said admixing, or the solvent may be used for said admixing. The solvent may be an organic solvent.

In certain embodiments, the polylactide is made by the process of subjecting a compound to chemical reaction, wherein the compound has the structure:

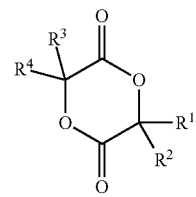

wherein $R^1$, $R^2$, $R^3$, and $R^4$ are each independently chosen from the group consisting of unsubstituted alkyl, H, alkenyl and unsubstituted alkylaryl. The chemical reaction may be a ring opening polymerization (ROP). An organic catalyst or an inorganic catalyst may be used in said ROP. The organic catalyst may be tin(II) 2-ethylhexanoate (Sn(Oct)$_2$), tin(II) trifluoromethane sulfonate (Sn(OTf)$_2$), 4-(dimethylamino) pyridine (DMAP). In certain embodiments, an alcohol initiator is used in the ROP. The alcohol initiator may be benzyl alcohol, methoxy-poly(ethylene glycol) (MPEG), 1,1,1-tris (hydroxymethyl)ethane (TE) or pentaerythritol (PE) or any other multi-hydroxy compound. In certain embodiments an alcohol initiator is not used in said ROP. In certain embodiments, the polylactide is acrylated or functionalized with a crosslinkable group.

In certain embodiments, the compound is 3-Methyl-6-hexyl-1,4-dioxane-2,5-dione, 3-6-Dihexyl-1,4-dioxane-2,5-dione, 3,6,6-Trimethyl-1,4-dioxane-2,5-dione, 3-Methyl-6-isopropyl-1,4-dioxane-2,5-dione, 3-Methyl-6-butyl-1,4-dioxane-2,5-dione or 3-Benzyl-6-methyl-1,4-dioxane-2,5-dione.

Another aspect of the present invention relates to a composition suitable for parenteral administration, wherein the composition comprises an alkyl substituted polylactide, and wherein the alkyl substituted polylactide is viscous and has the structure:

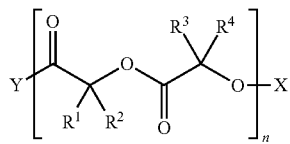

wherein $R^1$, $R^2$, $R^3$, and $R^4$ are each independently chosen from the group consisting of unsubstituted alkyl, H, alkenyl and unsubstituted alkylaryl; wherein n is 1 to 100; wherein X is hydrogen or —C(O)—CH=CH$_2$ or any other functional or crosslinking group; and Y is selected from the croup consisting of —OH, an alkoxy, benzyloxy or —O—(CH$_2$—CH$_2$—O)$_p$—CH$_3$; and wherein p is 1 to 700, more preferably 1 to 250. In certain embodiments, n is 1 to 100, more preferably 1 to 75, more preferably 1 to 50. In certain embodiments, $R^1$ and $R^3$ are hydrogen and $R^2$ and $R^4$ are lower alkyl. For example, $R^2$ and $R^4$ may be —(CH$_2$)$_m$—CH$_3$, wherein m is from 0 to 20. In certain embodiments, m is from 0 to 12.

In certain embodiments, the alkyl substituted polylactide may be synthesized from alkyl substituted lactide monomers including: 3-Methyl-6-hexyl-1,4-dioxane-2,5-dione, 3-6-Dihexyl-1,4-dioxane-2,5-dione, 3,6,6-Trimethyl-1,4-dioxane-2,5-dione, 3-Methyl-6-isopropyl-1,4-dioxane-2,5-dione, 3-Methyl-6-butyl-1,4-dioxane-2,5-dione, 3-Benzyl-6-methyl-1,4-dioxane-2,5-dione. In certain embodiments, the alkyl substituted polylactide has 1, 2, 3 or 4 substituents on the lactide-repeating-unit in the polymer chain (i.e., 1, 2, 3 or all of $R^1$, $R^2$, $R^3$ and $R^4$ are substituents that are not —H).

Another aspect of the present invention relates to a compound having the structure:

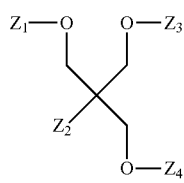

wherein $Z_2$ is selected from the group consisting of —CH$_3$ and —CH$_2$—O—$Z_5$; and wherein $Z_1$, $Z_3$, $Z_4$, and $Z_5$, each independently has the structure:

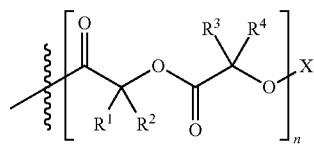

wherein $R_1$, $R_2$, $R_3$, and $R_4$ are each independently chosen from the group consisting of unsubstituted alkyl, H, alkenyl and unsubstituted alkylaryl; wherein n is 1 to 100; wherein X is hydrogen, —C(O)—CH=CH$_2$ or any other functional or crosslinking group. In certain embodiments, n is 1 to 100, more preferably 1 to 75, more preferably 1 to 50. In certain embodiments, $R_1$ and $R_3$ are hydrogen; and $R_2$ and $R_4$ are lower alkyl. In certain embodiments, $R^2$ and $R^4$ are —(CH$_2$)$_m$—CH$_3$, wherein m is from 0 to 20. In certain embodiments, m is from 0 to 12. In certain embodiments, $Z_2$ is —CH$_3$; $R_1$ and $R_3$ are hydrogen; $R^2$ and $R^4$ are —(CH$_2$)$_m$—CH$_3$, wherein m is from 0 to 20; and X is hydrogen. In certain embodiments, $Z_2$ is —CH$_3$; $R_1$ and $R_3$ are hydrogen; $R_2$ and $R_4$ are —(CH$_2$)$_m$—CH$_3$, wherein m is from 0 to 12; and X is —C(O)—CH=CH$_2$ or any other functional or crosslinking group. In certain embodiments, $Z_2$ is —CH$_2$—O—$Z_5$; $R_1$ and $R_3$ are hydrogen; $R^2$ and $R^4$ are —(CH$_2$)$_m$—CH$_3$, wherein m=0 or m=5; and X is hydrogen. In certain embodiments, $Z_2$ is —CH$_2$—O—$Z_5$; $R_1$ and $R_3$ are hydrogen; $R^2$ and $R^4$ are —(CH$_2$)$_m$—CH$_3$, wherein m=0 or m=5; and X is —C(O)—CH=CH$_2$ or any other functional or crosslinking group.

Another aspect of the present invention relates to a compound having the structure:

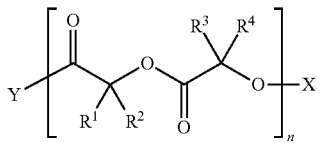

wherein $R^1$, $R^2$, $R^3$, and $R^4$ are each independently chosen from the group consisting of unsubstituted alkyl, H, alkenyl and unsubstituted alkylaryl; wherein n is 1 to 100; wherein X is hydrogen, —C(O)—CH=CH$_2$ or any other functional or crosslinking group; and Y is —O—(CH$_2$—CH$_2$-0)$_p$—CH$_3$; wherein p is 1 to 700. In certain embodiments, n is 1 to 100, more preferably 1 to 75, more preferably 1 to 50. p may be 1 to 700, more preferably 1 to 250. In certain embodiments, $R_1$ and $R_3$ are hydrogen; and $R_2$ and $R_4$ are lower alkyl. In certain embodiments, $R^2$ and $R^4$ are —(CH$_2$)$_m$—CH$_3$, wherein m is from 0 to 20. In certain embodiments, m is from 0 to 12.

Another aspect of the present invention relates to a polylactide made by the process of subjecting a compound to a ring opening polymerization (ROP) in the presence of an alcohol initiator, wherein the compound has the structure:

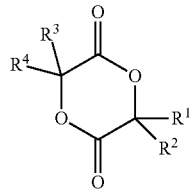

wherein $R^1$, $R^2$, $R^3$, and $R^4$ are each independently chosen from the group consisting of unsubstituted alkyl, H, alkenyl and unsubstituted alkylaryl; and wherein the alcohol initiator is benzyl alcohol, methoxy-poly(ethylene glycol) (MPEG), 1,1,1-tris(hydroxymethyl)ethane (TE) or pentaerythritol (PE) or any other multi-hydroxy compound. $R^1$, $R^2$, $R^3$, and $R^4$ may be lower alkyl. An organic catalyst or inorganic catalyst may be used in said ROP. The organic catalyst may be tin(II) 2-ethylhexanoate ($Sn(Oct)_2$), tin(II)trifluoromethane sulfonate ($Sn(OTf)_2$) and/or 4-(dimethylamino)pyridine (DMAP). In certain embodiments, the polylactide is acrylated or functionalized with a crosslinkable group.

Another aspect of the present invention relates to a method of making a polylactide comprising subjecting a compound to a ring opening polymerization (ROP) in the presence of an alcohol initiator, wherein the compound has the structure:

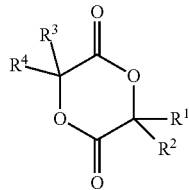

wherein $R^1$, $R^2$, $R^3$, and $R^4$ are each independently chosen from the group consisting of unsubstituted alkyl, H, alkenyl and unsubstituted alkylaryl; and wherein the alcohol initiator is benzyl alcohol, methoxy-poly(ethylene glycol) (MPEG), 1,1,1-tris(hydroxymethyl)ethane (TE) or pentaerythritol (PE) or any other multi-hydroxy compound. $R^1$, $R^2$, $R^3$, and $R^4$ may be lower alkyl. An organic catalyst or inorganic catalyst may be used in said ROP. The organic catalyst may be tin(II) 2-ethylhexanoate ($Sn(Oct)_2$), tin(II)trifluoromethane sulfonate ($Sn(OTf)_2$) and/or 4-(dimethylamino)pyridine (DMAP) or any other catalyst. In certain embodiments, the polylactide is acrylated or functionalized with any other crosslinkable group.

Another aspect of the present invention relates to a method of treatment comprising administering a pharmaceutical composition of the present invention to a subject. The composition may be administered parenterally. The subject may be a mammal, such as a human, a mouse, rat, a sheep, a goat, a horse, a dog, a cat, a monkey, a cow, or a pig. In certain embodiments the composition is injected into the subject.

As used herein the specification, "a" or "an" may mean one or more. As used herein in the claim(s), when used in conjunction with the word "comprising", the words "a" or "an" may mean one or more than one. As used herein "another" may mean at least a second or more.

It is contemplated that any embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 6A-C: Molecular weight decrease and weight loss of PmHLA (●) and PLA (○) of (FIG. 6A) 4500 g/mol, (FIG. 6B) 7500 g/mol, (FIG. 6C) 9100 g/mol at 37° C. in phosphate buffer pH 7.4 [For graph (a), benzyl ester-terminated PmHLA (●) was compared to the carboxy-terminated PmHLA (■)].

FIG. 7: Molecular weight decrease and weight loss of PmHLA (●) and PLA (○) of 7500 g/mol at 60° C. in phosphate buffer pH 7.4.

DESCRIPTION OF ILLUSTRATIVE EMBODIMENTS

Figure 1:
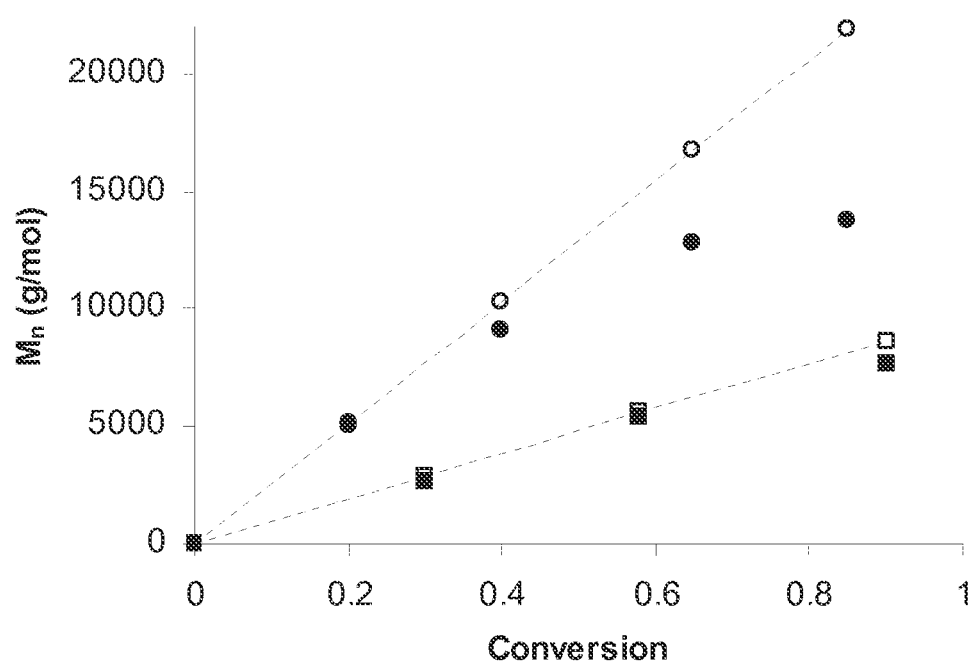
FIG. 1: Molecular weight versus conversion for the ROP of the monohexyl-substituted lactide mHLA at 100° C. in bulk, with targeted DP of 45 (■: experimental; □: expected) and 120 (●: experimental; ○: expected) ([BnOH]/[$Sn(Oct)_2$]=1).

The present invention provides compositions and methods relating to polylactides which may be used for drug delivery which do not require the use of an organic solvent or to form nano- and micro-particles prior to injection. These polylactides may be used, for example, to administer a drug to a subject (e.g., a human patient) parenterally without the use of a solvent.

CHEMICAL DEFINITIONS

An "alkyl" group, as used herein, refers to a saturated aliphatic hydrocarbon, including straight-chain, branched chain, and cyclic alkyl groups. Preferably, the alkyl group has 1 to 20 carbons, more preferably 1 to 12 carbons, more preferably 1 to 10. Most preferably, it is a lower alkyl of from 1 to 12 carbons. The alkyl groups of the present invention are preferably unsubstituted. For example, —$CH_3$, —$CH(CH_3)_2$ and —$(CH_2)_nCH_3$, wherein n is 1, 2, 3, 4, 5, 6, 7, 8, 9, 10, 11, 12, 13, 14, 15, 16, 17, 18, 19 or 20 are contemplated alkyl groups that may be used in certain embodiments of the present invention.

An "alkenyl" group, as used herein, refers to an unsaturated aliphatic hydrocarbon, including straight-chain, branched chain, and cyclic alkyl groups. Preferably, the alkenyl group has 1 to 20 carbons, more preferably 1 to 12 carbons, more preferably 1 to 10. Most preferably, it is a lower alkenyl of from 1 to 12 carbons.

An "aryl" group, as used herein, refers to an unsubstituted aromatic group which has at least one ring having a conjugated pi electron system, and includes carbocyclic aryl, heterocyclic aryl, and biaryl groups. In certain preferred embodiments, the aryl is an unsubstituted phenyl.

An "alkylaryl" group, as used herein, refers to an alkyl (as described above), covalently joined to an aryl group (as described above). Preferably, the alkyl is a lower alkyl. For example, —$(CH_2)$—$(C_6H_5)$ is contemplated as an alkylaryl, wherein n is 1 to 20.

An "alkoxy" group refers to an "—O-alkyl" group, where "alkyl" is defined above.

A "benzyloxy" group, as used herein, refers to the group

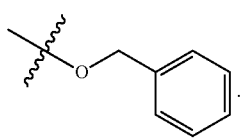 [SMILES: *OCc1ccccc1]

"Viscous", as used herein to describe a polylactide, refers to a polylactide that has a glass transition temperature (Tg) value of less than 44 C, more preferably less than 36 C, more preferably less than 35 C, more preferably less than 34 C, more preferably less than 33 C, more preferably less than 32 C, more preferably less than 31 C, more preferably less than 30 C, more preferably less than 29 C, more preferably less than 28 C, more preferably less than 27 C, more preferably less than 26 C, more preferably less than 25 C, more preferably less than 24 C, more preferably less than 23 C, more preferably less than 22 C, more preferably less than 21 C, more preferably less than 20 C, more preferably less than 19 C, more preferably less than 18 C, more preferably less than 17 C, more preferably less than 16 C, more preferably less than 15 C, more preferably less than 14 C, more preferably less than 13 C, more preferably less than 12 C, more preferably less than 11 C, more preferably less than 10 C, more preferably less than 9 C, more preferably less than 8 C, more preferably less than 7 C, more preferably less than 6 C, more preferably less than 5 C, more preferably less than 4 C, more preferably less than 3 C, more preferably less than 2 C, more preferably less than 1 C, more preferably less than 0 C, more preferably less than −1 C, more preferably less than −2 C, more preferably less than −3 C, more preferably less than −4 C, more preferably less than −5 C, more preferably less than −6 C, more preferably less than −7 C, more preferably less than −8 C, more preferably less than −9 C, most preferably less than −10 C.

Polylactides

Polylactides are known in the art. For example, U.S. Pat. No. 6,469,133, U.S. Pat. No. 6,126,919 describe various polylactides and are incorporated by reference herein in their entirety without disclaimer. Polylactides are biodegradable which enhances their utility. For example, polylactides may be degraded in the body of a subject (e.g., a human patient) into the constituent hydroxycarboxylic acid derivatives (i.e. lactic acids) that form over a period of weeks or years. Polylactides can have molecular weights from about 2000 Da to about 250,000 Da. For these reasons, polylactides may be attractive for generating things such as degradable sutures, pre-formed implants, and compounds for drug delivery (e.g., sustained release matrices).

"Alkyl substituted lactide", as used herein, refers to a compound comprising the structure

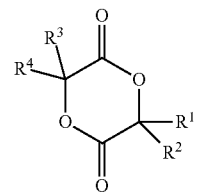

or a compound having the structure:

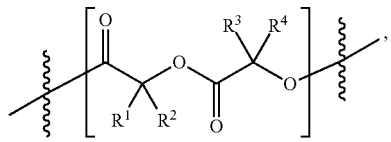

wherein $R^1$, $R^2$, $R^3$, and $R^4$ are each independently chosen from the group consisting of unsubstituted alkyl, H, alkenyl and unsubstituted alkylaryl.

"Alkyl substituted polylactide", as used herein, refers to a compound structure:

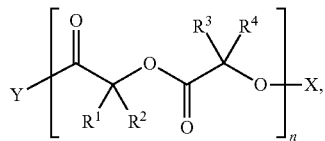

wherein $R^1$, $R^2$, $R^3$, and $R^4$ are each independently chosen from the group consisting of alkyl (e.g., unsubstituted alkyl), H, alkenyl and alkylaryl (e.g., unsubstituted alkylaryl); wherein X is hydrogen or, alternatively, has been produced as a result of any further functionalization by chemical reaction on the —OH group formed by the —OX wherein X is hydrogen; Y been derived from any initiator alcohol, or Y is selected from the croup consisting of —OH, an alkoxy, benzyloxy and —O—$(CH_2$—$CH_2$—$O)_p$—$CH_3$; and wherein p 1 to 700, more preferably 1 to 250; and wherein n is an integer from 1 to 500 or more, more preferably 1 to 100, more preferably 1 to 50, more preferably 1 to 25. In certain embodiments, n is from 1 to 12, from 1 to 6, 1, 2, 3, 4, 5, 6, 7, 8, 9, or 10.

In certain embodiments, $R^1$ and $R^3$ are hydrogen and $R^2$ and $R^4$ are lower alkyl. For example, $R^2$ and $R^4$ may be —$(CH_2)_m$—$CH_3$, wherein m is from 0 to 20, more preferably 0 to 15, more preferably 0 to 10, more preferably m=0 or m=5. In certain embodiments, m is from 0 to 6, 0, 1, 2, 3, 4, 5, 6, 7, 8, 9, 10, 11 or 12.

In certain embodiments an alkyl substituted polylactide may have the structure:

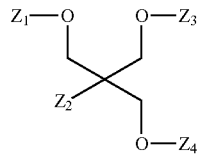

wherein $Z_2$ is selected from the group consisting of —$CH_3$ and —$CH_2$—$O$—$Z_5$; and wherein $Z_1$, $Z_3$, $Z_4$, and $Z_5$, each independently has the structure:

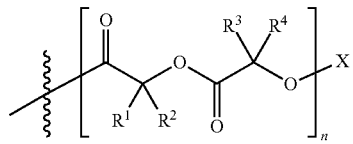

wherein $R_1$, $R_2$, $R_3$, and $R_4$ are each independently chosen from the group consisting of alkyl (e.g., unsubstituted alkyl), H, alkenyl and alkylaryl (e.g., unsubstituted alkylaryl); wherein n is 1 to 100; wherein X is hydrogen, —C(O)—CH=$CH_2$ or any other functional or crosslinking group. In certain embodiments, n is 1 to 75, more preferably 1 to 50, more preferably 1 to 25. In certain embodiments, $R_1$ and $R_3$ are hydrogen; and $R_2$ and $R_4$ are lower alkyl. In certain embodiments, $R_2$ and $R_4$ are —$(CH_2)_m$—$CH_3$, wherein m is from 0 to 20. In certain embodiments, m is from 0 to 20, more preferably 0 to 15, more preferably 0 to 10, more preferably m=0 or m=5. In certain embodiments, $Z_2$ is —$CH_3$; $R_1$ and $R_3$ are hydrogen; $R_2$ and $R_4$ are —$(CH_2)_m$—$CH_3$, wherein m is from 0 to 20; and X is hydrogen. In certain embodiments, $Z_2$ is —$CH_3$; $R_1$ and $R_3$ are hydrogen; $R_2$ and $R_4$ are —$(CH_2)_m$—$CH_3$, wherein m is from 0 to 20; and X is —C(O)—CH=$CH_2$ or any other functional or crosslinking group. In certain embodiments, $Z_2$ is —$CH_2$—$O$—$Z_5$; $R_1$ and $R_3$ are hydrogen; $R_2$ and $R_4$ are —$(CH_2)_m$—$CH_3$, wherein m is from 0 to 20; and X is hydrogen. In certain embodiments, $Z_2$ is —$CH_2$—$O$—$Z_5$; $R_1$ and $R_3$ are hydrogen; $R^2$ and $R^4$ are —$(CH_2)_m$—$CH_3$, wherein m is from 0 to 20; and X is —C(O)—CH=$CH_2$. In certain embodiments, m may be from 0 to 20, 0 to 16, 0 to 12, or 0 to 6.

In certain embodiments an alkyl substituted polylactide may have the structure:

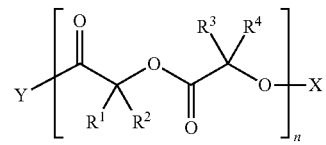

wherein $R^1$, $R^2$, $R^3$, and $R^4$ are each independently chosen from the group consisting of alkyl (e.g., unsubstituted alkyl), H, alkenyl and alkylaryl (e.g., unsubstituted alkylaryl); wherein n is 1 to 100; wherein X is hydrogen or —C(O)—CH=$CH_2$ or any other functional or crosslinking group; and Y is —O—$(CH_2$—$CH_2$—$O)_p$—$CH_3$; wherein p is 1 to 700, more preferably 1 to 250. In certain embodiments, n is 1 to 100, more preferably 1 to 75, more preferably 1 to 50, more preferably 1 to 25, 1 to 12 or 1 to 6. In certain embodiments, $R_1$ and $R_3$ are hydrogen; and $R_2$ and $R_3$ are lower alkyl. In certain embodiments, $R^2$ and $R^4$ are —$(CH_2)_m$—$CH_3$, wherein m is from 0 to 20, more preferably 0 to 6. In certain embodiments, m is from 0 to 6, 0, 1, 2, 3, 4, 5, 6, 7, 8, 9, 10, 11, 12.

The alkyl substituted polylactides of the present invention may comprise a drug (e.g., a hydrophobic drug or a hydrophilic drug), and the alkyl substituted polylactides of the present invention may be used to deliver a drug to a subject (e.g., a human patient). In certain embodiments, the alkyl substituted polylactides of the present invention are used to deliver a hydrophobic drug, such as tetracycline, to a subject.

Further, the alkyl substituted polylactides of the present invention may be used to alter the pharmacokinetics of a drug. For example, in certain embodiments, the substituted polylactides of the present invention may be used to reduce the degradation of a drug. In certain embodiments, the substituted polylactides of the present invention may be used to more completely (i.e., as compared to PLA) release the drug (e.g., an active form of the drug) into a subject.

A. Synthesis of Polylactides

Certain polylactides of the present invention may be synthesized by the general synthesis paradigm:

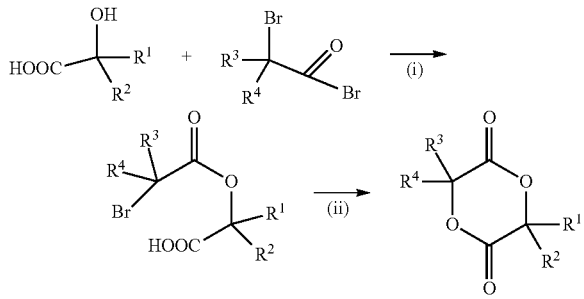

wherein $R^1$, $R^2$, $R^3$, and $R^4$ are each independently chosen from the group consisting unsubstituted alkyl (e.g., unsubstituted alkyl), H, alkenyl or alkylaryl (e.g., unsubstituted alkylaryl). A subsequent ring opening polymerization (ROP) may be performed using, for example, tin(II) 2-ethylhexanoate $(Sn(Oct)_2)$, tin(II)trifluoromethane sulfonate $(Sn(OTf)_2)$, 4-(dimethylamino)pyridine (DMAP), and/or another organic catalyst. In certain embodiments, $Sn(Oct)_2$ is used as the catalyst.

For example, ring-opening polymerizations may be performed with the "standard" FDA-approved (Food Drug Admin, 1975) metal organic catalysts $Sn(Oct)_2$, with the more reactive "tin-based" tin(II)trifluoromethane sulfonate $Sn(OTf)_2$ (Möller et al., 2000; Möller et al., 2001) and/or the solely organic catalyst 4-(dimethylamino)pyridine DMAP (Nederberg et al., 2001). The "coordination-insertion" mechanism for ROP of cyclic esters has been well established and described, e.g., by Kowalski et al. (1998). Kricheldorf et al. (2000) and others for the most commonly used $Sn(Oct)_2$ catalyst. In this reaction mechanism $Sn(Oct)_2$ exchanges at least one of its 2-ethylhexanoate ligands with the initiating alcohol to form a tin alkoxide initiator. In these embodiments, after monomer ring-opening leading to an alcohol ester end group the propagation proceeds through the tin alkoxide active centers. This mechanism can also apply to the ROP used here in certain embodiments for the polymerizations of the alkyl-substituted monomers catalyzed by Sn(Oct)$_2$, Sn(OTf)$_2$ and DMAP, respectively. The use of benzyl alcohol (BnOH) as the alcohol initiator can enable later further functionalization of the polymers by deprotection of the benzyl end groups with H$_2$/Pd. In certain embodiments where steric more hindered monomers cannot be efficiently polymerized with Sn(Oct)$_2$ and Sn(OTf)$_2$, the use of the DMAP catalyst may be successfully applied. Good control of molecular weight and narrow polydispersities may be achieved for ROP of, e.g., monoalkyl-substituted monomers leading to new functionalized poly(lactides).

In certain embodiments, an alcohol initiator may be used in the ROP. In other embodiments, an alcohol initiator is not used in the ROP. Alcohol initiators include: benzyl alcohol, methoxy-poly(ethylene glycol) (MPEG), 1,1,1-tris(hydroxymethyl)ethane (TE) and pentaerythritol (PE). Other alcohol inhibitors that may be used with the present invention include molecules with multiple hydroxy groups.

In certain embodiments, a subsequent acrylation step or a functionalization with a crosslinking compound may be performed. For example, acrylation may be performed by subjecting a polylactide to an excess of acryloyl chloride. Crosslinking may be achieved by any other crosslinking agent, wherein the crosslinking groups comprise degradable or nondegradable functionality.

In certain embodiments, a polylactide may be made by the process of subjecting a compound to a ring opening polymerization (ROP) in the presence of an alcohol initiator, wherein the compound has the structure:

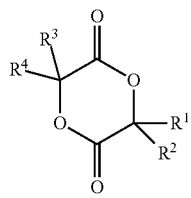

wherein $R^1$, $R^2$, $R^3$, and $R^4$ are each independently chosen from the group consisting of unsubstituted alkyl, H, alkenyl and unsubstituted alkylaryl; and wherein the alcohol initiator is benzyl alcohol, methoxy-poly(ethylene glycol) (MPEG), 1,1,1-tris(hydroxymethyl)ethane (TE), pentaerythritol (PE) or a compound with multiple hydroxy groups. $R^1$, $R^2$, $R^3$, and $R^4$ may be lower alkyl. An organic catalyst may be used in said ROP. The organic catalyst may be tin(II) 2-ethylhexanoate (Sn(Oct)$_2$), tin(II)trifluoromethane sulfonate (Sn(OTf)$_2$) and/or 4-(dimethylamino)pyridine (DMAP). In certain embodiments, the polylactide is acrylated or functionalized with a crosslinking compound.

In certain embodiments, the compound may have any of the following structures:

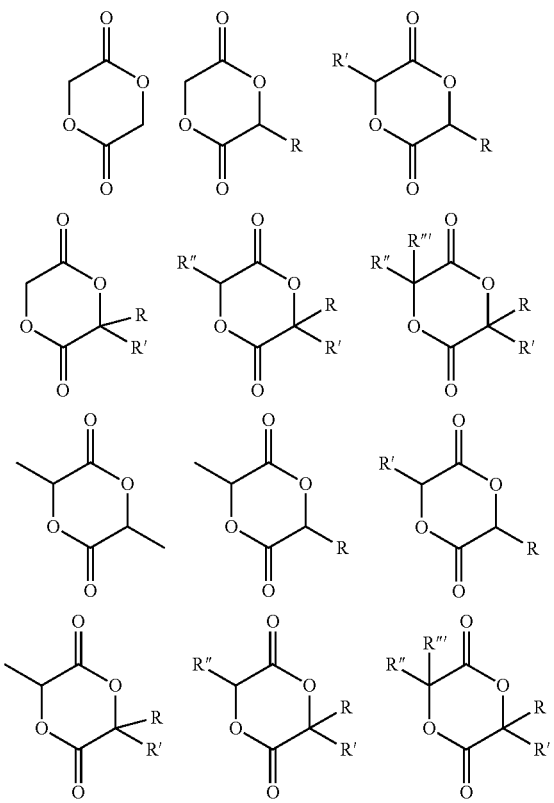

mono-di-di-tri-tetra-subsitution

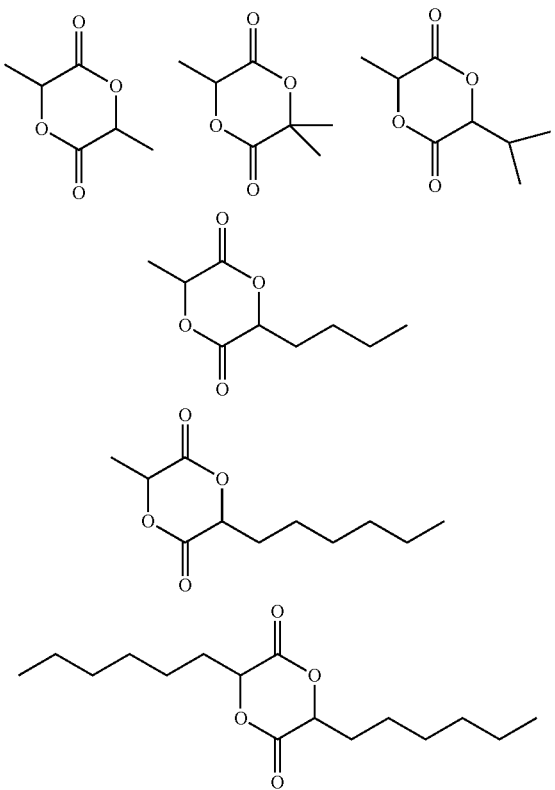

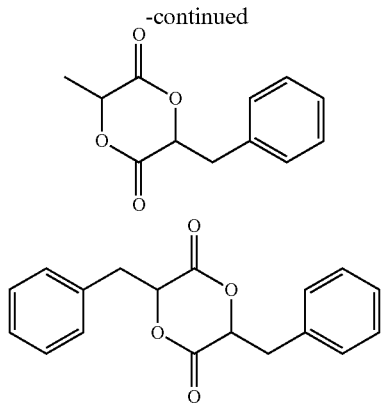

These compounds may be used to produce an alkyl substituted polylactide which has 1, 2, 3 or 4 substituents on the lactide-repeating-unit in the polymer chain (i.e., 1, 2, 3 or all of $R^1$, $R^2$, $R^3$ and $R^4$ (R, R', R" and R'" above) are substituents that are not hydrogen).

B. Use of Polylactides in Combination with Other Compounds

The polylactides of the present invention may be used in combination with other polylactides, polyglycolides and their copolymers. For example, the polylactides of the present invention may be admixed with or contacted with a second compound and the resulting composition may be used for drug delivery. Compounds which may be used as the second compound or in combination with the polylactides of the present invention include polyglycolide (PLGA), polylactic acid (PLA), polycaprolactone (PCL), polyethylene glycol (PEG), polydioxanone (PDO), poly(D,L-lactide-co-glycolide) and poly(L-lactide-co-glycolide), poly(hydroxyl alkanoate) (PHA), and biodegradable and biocompatible polymers. Biocompatible polymers include polyester, polyether, polyanhydride, polyamines, poly(ethylene imines) polyamides, polyesteramides, polyorthoesters, polydioxanones, polyacetals, polyketals, polycarbonates, polyphosphoesters, polybutylene, polyterephthalate, polyorthocarbonates, polyphosphazenes, polyurethanes, polytetrafluorethylenes (PTFE), polysuccinates, poly(malic acid), poly(amino acids), polyvinylpyrrolidone, polyhydroxycellulose, polysaccharides, chitin, chitosan, hyaluronic acid, and copolymers, terpolymers and mixtures thereof. In certain embodiments, synthetic polymers and/or natural polymers (e.g., as listed below) may be used as the second compound or in combination with polylactides of the present invention.

Synthetic Polymers

| Degradable: | Non-Degradable: |
|---|---|
| Poly(glycolic) acid and Poly(lactic acid) | Poly acrylic acids |
| in general: Poly(hydroxyl alkanoates) (PHAs) | Poly methylmethacrylate (PMMA) |
| | Poly acryl amides |
| | Poly acrylo nitriles/= cyano acrylates |
| Poly capro-, butyro-, valero-lactones | Poly functionalized methacrylic acids |
| | Poly urethanes |
| Poly orthoesters | Poly olefins |
| Poly anhydrides | Poly styrene |
| Poly carbonates | Poly terephthalates |
| Polyester from alcanoic acids + dialcohols | Poly ethylenes, propylenes |
| | Poly ether ketones |
| Poly amides | Poly vinylchlorides |
| Poly imides | Poly fluorides |
| Poly imines | Poly PTFE |

| Degradable: | Non-Degradable: |
|---|---|
| Poly imino carbonates | Silicones |
| Poly ethylene imines | Poly silicates (bioactive glass) |
| Poly dioxanes | Siloxanes (Poly dimethyl siloxanes) |
| Poly phosphazenes | |
| Poly sulphones | |
| Synthetic Lipids | |

Natural Polymers:
Poly(aminoacids) (natural and (non natural poly β-aminoesters))
    e.g.: Poly (aspartic acid), -(glutamic acid), -(lysine), -(histidine)
Poly(peptides) and proteins
Poly and oligo nucleic acids
    Albumines
    Alginates
    Cellulose/Cellulose acetates
    Chitin/Chitosan
    Collagene
    Fibrine/Fibrinogen
    Gelatine
    Lignine
    Poly(hyaluronic acids)
        (hydroxyalkanoates)
        isoprenoids
        saccharides
    Starch based polymers C. Use of Polylactides in Combination with Plasticizers In certain embodiments it may be desirable to contact or admix an alkyl substituted polylactide with one or more pasticizers, in order to alter the physical properties (e.g., lowering the $T_g$) of the resulting composition. Plasticizers which may be used in combination with an alkyl substituted polylactide include all FDA approved plasticizers, such as benzyl benzoates, cellulose acetates, cellulose acetate phthalates, chlorobutanol, dextrines, dibutyl sebacate, dimethyl sebacate, acetyl phthalates, diethyl phthalate dibutyl phthalate, dipropyl phthalate, dimethyl phthalate, dioctyl phthalate, methyl cellulose, ethyl cellulose, hydroxylethyl cellulose, hydroxypropyl cellulose, hydroxypropyl methyl celluloses, gelatine, glycerines, glyceryl monostearate, monoglycerides, mono and di-acetylated monoglycerides, glycerol, mannitol, mineral oils and lanolin alcohols, petrolatum and lanolin alcohols, castor oil, vegetable oils, coconut oil, polyethylene glycol, polymethacrylates and copolymers thereof, polyvinylpyrrolidone, propylene carbonates, propylene glycol, sorbitol, suppository bases, diacetine, triacetin, triethanolamine, esters of citric acid, triethyl citrate, acetyl triethyl citrate, acetyl tributyl citrate, triethyl citrate, esters of phosphoric acid.

For example, certain alkyl substituted polylactides of the present invention (e.g., polylactides with higher molecular weights) may be waxy and thus not injectable. However, these alkyl substituted polylactides may still retain the very desirable property of being very hydrophobic in comparison to normal PLA/PLGA, thus having an advantage for many pharmaceutical applications. An increased hydrophobic drug incorporation into the alkyl substituted polylactide due to the increased hydrophobicity of the polylactide. Certain alkyl substituted polylactides of the present invention (e.g., polylactides with higher molecular weights) may exhibit better control of drug release. Thus, in certain embodiments a non-injectable alkyl substituted polylactide could be made injectable by admixing a plasticizer with the polylactide.

Pharmaceutical Preparations

Pharmaceutical compositions of the present invention comprise an effective amount of one or more alkyl substituted polylactide or additional agent dissolved in, dispersed in, or used as a pharmaceutically acceptable carrier. Further it is recognized that one or more alkyl substituted polylactide may be used in combination with an additional agent in or as a pharmaceutically acceptable carrier.

The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one alkyl substituted polylactide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The alkyl substituted polylactide may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The alkyl substituted polylactide may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include alkyl substituted polylactide, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the alkyl substituted polylactide may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the alkyl substituted polylactide are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, *acacia*, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, an alkyl substituted polylactide may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound alkyl substituted polylactide may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis and Ring-Opening Polymerization of New Alkyl-Substituted Lactides Biocompatible and biodegradable poly(lactide) materials have received high interest over the past three decades, initially in the biomedical field, e.g as sutures and implants or as drug-delivery systems (Penning et al., 1993; Uhrich et al., 1999). They are also reported and used as environmentally friendly packaging materials (Drumright et al., 2000), and commercially applied in areas as wide as foams, apparels, carpets or mattresses (Vink et al., 2003). Based on the lactide monomer, which is synthesized from renewable resources, and thanks to the reduced polymer costs allowed by new industrial scale technologies, biodegradable poly(lactides) have major advantages to other synthetic polymers.

The ability of modulating the physico-chemical properties of the polymer (hydrophobicity/philicity, degradability, $T_g$, etc.) is a key point for obtaining materials adapted to their specific application. In this context the design of new controlled polymerizable alkyl-substituted lactides (referring to lactides, in which at least one of the methyl ligand is substituted by an other alkyl substituent) can be an interesting approach to tailor material properties for various medical applications by using them as new homopolymers or as new copolymers together with lactides and glycolides. Although the ring-opening polymerization (ROP) of lactides is widely described in the literature (Kricheldorf et al., 1995; Hyon et al., 1997; Schwach et al., 1997; Degee et al., 1999; Ryner et al., 2001; Shirahama et al., 2002; Myers et al., 2002; Ouchi et al., 2002; Storey et al., 2002; Finne et al., 2003; Mullen et al., 2003; Mullen et al., 2003; McGuinness et al., 2003), the synthesis and the ROP of aliphatic derivatives are hardly investigated (Lou et al., 2003). Only recently Baker et al. reported the polymerization of the symmetric dibenzyl-substituted lactide 3,6-di(phenylmethyl)-1,4-dioxane-2,5-dione (6' as shown below). Polymerizations carried out in solution at 50-100° C. with tin(II) 2-ethylhexanoate (Sn(Oct)$_2$) as catalyst led to relative low conversions (<70%) even after a reaction time of one week, whereas melt polymerization at 180° C. allowed 90% conversion within two hours. Nevertheless in this latter case side transesterification and epimerization reactions were observed after prolonged polymerization times (Simmons and Baker, 2001). This group also reported the synthesis of other new symmetric substituted lactides, such as 3,6-diethyl-1,4-dioxane-2,5-dione, 3,6-diisobutyl-1,4-dioxane-2,5-dione and 3,6-dihexyl-1,4-dioxane-2,5-dione (5') (Yin and Baker, 1999). The ring-opening polymerizations of these monomers in presence of several tin-based catalysts, with or without alcohol initiator, at relative high temperatures (130-180° C.) led to polymers showing high polydispersities (>1.7). The substituted lactides syntheses were realized by two different methods, either by the classical condensation of the corresponding α-hydroxy acid (Deane and Hammond, 1960) or by the two-step synthesis of an α-hydroxy acid with a 2-halo-alkanoyl halogenide reported prior by Schöllkopf et al. (1979). Baker and Smith (2002) describe an ROP with metal organic catalysts.

Structures of synthesized substituted lactides are shown below; 1: D,L-lactide, 2: 3,6,6-Trimethyl-1,4-dioxane-2,5-dione (referred as dimethyl-substituted lactide), 3: 3-Methyl-6-isopropyl-1,4-dioxane-2,5-dione (isopropyl-substituted lactide), 4: 3-Methyl-6-butyl-1,4-dioxane-2,5-dione (butyl-substituted lactide), 5: 3-Methyl-6-hexyl-1,4-dioxane-2,5-dione (hexyl-substituted lactide), 5': 3,6-Dihexyl-1,4-dioxane-2,5-dione (symmetric dihexyl-substituted lactide), 6: 3-Methyl-6-phenylmethyl-1,4-dioxane-2,5-dione (benzyl-substituted lactide), 6': 3,6-Diphenylmethyl-1,4-dioxane-2,5-dione (symmetric dibenzyl-substituted lactide).

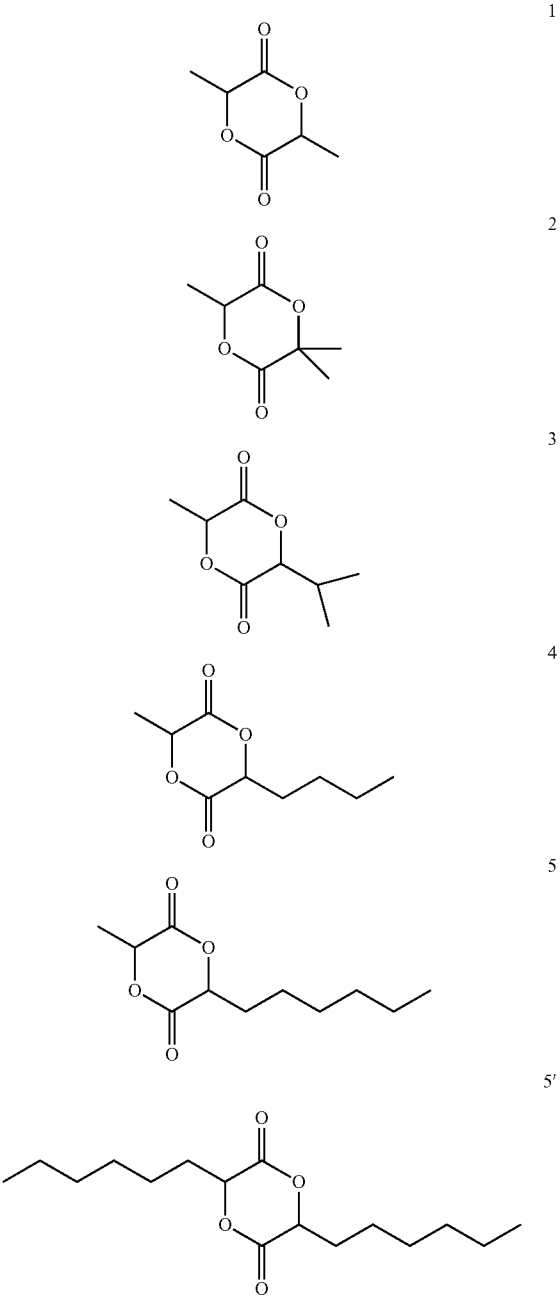

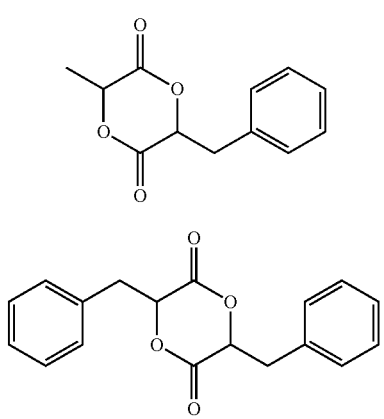

It is important to note that the focus of the above-referenced ROP method is to synthesize polymers with high melting points, which is contrary (i.e. the opposite of) the approach of the present invention (i.e., desired viscous polylactides). Further, Baker and Smith (2002) appear to only contemplate the use of metal organic catalysts; in contrast, the present invention can use solely an organic catalysts.

Their focus is herein on the synthesis and polymerization of the symmetric dialkyl-substituted lactides, but the patent includes also the possibility of polymerization of possible non-functional monoalkyl-substituted lactides. With emphasis on the synthesis of "poly(lactide)-based new materials with controlled properties" the inventors present here the synthesis and ROP of the mono-isopropyl (3), -butyl (4), -hexyl (5) and -benzyl (6)-substituted lactides, the dimethyl-substituted lactide (2) and the symmetric dihexyl-substituted lactide (5') (shown below), as well as their ring-opening polymerizations with the "standard" FDA-approved (Food Drug Admin, 1975) metal organic catalysts Sn(Oct)$_2$, with the more reactive "tin-based" tin(II)trifluoromethane sulfonate Sn(OTf)$_2$ Möller et al., 2000; Möller et al., 2001) and the solely organic catalyst 4-(dimethylamino)pyridine DMAP (Nederberg et al., 2001). The today accepted "coordination-insertion" mechanism for ROP of cyclic esters has been well established and described by Kowalski et al. (1998). Kricheldorf et al. (2000) and others for the most commonly used Sn(Oct)$_2$ catalyst. In this reaction mechanism Sn(Oct)$_2$ exchanges at least one of its 2-ethylhexanoate ligands with the initiating alcohol to form a tin alkoxide initiator. After monomer ring-opening leading to an alcohol ester end group the propagation proceeds through the tin alkoxide active centers. This mechanism also applies to the ROP used here for the polymerizations of the alkyl-substituted monomers catalyzed by Sn(Oct)$_2$, Sn(OTf)$_2$ and DMAP, respectively. The inventors utilized benzyl alcohol (BnOH) as the alcohol initiator, which enables later further functionalization of the polymers by deprotection of the benzyl end groups with H$_2$/Pd. When the steric more hindered monomers could not be efficiently polymerized with Sn(Oct)$_2$ and Sn(OTf)$_2$, the use of the DMAP catalyst was successfully applied. In most cases good control of molecular weight and narrow polydispersities were achieved for ROP of the new monoalkyl-substituted monomers leading to new functionalized poly(lactides).

Materials

α-hydroxyisobutyric acid, α-hydroxyisovaleric acid, 2-hydroxyoctanoic acid, D,L-3-phenyllactic acid, 2-bromopropionyl bromide were purchased from Fluka (Buchs, Switzerland), 2-hydroxyhexanoic acid and 2-bromopropionyl chloride from Sigma/Aldrich (Buchs, Switzerland). D,L-lactide from Purac Biochem (The Netherlands) was delivered under vacuum and directly transferred into a glove-box for storage. Tin(II) 2-ethylhexanoate (Sn(Oct)$_2$) was purchased from Aldrich and used as received. Tin(II)trifluoromethane sulfonate (Sn(OTf)$_2$, Aldrich) and 4-(dimethylamino)pyridine (DMAP, Fluka) were dried under vacuum at 80° C. prior to use. Benzyl alcohol (Fluka) was dried over calcium hydride and distilled prior to use.

Solvents were dried by standard methods and distilled prior to use. Anhydrous pyridine (Fluka) was stored over molecular sieve.

Monomer Synthesis 3,6,6-Trimethyl-1,4-dioxane-2,5-dione (2) (Referred as Dimethyl-Substituted Lactide)

5 g α-hydroxyisobutyric acid (48 mmol) and 5.15 mL 2-bromopropionyl chloride (50 mmol) were stirred at 75° C. under nitrogen for 12 h. 300 mL acetone and 14 mL anhydrous triethylamine (100 mmol) were added to the mixture and the solution was stirred for 3 h at 60° C. After filtration of the triethylammonium chloride salts, acetone was distilled off and the resulting mixture was dissolved in 450 mL ethyl acetate:hexane mixture (1:1). After filtration over silica gel the solvents were distilled off, and the remaining crude product was recrystallized from ethyl acetate:hexane mixture (1:10). $^1$H NMR (500 MHz, CDCl$_3$): δ 5.1 (q, 1H), 1.705 (s, 6H), 1.69 (d, 3H). $^{13}$C NMR (500 MHz, CDCl$_3$): δ 168.58, 166.64, 80.54, 72.90, 26.23, 25.27, 17.41. ELEM. ANAL. Calcd. for C$_7$H$_{10}$O$_4$: C, 53.16; H, 6.33. Found: C, 52.86; H, 6.39. Yield: 46%.

3-Methyl-6-isopropyl-1,4-dioxane-2,5-dione (3) (Isopropyl-Substituted Lactide)

5.1 g α-hydroxyisovaleric acid (43 mmol) and 4.85 mL 2-bromopropionyl bromide (45 mmol) were stirred at 75° C. under nitrogen for 12 h. 300 mL acetone and 12 mL anhydrous triethylamine (86 mmol) were added to the mixture and the solution was stirred for 3 h at 60° C. After filtration of the triethylammonium bromide salts, acetone was distilled off and the resulting mixture was dissolved in 500 mL ethyl acetate:hexane mixture (1:1). After filtration over silica gel the solvents were distilled off, and the remaining crude product was recrystallized from hexane. $^1$H NMR (500 MHz, CDCl$_3$): δ 5.0 (q, 1H), 4.76 (d, 1H), 2.5 (m, 1H), 1.66 (d, 3H), 1.16 (d, 3H), 1.06 (d, 3H). $^{13}$C NMR (500 MHz, CDCl$_3$): δ 167.59, 166.16, 79.83, 72.10, 29.24, 18.51, 15.86, 15.79. ELEM. ANAL. Calcd. for C$_8$H$_{12}$O$_4$: C, 55.81; H, 6.98. Found: C, 55.55; H, 6.99. Yield: 35%.

3-Methyl-6-butyl-1,4-dioxane-2,5-dione (4) (Butyl-Substituted Lactide)

2.5 g 2-hydroxyhexanoic acid (18.9 mmol) and 2.1 mL 2-bromopropionyl bromide (19.7 mmol) were stirred at 75° C. under nitrogen for 12 h. 150 mL acetone and 5.3 mL anhydrous triethylamine (38 mmol) were added to the mixture and the solution was stirred for 3 h at 60° C. After filtration of the triethylammonium bromide salts, acetone was distilled off and the resulting mixture was dissolved in 300 mL ethyl acetate:hexane mixture (1:2). After filtration over silica gel the solvents were distilled off, and the remaining crude product was recrystallized from hexane. $^1$H NMR (500 MHz, CDCl$_3$): δ 5.05 (q, 1H), 4.90 (dd, 1H), 1.9-2.15 (br m, 2H), 1.68 (d), 1.65 (d), (3H, of 2 diastereoisomers), 1.3-1.6 (br m, 4H), 0.93 (t, 3H). $^{13}$C NMR (500 MHz, CDCl$_3$): δ 167.54, 166.93, 166.25, 165.85, 75.79, 72.50, 72.24, 31.61, 29.70, 26.69, 26.42, 22.19, 21.97, 17.52, 15.81, 13.72, 13.66. ELEM. ANAL. Calcd. for C$_9$H$_{14}$O$_4$: C, 58.06; H, 7.53. Found: C, 57.62; H, 7.60. Yield: 40%.

3-Methyl-6-hexyl-1,4-dioxane-2,5-dione (5) (Hexyl-Substituted Lactide)

2.5 g 2-hydroxyoctanoic acid (15.6 mmol) and 1.75 mL 2-bromopropionyl bromide (16.3 mmol) were stirred at 80° C. under nitrogen for 12 h. 150 mL acetone and 4.35 mL anhydrous triethylamine (31 mmol) were added to the mixture and the solution was stirred for 3 h at 60° C. After filtration of the triethylammonium bromide salts, acetone was distilled off and the resulting mixture was dissolved in 250 mL ethyl acetate:hexane mixture (1:2). After filration over silica gel the solvents were distilled off, and the remaining crude product was recrystallized from hexane. $^1$H NMR (500 MHz, CDCl$_3$): δ 5.00 (q, 1H), 4.89 (dd, 1H), 1.9-2.15 (br m, 2H), 1.70 (d), 1.66 (d), (3H, of 2 diastereoisomers), 1.45-1.65 (br m, 2H), 1.25-1.40 (br m, 6H), 0.90 (t, 3H). $^{13}$C NMR (500 MHz, CDCl$_3$): δ 167.53, 166.90. 166.26, 165.87, 75.80, 72.49, 72.25, 31.92, 31.45, 31.39, 30.00, 28.73, 28.50, 24.60, 24.29, 22.48, 22.44, 17.54, 15.83, 14.00. ELEM. ANAL. Calcd. for C$_{11}$H$_{18}$O$_4$: C, 61.68; H, 8.41. Found: C, 61.63; H, 8.48. Yield: 45%.

3-6-Dihexyl-1,4-dioxane-2,5-dione (5') (Symmetric Hexyl-Substituted Lactide)

A mixture of 2 g 2-hydroxyoctanoic acid (12.5 mmol) and 0.24 g p-toluenesulfonic acid (1.25 mmol) in 200 mL toluene was heated at reflux for 24 h, and the forming water removed continuously by using a Dean-Stark apparatus. The toluene was distilled off and the resulting mixture was dissolved in 200 mL ethyl acetate:hexane mixture (1:2) and filtered over silica gel. After removal of the solvents the residue was dissolved in diethylether. The solution was washed with sodium hydrogen carbonate (saturated solution) and dried over MgSO$_4$. The product was recrystallized from diethylether. $^1$H NMR (500 MHz, CDCl$_3$): δ 4.90 (dd), 4.87 (dd), (1H, of 2 diastereoisomers), 1.9-2.15 (br m, 2H), 1.4-1.6 (br m, 2H), 1.2-1.4 (br m, 6H), 0.88 (t, 3H). $^{13}$C NMR (500 MHz, CDCl$_3$): δ 166.97, 165.83, 76.37, 75.58, 31.92, 31.37, 30.09, 28.70, 28.52, 24.47, 24.29, 22.43, 13.94. Yield: 65%.

3-Benzyl-6-methyl-1,4-dioxane-2,5-dione (6) (Benzyl-Substituted Lactide)

2.5 g D,L-3-phenyllactic acid (15 mmol) and 1.75 mL 2-bromopropionyl bromide (16.3 mmol) were stirred at 90° C. under nitrogen for 12 h. 150 mL acetone and 4.2 mL anhydrous triethylamine (30 mmol) were added to the mixture and the solution was stirred for 3 h at 60° C. After filtration of the salts, acetone was distilled off and the resulting mixture was dissolved in 250 mL ethyl acetate:hexane mixture (1:1). After filtration over silica gel the solvents were distilled off, and the remaining crude product was recrystallized from 1:1 ethyl acetate:hexane mixture. $^1$H NMR (500 MHz, CDCl$_3$): δ 7.25-7.4 (m, 5H), 5.30 (t) 5.10 (dd) (1H, of 2 diastereoisomers), 4.95 (q), 3.65 (q) (1H of 2 diastereoisomers), 3.48 (dd), 3.37 (dd), 3.24 (dd) (2H, of 2 diastereoisomers), 1.55 (d), 1.46 (d) (3H, of 2 diastereoisomers). $^{13}$C NMR (500 MHz, CDCl$_3$): δ 166.69, 166.07, 165.70, 165.50, 134.64, 130.03, 129.85, 129.32, 128.71, 127.49, 77.94, 76.63, 72.43, 71.96, 38.93, 36.36, 17.70, 16.01. ELEM. ANAL. Calcd. for C$_{12}$H$_{12}$O$_4$: C, 65.45; H, 5.45. Found: C, 65.34; H, 5.39. Yield: 35%.

2-(2-Bromo-1-oxopropoxy)octanoic acid (13)

2.5 g 2-hydroxyoctanoic acid (15.6 mmol) and 1.75 mL 2-bromopropionyl bromide (16.3 mmol) were stirred at 75° C. under nitrogen for 12 h. The obtained 2-(2-bromo-1-oxopropoxy)octanoic acid was purified by column chromatography and characterized by NMR. $^1$H NMR (500 MHz, CDCl$_3$): δ 5.08 (dd, 1H), 4.47 (q, 1H), 1.9-2.0 (m, 2H), 1.88 (d), 1.85 (d), (3H, of 2 diastereoisomers), 1.4-1.5 (m, 2H), 1.25-1.40 (br m, 6H), 0.90 (t, 3H). $^{13}$C NMR (500 MHz, CDCl$_3$): δ 176.10, 169.90, 72.82, 39.07, 31.50, 30.78, 28.60, 24.88, 22.47, 21.44, 14.00. Yield: 96%.

Preparation of Catalyst Stock Solutions

The catalysts for the ROP were used from stock solutions. A flask was heated under vacuum and after cooling to room temperature under protecting gas placed into a glove-box. The catalysts were weighed in and the flasks sealed with a septum. Dry THF and toluene were added afterwards under argon atmosphere. Stock solutions of Sn(Oct)$_2$ (in toluene/THF 3/2; 0.33 g/mL), Sn(OTf)$_2$ (in toluene/THF 1/1; 0.055 g/mL) and DMAP (in THF; 0.1 g/mL) were prepared.

General Procedure for Ring-Opening Polymerizations

Polymerizations were typically run with 2.3 mmol of monomer (~0.4 g). A reaction flask containing a stirbar was fitted with a septum, flamed under vacuum, and placed into a glove-box where the monomer was filled. The adequate solvent (2 mL) and catalyst (from stock solution, 1.5 mol % to monomer) were then added under argon atmosphere. After heating to a suitable temperature for solubilization of the reactants, benzyl alcohol as initiator alcohol was added as a 5-fold diluted solution in dry THF [40 µL, 0.076 mmol, for an expected degree of polymerization (DP) of 30], and the mixture was heated to the desired polymerization temperature.

At the desired reaction time, the reactions were stopped by adding 2 mL of THF, followed by precipitation in hexane, hexane/diethylether (1/1) and cold methanol, respectively. In order to remove remaining catalyst the polymer was finally washed with methanol and dried at 40° C. under vacuum. Polymerization conversions and DP were determined by $^1$H NMR analysis, and molecular weights and polydispersities determined by Gel Permeation Chromatography.

Measurements

The $^1$H NMR spectra were recorded in either deuterated chloroform or acetone-d$_6$ with a Bruker spectrometer (500 MHz). Gel Permeation Chromatography (GPC) was carried out on a Waters chromatographer, mounted with Styragel HR 1-4 columns (Waters) and connected to a Waters 410 differential refractometer. THF was the continuous phase and polystyrenes of known molecular weights: 500, 2630, 5970, 9100, 37900, 96400 g/mol (Tosoh Corporation) were used as calibration standards. Glass transition temperatures (T$_g$) were measured with a differential scanning calorimeter (SSC/5200, Seiko Instruments). Heating was performed under nitrogen at a flow rate of 5° C./min and the temperature was calibrated with an indium standard.

New Alkyl-Substituted Lactide Synthesis

The standard preparation method of symmetrical dialkyl-substituted lactides is the condensation reaction of the α-hydroxy acid, generally in acidic conditions and removing of the water formed during the reaction (Yin and Baker, 1999; Deane and Hammond, 1960). For the synthesis of the unsymmetrical monoalkyl-substituted lactides, dimethyl-2, isopropyl-3, butyl-4, hexyl-5 and benzyl-6 substituted lactide, the inventors chose a simple two-step one-pot synthesis, based on the analogue reaction described by Schöllkopf et al. (1979). Dialkyl-, and mixed substituted lactides can be prepared by the same method, by choosing accordingly the substituents $R^1$, $R^2$, $R^3$ and $R^4$, as outlined above.

The α-hydroxy acid 7, bringing in the alkyl-substituent in the desired lactide ring, leads under reaction (i) with an α-bromo alkanoyl bromide 8 to the intermediate ester 9, as shown in Scheme 1. The ring closure to the lactide 10 is obtained in a second step (ii) under basic reaction reactions conditions with triethylamine ($Et_3N$). This one-pot synthesis has proven to be quite versatile, being easily performed and based on relative cheap starting materials. The proceeding of the reaction, quantitatively formation of the intermediate ester 9 along with the fully consumption of the initial α-hydroxy acid 7, can be monitored by Thin Layer Chromatography (TLC). By this method the new isopropyl-3, butyl-4, and hexyl-6 substituted lactides were synthesized. To the inventors' knowledge these lactides have not been described in the literature so far, but are mentioned as possible non-functional alkyl-substituted lactides in the patent of Baker and Smith (2002). The monobenzyl-substituted lactide 6 was synthesized by Schöllkopf et al. before and Bolte et al. determined the crystal structure of this compound (Bolte et al., 1994), but both have not described any polymerization reactions with this potential monomer. The synthesis of the dimethyl-substituted lactide 2 and its polymerization is reported by Baker and Smith (2002) and Chisholm et al. (2003). For the inventors' studies both substituted lactides 2 and 6 were prepared by the general two-step one-pot method. The more steric-hindered dimethyl-substituted lactide 2 was used here as a "difficult" polymerizable monomer for in general comparison with the polymerization reactions of the new substituted lactides and for the investigation of ROP with $Sn(Oct)_2$, and the more reactive catalysts $Sn(OTf)_2$ and DMAP, respectively. As a typical example for the synthesis of monoalkyl-substituted lactides the inventors describe here the synthesis of the monohexyl-substituted lactide 5 in more detail. As illustrated in Scheme 2 in the first reaction step (i) 2-hydroxy-octanoic acid 11 and 2-bromopropionyl bromide 12 are simply mixed and stirred at 75° C. under nitrogen for 12 h forming the ester 2-(2-bromo-1-oxopropoxy)octanoic acid 13. Control by TLC ($CH_2Cl_2$:MeOH:$CH_3COOH$ 10:0.1:0.1 eluent mixture, $R_f$: 0.45) showed no remaining initial hydroxy acid reactant ($R_f$: 0.15). The second reaction step (ii), ring closure to the desired lactide, can be done directly in the same pot. Acetone is added for better solubility and under the basic reaction conditions with triethylamine ($Et_3N$) 3-methyl-6-hexyl-1,4-dioxane-2,5-dione 5 is formed while stirring for 3 h at 60° C. Purification by filtration of the salts and recrystallization from ethyl acetate:hexane mixtures yields the final lactide product 5, which after drying is ready for ring-opening polymerization. In a further control experiment the ester 13 was prepared by the same first reaction step, the reaction stopped after the same time and after purification the ester 2-(2-bromo-1-oxopropoxy)octanoic acid 13 was characterized by NMR proving its structure and quantitative formation. The yields obtained for the different alkyl-substituted lactides are of about 40-50%, showing the limiting step for this synthesis method is the formation of the lactide ring. Further optimization of the second reaction step (ii) of the presented one-pot synthesis could be achieved by applying any dissolution technique. Despite the two asymmetric α-carbon atoms in the lactide ring and the non-stereoselective reaction conditions the lactide 3 was obtained as one major diastereomer, whereas the alkyl-substituted lactides 4 and 5 were obtained in a 2:1 mixture, the benzyl-substituted lactide 6 in a 8.5:1.5 mixture of diastereomers after the single purification step by recrystallization. For the initial studies of ring-opening polymerizations of these new lactides all monomers were used in the described diastereomer mixtures. TLC tests of the monoalkyl-substituted lactides and the work-up by column chromatography of the hexyl-substituted lactide 5 have shown that a separation of the lactide diastereomers is possible. This is of interest since it is known that the stereochemistry has a tremendous impact on the poly(lactide) properties. Thus this also applies for the overall tailoring of the material properties of the new poly(alkyl-substituted lactides) and their possible copolymers in all stereochemical combinations.

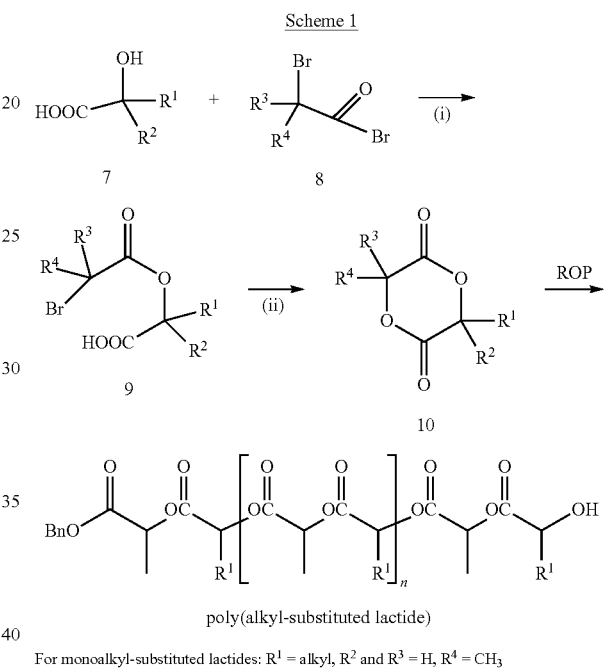

Scheme 1

For monoalkyl-substituted lactides: $R^1$ = alkyl, $R^2$ and $R^3$ = H, $R^4$ = $CH_3$

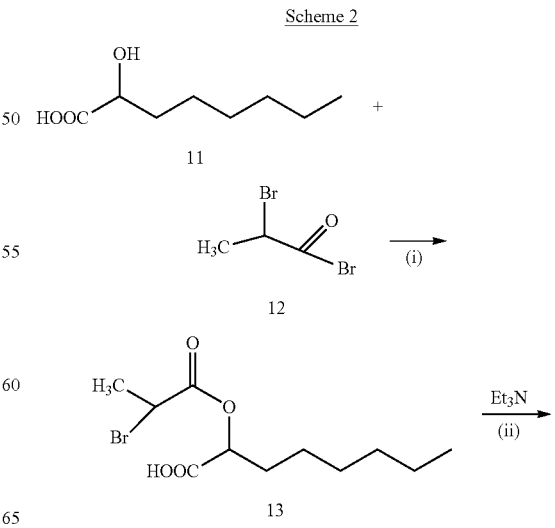

Scheme 2

-continued

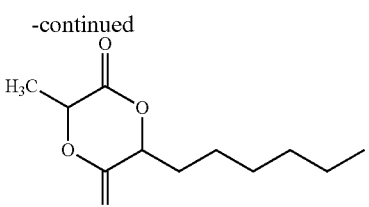

5

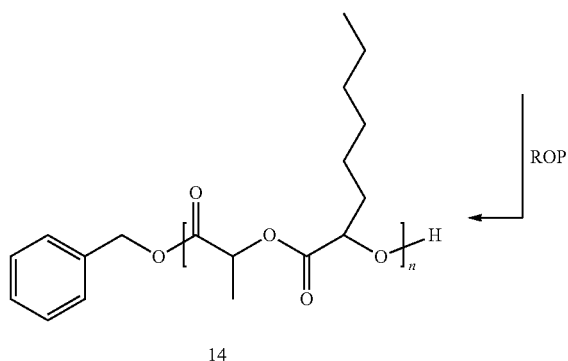

14

Ring-Opening Polymerizations

The controlled ROP of D,L-lactide in presence of metal catalysts is a very well known reaction. Especially $Sn(Oct)_2$ is an outstanding catalyst for ROP of lactides, not only because of its good polymerization properties, but also because of its FDA approval it has a major advantage for the synthesis of poly(lactides) for medical applications (Kricheldorf et al., 1995; Hyon et al., 1997; Schwach et al., 1997; Degee et al., 1999). The classical method is $Sn(Oct)_2$ catalyzed polymerization of lactide in bulk, with or without an alcohol initiator, at relative high temperatures (>120° C.). Due to these reaction conditions side reactions, e.g. transesterifications, decrease the control of molecular weight and polydispersity. For the controlled synthesis of poly(lactides) in general and also for the inventors' new poly(alkyl-substituted lactides) for biomedical applications the inventors intended to polymerize at lower reaction temperatures (<110° C.) in order to achieve best control of the polymer properties. Benzyl alcohol was chosen as the initiator alcohol for different reasons: a) its low volatility for the standard reactions at around 100° C., b) with the benzyl $^1H$ NMR signal at 7.4 ppm determination of conversions and degrees of polymerization (DP) is possible for all the studied alkyl-substituted monomers and polymers, and c) the $H_2$/Pd reduction of the resulting benzylester end group is giving reactive carboxylic acid end groups suitable for further functionalizations of the polymers. For the initial studies and comparisons of the different new monomers all polymerizations were targeted for a degree of polymerization of DP=30, which also enables easy characterization via end group analysis by $^1H$ NMR. The $Sn(Oct)_2$ catalyst was used in relatively large amounts to favour reasonable polymerization rates (1.5 mol % with respect to the monomer) but maintained in presence of excess of initiating alcohol ([BnOH]/[Sn(Oct)$_2$]~2, [M]/[BnOH]~30), since it has been proven that the polymerization rate is only dependent on the catalyst concentration, provided that [ROH]/[SnOct$_2$]>2 (Kowalski et al., 1998; Kricheldorf et al., 2000).

ROP of Monohexyl-Substituted Lactide 5 with $Sn(Oct)_2$

The synthesis of the dimethyl 2, isopropyl 3, butyl 4, hexyl 5 and 5', and benzyl 6-substituted lactides was followed by ROP of these monomers. The different alkyl chain lengths of the substituents are expected to influence the hydrophobicity/philicity and degradability of the obtained polymers and thus to allow to modulate the poly(lactide) properties. For a first feasibility study, the hexyl-substituted lactide 5 was polymerized under standard reaction conditions with $Sn(Oct)_2$ in comparison with D,L-lactide 1. These results are presented in Table 1. The polymerization of the hexyl-substituted lactide 5 was first run at 60° C., in solvent-free mild reaction conditions, taking advantage of the low melting point of this monomer. The conversion was determined by $^1H$ NMR as described in FIGS. 2A-B on the crude reaction mixture, using the methine proton peak integrals of both polymer 14 and monomer 5. Since the conversion was only 13% after 1 hour and 25% after 5 h, polymerizations were then run at a higher temperature (100° C.). By this a conversion of 83% was reached after 1 h. After 4 h reaction time the conversion increased to 90% and the molecular weight distribution was still narrow ($M_w/M_n$=1.13). However, a prolonged reaction time (24 h) led to a broader distribution due to transesterification side reactions ($M_w/M_n$=1.44). Replacing the methyl group of this monomer by another hexyl substituent (symmetric hexyl-substituted lactide 5') did not significantly affect the polymerization rate since a similar conversion of 81% (instead of 83% for 5) was found after 1 h. Polymerizations with D,L-lactide 1 in similar conditions (in toluene at 60° C. and in toluene/bulk at 100/110° C.) were carried out as controls. Conversions were determined by $^1H$ NMR analysis on the crude reaction mixture by using the methine peak integrals of both polymer and monomer (methine proton at 5.4 ppm for the monomer, 5.2 ppm for the polymer in acetone-$d_6$). The conversions were higher than those obtained for the hexyl-substituted monomer 5, particularly for low temperatures. These results evidence that the steric hindrance of the hexyl group has a direct influence on the polymerization rate. It must be noticed that the MW distribution is narrower for the hexyl monomer ($M_w/M_n$=1.13) than for the D,L-lactide melt-polymerized (1.26). This might be due to the low viscosity in the hexyl-substituted lactide reaction mixture observed during and still at the end of the ROP compared to the D,L-lactide polymerization, where a possible loss of polymerization control occurs near complete conversion. The obtained polymers showed DP values close to those expected from the monomer to initiator ratio (corrected with the conversion value), which is consistent with a living-polymerization process.

TABLE 1

| Monomer | ROP conditions | Time (h) | Conversion ($^1H$ NMR) | DP Targeted[a] | DP Measured[b] | $M_n$ (g/mol) | $M_w/M_n$ | $T_g$ (° C.) |
|---|---|---|---|---|---|---|---|---|
| 5 | Bulk 60° C. | 1 | 13 | 30 | 4 | — | — | |
| 5 | Bulk 60° C. | 5 | 25 | 30 | 8 | — | — | |
| 1 | Tol. 60° C. | 1 | 30 | 30 | 6 | 1160 | 1.16 | |
| 1 | Tol. 60° C. | 5 | 63 | 30 | 20 | 3350 | 1.12 | |
| 5 | Bulk 100° C. | 1 | 83 | 30 | 26 | 4450 | 1.13 | |

TABLE 1-continued

| Monomer | ROP conditions | Time (h) | Conversion ($^1$H NMR) | DP Targeted[a] | DP Measured[b] | $M_n$ (g/mol) | $M_w/M_n$ | $T_g$ (° C.) |
|---|---|---|---|---|---|---|---|---|
| 5 | Bulk 100° C. | 5 | 90 | 30 | 29 | 4650 | 1.13 | −17 |
| 5 | Bulk 100° C. | 24 | 92 | 30 | 30 | 4530 | 1.44 | |
| 5' | Bulk 100° C. | 1 | 81 | 28 | 22 | 5600 | 1.09 | −47 |
| 1 | Tol. 100° C. | 1 | 90 | 30 | 25 | 4020 | 1.07 | +41 |
| 1 | Bulk 110° C. | 1 | 90 | 30 | 26 | 4000 | 1.26 | |

[a]corrected DP target after determination by $^1$H NMR on the crude polymer mixture.
[b]determined by $^1$H NMR on the precipitated product.

$^1$H NMR was used to confirm the structure of the poly(hexyl-substituted lactide) 14 obtained after precipitation in MeOH. Both benzylester and —C<u>H</u>—OH end groups can be identified, confirming the initiation by the benzyl alcohol. The methylene protons of the benzyl alcohol are overlapped by the methine protons of the polymer chain at 5-5.25 ppm. The spectrum clearly showed that the alcohol end groups are of two types: a (q) CH3-C<u>H</u>—OH, 45% and b (dd) hexyl-C<u>H</u>—OH, 55% (calculated from integration). This result shows that the propagation proceeds by the "alcoholate" attack in nearly equal measure on both kinds of carbonyl atoms in the substituted lactide ring with a slight preference for the less hindered one. This result is also consistent with the fact that a second substitution of the remaining methyl group of 5 by another hexyl group, giving the symmetrical hexyl-substituted lactide 5', did not induce a significant decrease of the conversion (81% and 83% for 5' and 5, respectively, after 1 h), under the same reaction conditions.

As demonstrated, the monohexyl-substituted lactide 5 could be successfully polymerized with Sn(Oct)$_2$ in relative high yields under convenient reaction conditions (100° C., 1 h). Glass transition temperatures ($T_g$) were determined for the polylactides of D,L-lactide 1, monohexyl-substituted lactide 5 and symmetric dihexyl-substituted lactide 5' with comparable molecular weights (4000-5500 g/mol) and molecular weight distributions ($M_w/M_n$~1.10). Interestingly, the glass transition temperature decreased from $T_g$=41° C. for standard poly(D,L-lactide) to $T_g$=−17° C. for the poly(monohexyl-substituted lactide) 14 and $T_g$=−47° C. for the poly(dihexyl-substituted lactide), showing that the physical properties of the polymers could be modulated by the introduction of controlled amounts of hydrophobic moieties. $T_g$ values measured for poly(D,L-lactide) and poly(dihexyl-substituted lactide) were in a good accordance to those previously reported in the literature: Jamshidi et al. (1988) obtained a $T_g$≈37° C. for a poly(D,L-lactide) of 3470 g/mol, and Yin and Baker (1999) reported a $T_g$≈−37° C. for their poly(dihexyl-substituted lactide). For the latter value it is to point out that the molecular weight was much higher (43000 g/mol) than the one tested in the inventors' study (5600 g/mol).

ROP of Monoalkyl-Substituted Lactides 2, 3, 4 and 6

With regards to the previous results on the monohexyl-substituted lactide 5, Sn(Oct)$_2$-catalyzed polymerizations of the other dimethyl-2, isopropyl-3, butyl-4 and benzyl-6 substituted lactides were investigated at 100° C. for 1 h, and the obtained results are presented in Table 2. Conversions were determined as described above by $^1$H NMR analysis. All monomers could be polymerized with reasonable conversions (from 62 to 87%) except for the dimethyl-substituted monomer 2 (22% even after 18 h). All alkyl-substituted polymers showed relative narrow MW distributions ($M_w/M_n$<1.2). Interestingly these MW distributions were even narrower than those obtained for D,L-lactide 1. Molecular weights obtained and determined by GPC were in good accordance with the DP determined by $^1$H NMR. Moreover the obtained DP were in relatively good correlation with the aimed values (conversion*M/I) for the polymers.

TABLE 2

| Monomer | Catalyst | ROP conditions | Time (h) | Conversion ($^1$H NMR) | DP Targeted[a] | DP Measured[b] | $M_n$ (g/mol) | $M_w/M_n$ |
|---|---|---|---|---|---|---|---|---|
| 1 | Sn(Oct)$_2$ | Bulk 110° C. | 1 | 90 | 30 | 26 | 4000 | 1.26 |
| 2 | " | Bulk 100° C. | 18 | 22 | 29 | 7 | 1120 | 1.29 |
| 3 | " | Bulk 100° C. | 1 | 62 | 26 | 16 | 2000 | 1.18 |
| 4 | " | Bulk 100° C. | 1 | 87 | 26 | 20 | 3850 | 1.22 |
| 5 | " | Bulk 100° C. | 1 | 83 | 30 | 26 | 4450 | 1.13 |
| 6 | " | Tol. 100° C. | 1 | 79 | 26 | n.d.[c] | 3100 | 1.14 |

[a]corrected DP target after determination by $^1$H NMR on the crude polymer mixture.
[b]determined by $^1$H NMR on the precipitated product.
[c]not determinable by $^1$H NMR from benzyl end groups, because of overlapping signals.

The found conversions were correlative with the chain length of the alkyl substituents of the monomers. The conversions decreased from 90 to 87 and 83% with the increasing in the chain length of the methyl-1, butyl-4 and hexyl-5 substituent, respectively. Branched alkyl-substituted monomers were less good polymerizable. The conversion of the isopropyl derivative 3 decreased to 62% under the same reaction conditions, and dramatically decreased to only 22% for the double methyl-substituted lactide 2 even after a prolonged reaction time of 18 h. The benzylic derivative 6 was polymerizable with a good conversion of 79% within 1 h. Due to the melting point of 6 (mp>100° C.), the ROP was carried out in toluene. The steric hindrance by a benzyl or an isopropyl group on the monomer did not compromise the polymerizability with the Sn(Oct)$_2$ catalyst. In contrast the di-substitution of the α-carbon of the monomer by two methyl groups (dimethyl-substituted lactide 2) had a dramatic negative effect on the polymerization rate. Baker and Smith (2002) reported the difficulty to polymerize this monomer with Sn(Oct)$_2$. They had to use a very high polmerization temperature (180° C.) to obtain a decent conversion (75%) after 24 h. Except for this particular case of the disubstituted monomer 2, Sn(Oct)$_2$ has been proven to be relatively efficient in polymerizing the differently steric-hindered monomers (conversions of 65-85%) in short reaction times. Nevertheless more reactive catalysts were investigated, on the one hand to favor higher conversion rates for the more hindered monomers, as the dimethyl 2 and isopropyl 3 ones, and on the other hand to achieve even higher yields for the other new monomers at mild polymerization conditions, and also with a view to the potential scale-up of the reaction.

ROP with Sn(OTf)$_2$ and DMAP Catalysts

Sn(OTf)$_2$ was previously reported by Möller et al. (2000); Möller et al., 2001) as a very efficient and versatile catalyst for ROP of various lactides and lactones, compared to other tin-based catalysts as Sn(Oct)$_2$ or dibutyltin(II)-2-ethylhexanoate Bu$_2$Sn(Oct)$_2$. Polymerizations were carried out with the Sn(OTf)$_2$ catalyst for the more hindered dimethyl substituted lactide 2 under the same conditions as those used for the Sn(Oct)$_2$ polymerizations (1.5 mol % of catalyst to monomer, 100° C.). As a control polymerizations with the D,L-lactide 1 were performed. The results are shown in Table 3. The triflate catalyst showed a slight increase in the polymerization rate of the dimethyl-substituted lactide 2 in the reactions either in bulk or in pyridine (30% and 27%, respectively, after 18 h), compared to Sn(Oct)$_2$ (22% conversion after 18 h, Table 2). Pyridine was used since it was shown that Sn(OTf)$_2$ is a very efficient catalyst for ROP in this solvent. Indeed, for the D,L-lactide control reactions the conversion is only about 30% after 1.5 h with Sn(Oct)$_2$ as catalyst, whereas it is 70% with Sn(OTf)$_2$ (Table 3). However, bulk or toluene conditions are not preferable here for the tin-triflate catalyst, since only 77% and 10% conversion are obtained after 1.5 h reaction time, in comparison to 90% conversion with Sn(Oct)$_2$ in both conditions after 1 h (Table 1). This might be due to the poor solubility of the Sn(OTf)$_2$ catalyst in molten mixture or in toluene, hence the typical conditions the inventors used for the polymerizations at 100° C., in bulk or toluene, are not really adequate for this catalyst to show its efficiency. Therefore the catalyst was changed from Sn(OTf)$_2$ to 4-(dimethylamino)pyridine (DMAP), which was recently reported by Nederberg et al. (2001) as an efficient organic catalyst for lactide polymerization. Same bulk polymerization conditions as used before for Sn(Oct)$_2$ were applied. Used in the same concentration as Sn(Oct)$_2$ and Sn(OTf)$_2$ (1.5%/monomer i.e BnOH/DMAP=2), the DMAP catalyst was found to be more reactive (Table 4). The conversion for the dimethyl-substituted lactide 2 was already 30% after only 5 h of polymerization, whereas it was 22% with Sn(Oct)$_2$ (Table 2) and 30% with Sn(OTf)$_2$ (Table 3) after a reaction time of 18 h. After 24 h the conversion reached 65%, showing a good control of molecular weight and distribution ($M_w/M_n$=1.26). In comparison the D,L-lactide 1 conversion is already 78% after only 0.6 h. To enhance the polymerization rate further polymerizations were run with a higher amount of DMAP (2 equivalents of DMAP/BnOH), a catalyst concentration typically used in previous studies Nederberg et al. (2001). As a result the conversion for 2 was then 35% after only 1 h. Also the other alkyl-substituted lactides of both linear type, hexyl-substituted lactide 5, and non-linear type, isopropyl- and benzyl-substituted lactides 3 and 6, were polymerized with this higher catalyst concentration for DMAP. The conversions reached now excellent 80%, 97%, and 95% for 3, 5 and 6 after a reaction time of only 1 h. Polymers of higher DP could be obtained (e.g. hexyl-substituted lactide 5, DP=41), requiring however a longer reaction time for good conversion (2 h and 5 h for 59% and 90% conversion, respectively). This can be explained by the higher viscosity of the reaction mixture observed at conversions above 60%. DMAP is also efficient at a lower polymerization temperature. 60% conversion could be obtained within 18 h for the benzyl-substituted lactide 6 by carrying out the polymerization at 60° C. in THF. This is an interesting result, since this solvent was generally reported to be not preferable for ROP of lactides with tin-based catalysts (Simmons and Baker, 2001).

TABLE 3

| Monomer | Catalyst | ROP conditions | Time (h) | Conversion ($^1$H NMR) | DP Targeted[a] | DP Measured[b] | $M_n$ (g/mol) | $M_w/M_n$ |
|---|---|---|---|---|---|---|---|---|
| 2 | Sn(OTf)$_2$ | Bulk 100° C. | 18 | 30 | 26 | 6 | 850 | 1.20 |
| 2 | " | Pyr. 100° C. | 3 | 0 | 26 | — | — | — |
| 2 | " | Pyr. 100° C. | 18 | 27 | 26 | 6 | 850 | 1.25 |
| 1 | " | Bulk 110° C. | 1.5 | 77 | 30 | 25 | 4200 | 1.22 |
| 1 | " | Pyr. 100° C. | 1.5 | 70 | 30 | 18 | 2900 | 1.23 |
| 1 | Sn(Oct)$_2$ | Pyr. 100° C. | 1.5 | 30 | 30 | n.d[c] | —[c] | —[c] |
| 1 | Sn(OTf)$_2$ | Tol. 100° C. | 1.5 | 10 | 30 | —[c] | —[c] | —[c] |

[a]corrected DP target after determination by $^1$H NMR on the crude polymer mixture.
[b]determined by $^1$H NMR on the precipitated product.
[c]not determined after 1.5 h reaction time, polymerization was continued.

TABLE 4

| Monomer | BnOH/DMAP ratio | ROP conditions | Time (h) | Conversion ($^1$H NMR) | DP Targeted[a] | DP Measured[b] | $M_n$ (g/mol) | $M_w/M_n$ |
|---|---|---|---|---|---|---|---|---|
| 2 | 2 | Bulk 100° C. | 5 | 30 | 27 | 8 | 1410 | 1.19 |
| 2 | 2 | " | 24 | 65 | 27 | 21 | 2600 | 1.26 |
| 2 | 0.5 | " | 1 | 35 | 27 | n.d.[c] | —[c] | —[c] |
| 2 | 0.25 | " | 5 | 75 | 27 | 22 | 2100 | 1.35 |
| 3 | 0.5 | Bulk 100° C. | 1 | 80 | 26 | 20 | 3450 | 1.15 |
| 5 | 0.5 | Bulk 100° C. | 1 | 97 | 29 | 24 | 5400 | 1.10 |
| 5 | 0.5 | " | 2 | 59 | 45 | 26 | 5400 | 1.09 |
| 5 | 0.5 | " | 5 | 90 | 45 | 41 | 7600 | 1.19 |

TABLE 4-continued

| Monomer | BnOH/DMAP ratio | ROP conditions | Time (h) | Conversion ($^1$H NMR) | DP Targeted[a] | DP Measured[b] | $M_n$ (g/mol) | $M_w/M_n$ |
|---|---|---|---|---|---|---|---|---|
| 6 | 0.5 | Bulk 100° C. | 1 | 95 | 27 | n.d.[d] | 3000 | 1.20 |
| 6 | 0.5 | THF 60° C. | 18 | 60 | 27 | n.d.[d] | 2600 | 1.20 |
| 1 | 2 | Bulk 110° C. | 0.6 | 78 | 31 | 26 | 4050 | 1.18 |
| 1 | 0.5 | " | 0.6 | 92 | 30 | 25 | 3200 | 1.36 |
| 1 | 0.5 | " | 1 | 99 | 30 | 31 | 3900 | 1.48 |

[a]corrected DP target after determination by $^1$H NMR on the crude polymer mixture.
[b]determined by $^1$H NMR on the precipitated product.
[c]not determined after 1.5 h reaction time, polymerization was continued
[d]not determinable by $^1$H NMR from benzyl end groups, because of overlapping signals.

Again the molecular weight distribution was much narrower for the substituted lactides ($M_w/M_n$=1.10-1.20) than for D,L-lactide (1.48). Since D,L-lactide is the more reactive monomer, probably more transesterification side reactions occur to the end of the polymerization at high conversion. However, these undesirable side reactions were reported not to occur even after a prolonged time of polymerization (no polydispersity increase) with the DMAP catalyst at low temperatures (35° C.) (Nederberg et al., 2001). Thus DMAP polymerization could be run to completion at milder reaction conditions to obtain optimal yields. DP and $M_n$ obtained for the new substituted lactides were close to those expected from the theory, consistent with a good polymerization control. The increased concentration of DMAP (4 eq. to BnOH) allowed further enhancement of the polymerization rate. Here a conversion of 75% could be obtained for the dimethyl-substituted monomer 2 within only 5 h. However, in this last case the molecular weight is lower than the desired one and the polydispersity increases from 1.26 to 1.35. Further studies on optimization of these DMAP-catalyzed ROP of alkyl-substituted lactides will be carried out. Finally it is to point out that the DMAP catalyst was efficiently removed from the polymers during the precipitation in MeOH, no traces of DMAP were observed on $^1$H NMR polymer spectra. Therefore this organic catalyst appears to be a promising versatile catalyst for ROP of steric-hindered and substituted lactides by enabling polymerizations at mild temperatures and thus favoring the synthesis of narrowly dispersed new poly(alkyl-substituted lactides).

The inventors report here a versatile approach for the synthesis and the polymerization of new monoalkyl-substituted lactide monomers. The new monomers can easily be obtained by a two-step-one-pot synthesis, and can be polymerized by ROP with Sn(Oct)$_2$, Sn(OTf)$_2$ and DMAP as catalysts. By the introduction of alkyl substituents the polymerizability of the monomers was as expected in accordance with their steric hindrance. Nevertheless Sn(Oct)$_2$ was applied successfully for the ROP of the different substituted lactides at 100° C., and all polymers are showing narrow molecular weight distributions ($M_w/M_n$=1.1-1.2) and conversions of 65-85% within 1 hour. Only the dimethyl-substituted lactide 2 was hardly polymerizable even after prolonged reaction times (22% conversion after 18 h). The polymerizations rates of the alkyl-substituted lactides could be increased by using either Sn(OTf)$_2$ or DMAP as ROP catalysts. Particularly with the latter one a conversion of about 70% could be reached for the dimethyl-substituted lactide 2 within in a decent polymerization time of 24 h, and conversions of about 90% in 1 h were obtained for the other substituted new lactides. The efficiency of this catalyst for ROP opens doors to the potential design of new functionalized lactides in a large variety, in respect to the possible variations of the alkyl substitutents $R^1$, $R^2$, $R^3$ and $R^4$, respectively in the two basic starting compounds 7 and 8 (Scheme 1). These new lactide based monomers and reactive ROP catalysts are a promising approach for the controlled synthesis of tailored materials and its applications e.g. in the medical field. By adjusting different parameters such as the substituents on the lactide monomers, polymer molecular weight or the combination and incorporation in copolymers with established poly(lactides) and poly(lactide-co-glycolides) important properties like polymer hydrophilicity/-phobicity and biodegradability can be suited to the specific application.

Example 2

Synthesis and Properties of Novel Poly(Hexyl-Substituted Lactides) for Pharmaceutical Applications Biocompatible and biodegradable polylactides/glycolides (PLA/PLGA) have received high attention over the last thirty years in the biomedical field as sutures, implants, colloidal drug delivery systems (Penning et al., 1993; Uhrich et al., 1999), and more recently also in tissue repairing and engineering (Liu and Ma, 2004; Stock and Mayer, 2001) and anti-cancer drug delivery (Mu and Feng, 2003; Jiang et al., 2005). Next to the medical field they are also widely used in the packaging area. As biodegradable "green polymers" they are preferable to the commodity polymers currently used (Drumright et al., 2000; Vink et al., 2003). There is a crucial need of well-defined polylactide-based materials with advanced properties to fit all the requirements for the different applications. For example, PLA/PLGA homo- and co-polymers synthesized by the well-established ring opening polymerization (ROP) process (Dechy-Cabaret et al., 2004; Kricheldorf et al., 1995; Schwach et al., 1997; Degee et al., 1999; Ryner et al., 2001) have a glass transition temperature ($T_g$) limited to a range of only 40-60° C. (Jamshidi et al., 1988; Vert et al., 1984), independent of the polymer molecular weight and chemical composition. This combined with interesting mechanical properties makes them suitable in medical applications as biodegradable implants, bone fracture fixation devices, scaffolds for living cells. However for drug delivery purposes, they need to be formulated with organic solvents and administered as solutions or in form of nano- and micro-particles, they can not be injected on their own. This strategy for novel PLAs with tailored properties is based on the substitution of a methyl ligand on the lactide monomer by other alkyl substituents (Trimaille et al., 2004). The introduction of alkyl-side groups is expected to strongly affect material properties such as the $T_g$ and viscosity. For pharmaceutical applications further important properties such as degradation rate and profile or drug encapsulation and release will be modified.

Increasing attention was recently put on injectable polymers as promising alternatives to emulsions, liposomes or microsphere drug delivery systems (Amsden et al., 2004; Hatefi and Amsden, 2002; Merkli et al., 1994). Next to other alkyl-substituted lactides the inventors reported the synthesis and characterization of the novel poly(monohexyl-substituted lactide) (PmHLA), which was shown to have a low glass transition temperature ($T_g = -17°$ C.) compared to a standard PLA (Tg=41° C.) with the analogue molecular weight (4500 g/mol) (Trimaille et al., 2004). Based on these initial results this hydrophobic hexyl-substituted polylactide could be favourable and interesting for applications as an injectable PLA drug delivery system comparable to the reported semi-solid hydrophobic poly(ortho esters) (Schwach-Abdellaoui et al., 2001). The used ring-opening polymerization technique with its living character and functional end groups gives the opportunity to synthesize various new PLA-based copolymers in combination with the established PLA/PLGA systems. By this different functional PLAs with tailored material properties for biomedical applications can be easily obtained.

The inventors present here a detailed study on the synthesis and controlled ROP of these novel hexyl-substituted polylactides, as well as their physico-chemical properties in terms of $T_g$ and rheological behaviour and degradation kinetics and mechanism.

Materials

All materials here were prepared as described in EXAMPLE 1

Monomer Synthesis

All synthesized monomers were prepared as described in EXAMPLE 1

Polymer Synthesis and Characterization

All synthesized polymers were prepared and characterized as described in EXAMPLE 1

Thermal Analysis

Glass transition temperatures ($T_g$) were measured with a differential scanning calorimeter (SSC/5200, Seiko Instruments). Heating was performed at a flow rate of 5° C./min and the temperature was calibrated with an indium standard.

Viscosity Determination

Viscosities were determined using a Bohlin controlled stress rheometer with a parallel plate PU 20 device (Bohlin Rheology GmbH, Mühlacker, Germany). A stress viscosity test (rotation) was applied to the samples which were placed on the stationary lower plate. The temperature was fixed at 25° C. or 37° C. during the test with a Bohlin Extended Temperature Option (ETO). Shear rates ranging from 0.1 to 400 $s^{-1}$ were used for determination. For all samples an integration time of 20 s and a delay time of 20 s were used.

Degradation Studies 40 mg of polymer were placed into flasks and gently heated to be above the $T_g$ of the polymers. 5 mL of 0.1M phosphate buffer pH 7.4 were then added and the flasks slowly agitated at the adequate temperature. At predetermined times polymers were collected, rinsed with milli-Q water and dried to constant weight prior to determination of mass loss and average molecular weight.

Mass loss (ML %) was evaluated by gravimetric analysis and calculated from:

$$ML \% = \frac{100(W_0 - W_t)}{W_0}$$

Where $W_0$ and $W_t$ are the initial weight and residual weight of the dry polymer at time t.

Molecular weights were determined by GPC by dissolving the polymer in THF as described above.

Monomer Synthesis and Controlled ROP

In the inventors' previous work the inventors reported the synthesis and ring-opening polymerization of novel alkyl-substituted lactide monomers for the design of new tailored polylactide materials (Trimaille et al., 2004). Here the inventors focus on the poly(monohexyl-substituted lactide) (PmHLA 5) which was obtained by the synthesis pathway presented in Scheme 3. The synthesis of the new monohexyl-substituted lactide (mHLA 4) is based on a "two step one pot" reaction of 2-hydroxyoctanoic acid 2, easily synthesized in large scale from heptanal 1, with 2-bromopropionyl bromide leading to an intermediate ester 3, which undergoes ring-closing after changing to basic reaction conditions with triethylamine. This latter intramolecular cyclization is found to be the limiting step of the process with a yield of 45%, despite the dropwise addition of the intermediate 3 into the very dilute basic solution to favor the ring-closing. After recrystallization the mHLA was obtained as a mixture of the two diastereomers (ratio 2/1) which can be easily separated by gel chromatography. This offers interesting perspectives for the properties of the hexyl-substituted polylactides obtained from the diastereomerically pure monomers by ROP, considering the great impact of the stereochemistry on the physico-chemical characteristics of the polymer materials (Tsuji et al., 1991). In the present work the inventors investigated the diastereomeric mixture of the monomer for comparison of the obtained polymer properties with those of the amorphous poly(D,L-lactide).

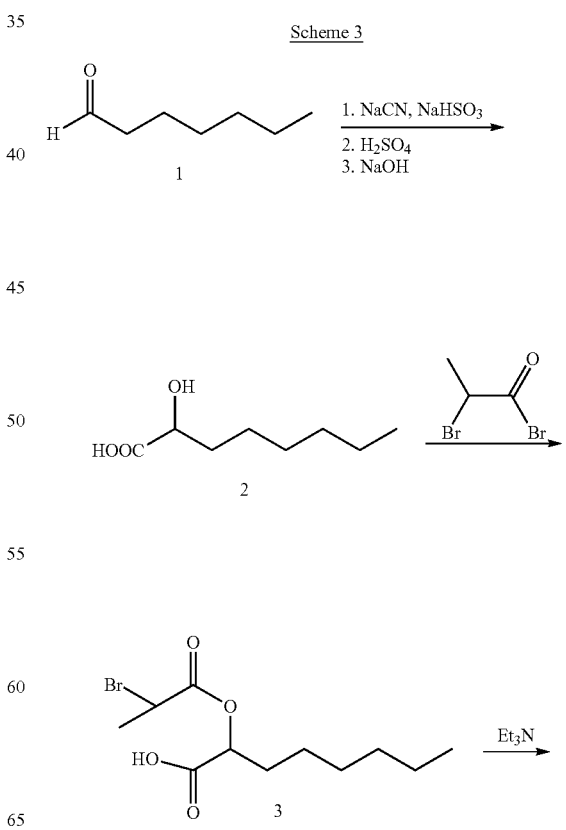

Scheme 3

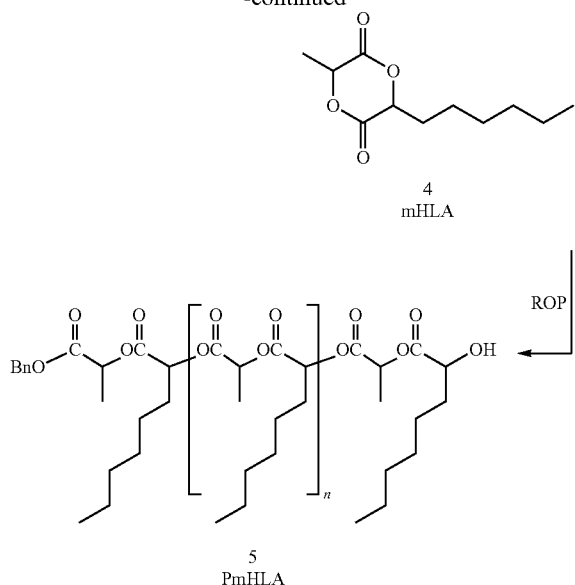

4
mHLA

5
PmHLA

ROP of the mHLA were carried out in convenient bulk conditions at 100° C. with two catalysts, $Sn(Oct)_2$ or DMAP (respectively 1 and 2 eq. to the initiator), in the presence of benzyl alcohol as initiator. Benzyl alcohol was chosen for its suitability to be cleaved off with $H_2$/Pd and setting free the reactive carboxylic acid end group on the PLA polymer chain for possible further functionalizations. The degree of polymerization (DP), which can be controlled by adjusting the ratio of [monomer]/[BnOH], was targeted at 45 to yield a polymer of about 8000 g/mol molecular weight. Predictable molecular weights and narrow polydispersities were obtained for both catalysts (Table 5). For the same polymerization time of 4 hours, the conversion obtained for $Sn(Oct)_2$ catalyst (95%) was slightly higher than that observed for DMAP (82%), even when this latter was used in higher amounts up to 2 eq. to initiator. Thus the classical $Sn(Oct)_2$ catalyst was selected for the PmHLA synthesis, having the further advantage of being already FDA approved (Food Drug Admin. Food, 1975). Studies on the ROP kinetics of the mHLA with this catalyst were performed in terms of molecular weight versus conversion (FIG. 1). For a targeted DP of 45, a linear function was obtained showing that the polymerization is well controlled and of a "living character". A typical $^1$H NMR spectrum of the PmHLA after purification by precipitation in methanol is presented in FIG. 3 and is consistent with this "living character" of the ROP with the presence of both signals of the benzylester and C$\underline{H}$OH end groups, which confirms the initiation of the ROP by the alcoholate active species. Same studies were performed with the DMAP catalyst and showed the same "living" behaviour. For a high DP of 120, a loss in the control began to occur for conversions higher than 50% (FIG. 1). This is probably due to the increasing viscosity of the bulk reaction mixture, increasing transesterification side reactions rather than the polymer chain growth via the active polymer end group.

TABLE 5

ROP of mHLA with $Sn(Oct)_2$ and DMAP at 100° C. in bulk.

| Catalyst | Catalyst/ BnOH | Time (h) | Conversion | DP Targeted | DP Measured[a] | $M_n$ (g/mol) | $M_w/M_n$ |
|---|---|---|---|---|---|---|---|
| $Sn(Oct)_2$ | 1 | 4 | 95 | 45 | 39 | 7500 | 1.25 |
| DMAP | 2 | 4 | 82 | 45 | 35 | 7100 | 1.15 |

Figure 2A:
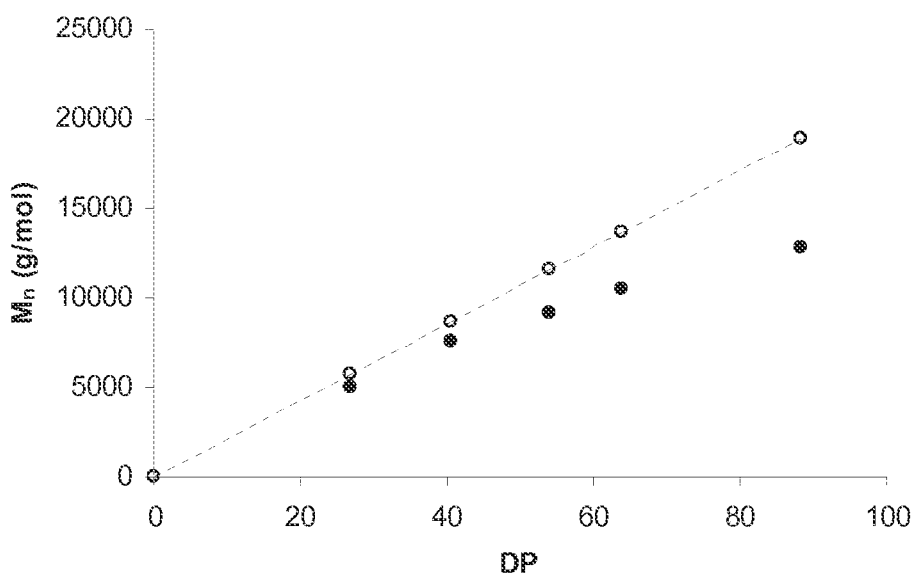
FIGS. 2A-B: Control of the ROP of monohexyl-substituted lactide (FIG. 2A) and D,L-lactide (FIG. 2B) performed in bulk or toluene ([monomer]/[BnOH]=targeted DP, [BnOH]/[$Sn(Oct)_2$]=1).
Figure 2B:
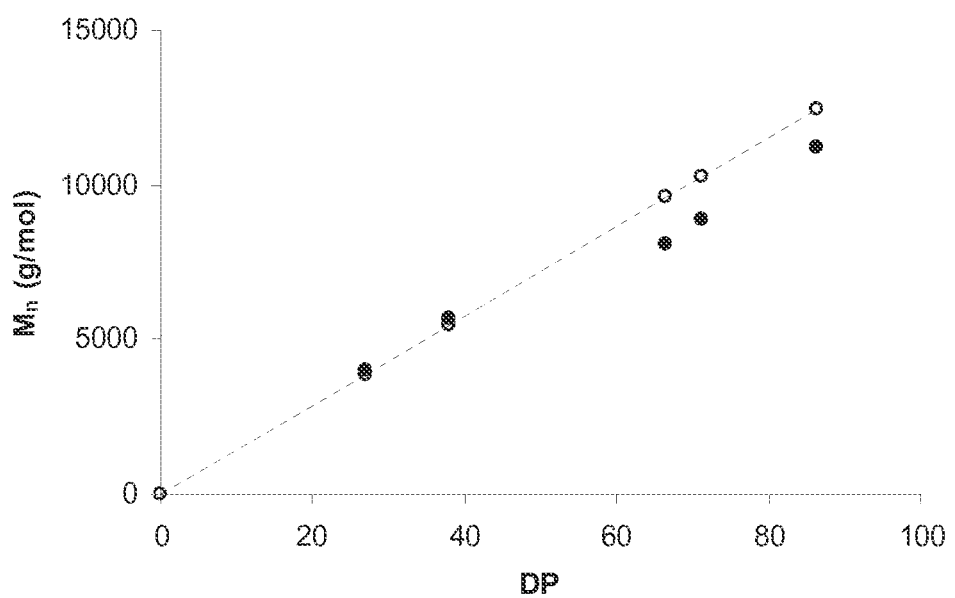

[a]Determined by $^1$H NMR on the precipitated polymer using signals of the benzyl protons of the benzyl ester end groups In FIGS. 2A-B the actual and expected molecular weights for different targeted DPs are reported.

The obtained molecular weights correspond to the theoretically expected ones up to a DP=60. For higher molecular weights a loss in the control of polymerization of mHLA (a) compared to that of D,L-lactide (b) appears. Here a better control can be achieved by changing the reactions conditions. However for the purpose of the desired pharmaceutical applications, this range of controlled polymer molecular weight from 2500 to 10000 g/mol (e.g. DP=10 to 50) is quite satisfactory since rather low viscosities and reasonable degradation times will be required for the potential use as injectable systems. Further investigations PmHLAs of different DPs up to 60 ($M_n$ from 2800 to 9100 g/mol) were then prepared with very good control and quite narrow polydispersities ($M_w/M_n$~1.19-1.35) in bulk conditions at 100° C. (Table 6) by targeting the adequate DP and adjusting the polymerization times. For the PmHLA of the lowest $M_n$ of 2800 g/mol, the highest polydispersity was observed ($M_w/M_n$=1.35). Indeed the conversion was rapidly complete for this low targeted DP, and then side transesterification reactions began to occur. Here the polymerization time can be shortened to improve the molecular weight distribution. Standard PLA of about 7500 g/mol was prepared under comparable reaction conditions as a control. A polymerization time of 1.5 hours was sufficient to obtain a conversion of about 90% whereas longer times were required for ROP of the hexyl-substituted lactide due to the steric hindrance of the hexyl side groups, e.g. 2 hours for the analog PmHLA of 7500 g/mol.

TABLE 6

Synthesis of PmHLA of different molecular weights (ROP at 100° C.) and their material properties.

| Monomer | ROP solvent | Time (h) | DP Targeted | DP Measured[a] | $M_n$ (g/mol) | $M_w$ (g/mol) | $M_w/M_n$ | $T_g$ (° C.) | $\eta_0$ [25° C.] (Pa·s) |
|---------|-------------|----------|-------------|----------------|---------------|---------------|-----------|--------------|--------------------------|
| mHLA    | Bulk        | 1.5      | 15          | 13             | 2800          | 3750          | 1.35      | −22.4        | 140                      |
| mHLA    | Bulk        | 1.5      | 30          | 26             | 4800          | 6000          | 1.25      | −17          | 715                      |
| mHLA    | Bulk        | 2        | 36          | 33             | 6500          | 7700          | 1.19      | −13.3        | 1750                     |
| mHLA    | Bulk        | 2        | 45          | 40             | 7500          | 9400          | 1.25      | −12          | 3500                     |
| mHLA    | Bulk        | 3        | 60          | 59             | 9100          | 11850         | 1.30      | −10.5        | 4850                     |
| D,L-LA  | Tol.        | 1.5      | 50          | 48             | 7200          | 9200          | 1.28      | 40           | glassy                   |

Figure 3:
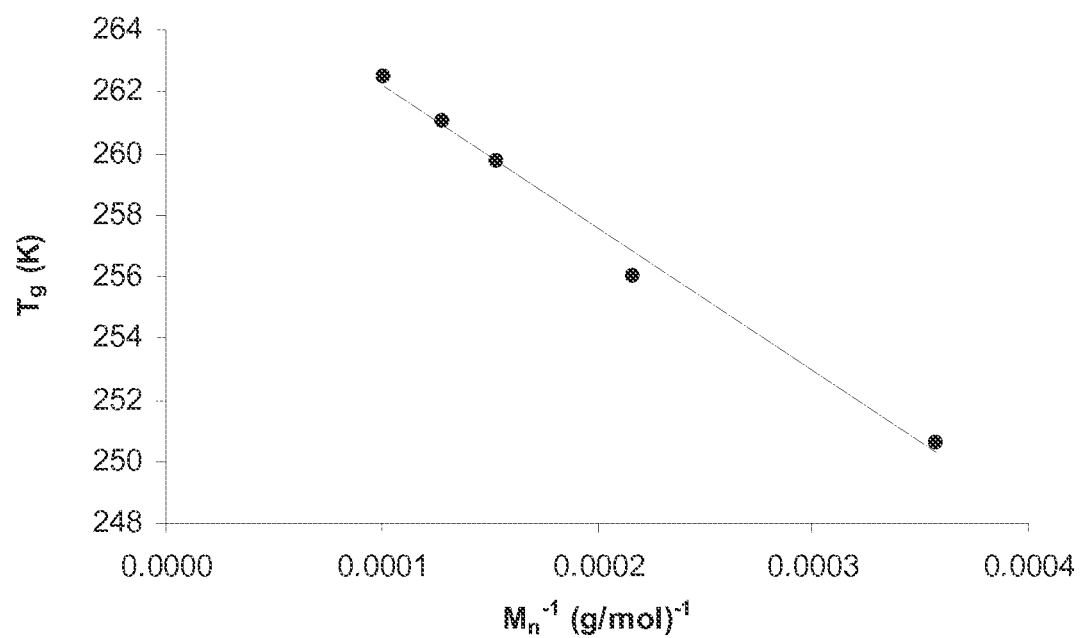
FIG. 3: PmHLA glass transition temperature ($T_g$) as a function of the reciprocal molecular weight ($M_n^{-1}$).
Figure 4:
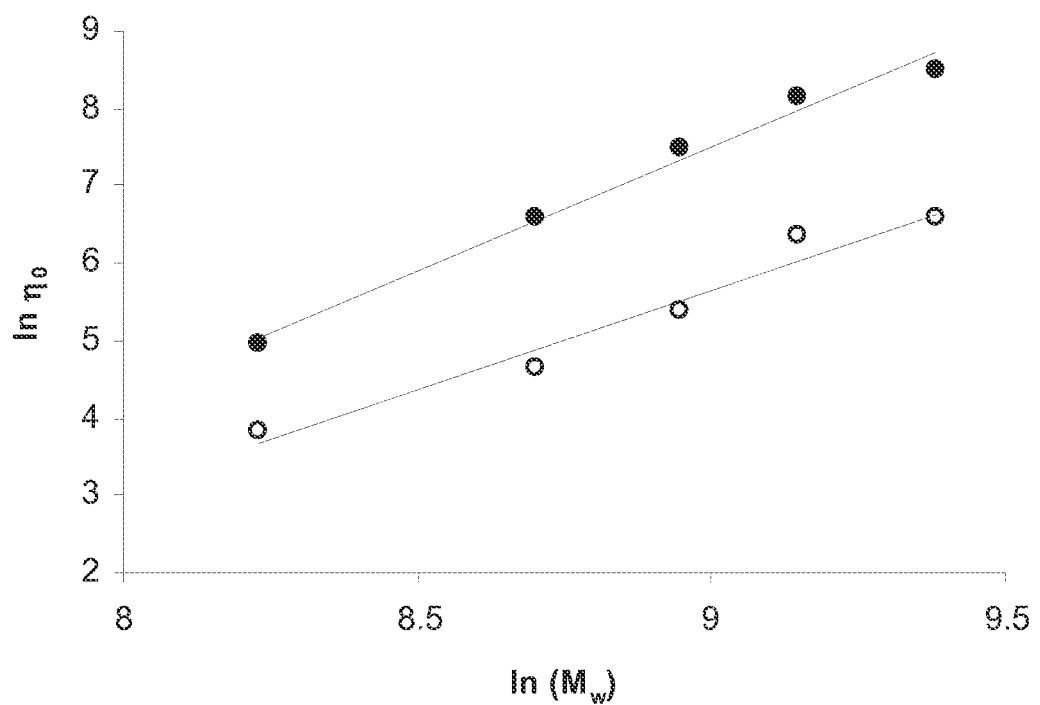
FIG. 4: PmHLA zero shear viscosity ($\eta_0$) at 37° C. (○) and 25° C. (●) as a function of the weight average molecular weight ($M_w$).

[a] Determined by $^1$H NMR on the precipitated polymer using signals of the benzyl protons of the benzyl ester end groups Polymer Physical Properties Polymer material properties were particularly investigated in terms of glass transition temperatures ($T_g$) and melt viscosity, two important parameters for the evaluation of the "injectability" of the material. The $T_g$ varied from −22.5 to −10° C. in the range of the investigated molecular weights (Table 6). The evolution of the $T_g$ as a function of $M_n$ fits quite well the Fox-Flory equation, as shown in FIG. 3 by the plot of $T_g$ as a function of the reciprocal $M_n$. For the same $M_n$ of about 7500, PmHLA and PLA presented radically different $T_g$ values with −12° C. for PmHLA and 40° C. for PLA. The impact of the flexible hexyl groups on the glass transition temperature and other physical properties in comparison to standard PLA are obvious. Due to their low $T_g$ the poly(hexyl-substituted lactides) are in a rubber viscous state at room temperature. For envisioned medical applications by injection the viscosity for these polymers can be controlled by choosing the appropriate molecular weight. In Table 6 the zero shear viscosity values (e.g. in the Newtonian domain) at 25° C. are presented. Here for all the molecular weights PmHLA typically behaved like a Newtonian fluid for a shear rate ranging from 0.1 to 10 s$^{-1}$ with a constant viscosity. A shear thinning behaviour was observed above this value as it is known for many polymers. The zero shear viscosity varied from 140 to 4850 Pa·s at 25° C. and from 45 to 720 Pa·s at 37° C. by increasing the molecular weight $M_n$ from 2800 to 9100 g/mol. As shown in FIG. 4, the variation of the PmHLA zero shear viscosity with $M_w$ (in log-log scale) followed the Fox and Loshaek (1955) theory with a coefficient slope $\alpha \approx 3.2$ independent of the temperature used, suggesting an entanglement point $M_c$ of the polymer inferior to $M_w$=3700 g/mol and an interpenetration of the PmHLA chains (Porter and Johnson, 1966). In conclusion the physical properties or the "injectability" of the hexyl substituted polylactides can be modulated and fine-tuned by varying the molecular weight of these polylactides. Moreover they can be very good predicted from the already well-established calculation models.

Degradation Studies

Figure 6A:
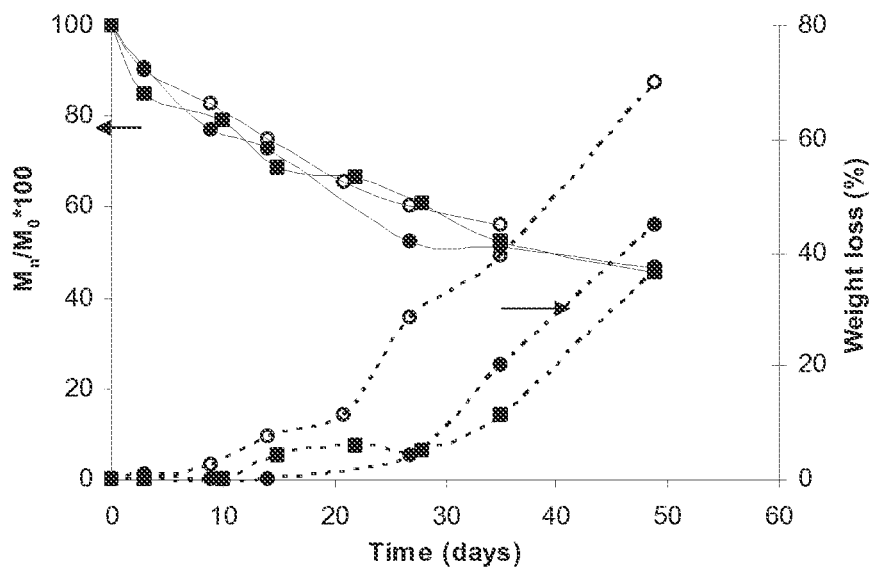
Figure 6B:
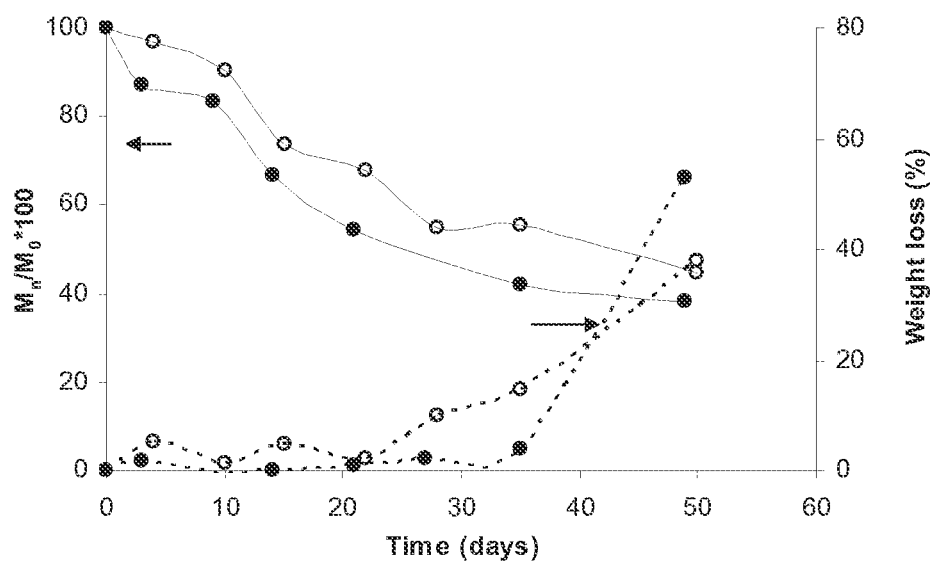

For the purpose of injectable drug delivery systems the degradability of the new poly(hexyl-substituted lactide) was investigated. Due to the hexyl side groups this new polylactide is much more hydrophobic than a comparable standard PLA and causes differences to the degradation of PLA. The degradation mechanism of PmHLA and PLA of comparable molecular weights was investigated in terms of molecular weight and weight loss as a function of time in phosphate buffer pH 7.4 at 37° C. The results are shown in FIG. 6B for PmHLA and PLA of comparable molecular weights of 7500 g/mol. The molecular weight decrease profile for PmHLA was similar to that of standard PLA. The hexyl groups on the PmHLA could be expected to decrease the rate of hydrolysis of the ester bonds, because of their higher steric hindrance and a possible hydrophobic protection against water and its hydroxyl ions. But in fact the degradation rate was slightly higher for the PmHLA, which can be explained by the physical state of the polymers at 37° C. Here PLA is a glassy rigid polymer ($T_g$=40° C.) whereas PmHLA is in a rubber viscous state ($T_g$=−12° C.). The latter state favours the penetration of the water into the polymer matrix, leading to a higher hydrolyzation rate, what is also reported by Ye et al. (1997). This influence of the physical state of the polymer on the degradation profile was confirmed by further degradation studies performed at 60° C., a temperature which is a above the $T_g$ of both polymers. As expected the degradation rates strongly increased, but now PmHLA degraded slower than PLA. At 60° C. PmHLA and PLA are both in a rubber state, and thus the slower degradation for PmHLA could only be attributed to the presence and influence of the hydrophobic hexyl groups on the polymer.

Following up the degradation over the whole time period of seven weeks the degradation process could be divided into two phases. In the first weeks of degradation no mass loss was observed and the decrease in molecular weight was the most pronounced. In the second phase the onset of the mass loss occurred together with a slower decrease of the molecular weight. This is typical for a "bulk erosion" mechanism, in which the hydrolysis first occurs in the inner polymer matrix with a random scission of the ester bonds due to water absorption, followed by the diffusion of the small oligomers formed out of the polymer bulk. This was corroborated by the visual aspect of the polymer, which got swollen in the first phase of degradation due to the water absorption. Whereas the "bulk erosion" mechanism is well-known for the poly(D,L-lactide) (Hakkarainen et al., 1996), this mechanism was quite surprising for the hydrophobic PmHLA. Due to the strong hydrophobic effect of the hexyl side groups along the polymer backbone one could expect a "surface erosion" mechanism, as it is known for the hydrophobic poly(ortho-esters). In fact, for the studied PmHLAs the mono-substitution pattern and the existing number of hexyl side groups on the polylactide backbone do not have a strong enough hydrophobic effect of being water repellent and protecting the inner polymer matrix against hydrolyzation. Finally, it is to point out that despite both polymers had a similar degradation profile in terms of molecular weight decrease, the weight loss of PLA occurred earlier than that of PmHLA. This effect might most probably be due to the less water-soluble hexyl-substituted degradation residues from the PmHLA, which diffuse less good from the inner polymer matrix into the outer aqueous phase.

As the inventors demonstrated the viscosity of this novel monohexyl-substituted PLA can be tailored in order to obtain injectable polymers which at the same time show a nice degradability profile for controlled drug release. Investigations with different incorporated drugs are in progress and will be presented in the near future.

The inventors have presented in this Example the controlled synthesis and properties of a novel poly(monohexyl-substituted lactide) (PmHLA). The ROP of the mHLA monomer for targeted DPs up to 60 was well controlled with a living character as shown by molecular weight versus conversion studies and $^1$H NMR. The hexyl side groups along the PLA-polymer backbone had a strong impact on the physical properties in terms of glass transition temperature ($T_g$) and viscosity. These values can be easily tailored by adjusting the polymers molecular weight, corresponding with the Fox and Flory laws. The poly(mono hexyl-substituted lactide) (PmHLA) shows low viscosity and is suitable for injectable drug delivery systems. Since these new hydrophobic polylactide based polymers are synthesized by ring-opening polymerization (ROP) a fine-tuning of this parameter can possibly be achieved by adjusting the number of hexyl side groups choosing the appropriate ratio of monohexyl lactide- and D,L-lactide monomer for the resulting copolymers. Moreover the functional end groups of these new polymers can be used for adding and building up advanced molecular structures with further functionalities needed for optimized drug delivery systems.

Under physiological conditions the degradation mechanism of PmHLA can be described as "bulk erosion" and the degradation rate is similar to that of standard PLA. Further investigations on different poly(alkyl-substituted lactides), also in combination of copolymers with established PLA/PLGA polymers in various compositions and macromolecular architectures are also envisioned.

Example 3

Controlled Drug Release Using Novel Poly(Hexyl-Substituted Lactides)

Biocompatible and biodegradable polylactides/glycolides (PLA/PLGA) have received great attention over the last thirty years in the biomedical field as sutures, implants, colloidal drug delivery systems, (Penning et al., 1993; Uhrich et al., 1999 in tissue repairing and engineering (Liu and Ma, 2004; Stock and Mayer, Jr., 2001) and also in anti-cancer drug delivery (Mu and Feng, 2003; Jiang et al., 2005). Next to the medical field they are used and of high interest in many other applications e.g. in the packaging area as environmentally friendly materials compared to the commodity polymers currently used (Drumright et al., 2000; Vink et al., 2003). Composting of the waste of PLA derived products leads by degradation back to the non toxic natural lactic acid, which is on the one hand the starting material for these polymers and on the other hand advantageously obtained from renewable resources such as corn starch. Despite the possibility of producing PLA and its copolymers of controlled molecular weight and chemical composition from the lactide/glycolide monomers by ring-opening polymerization (ROP) (Dechy-Cabaret et al., 2004; Kricheldorf et al., 1995; Schwach et al., 1997; Degee et al., 1999; Ryner et al., 2001), these materials do not always show suitable or optimal properties for all the desired applications. For example the PLA/PLGA polymers usually have a glass transition temperature of around 40-60° C. (Jamshidi et al., 1988; Vert et al., 1984), and therefore are not applicable on their own for injectable drug delivery systems. Injectable polymers themselves are receiving increased attention (Amsden et al., 2004; Hatefi and Amsden, 2002) as alternatives to emulsions, liposomes or microsphere injectable drug delivery systems.

The inventors reported in a previous paper the synthesis and ring-opening polymerization (ROP) of new monoalkyl substituted lactides, with a view to design new controlled tailored polymeric PLA based materials (Trimaille et al., 2004). The strategy of substitution of the methyl ligand of the lactide monomer by an other substituent and thereof the synthesis of new functionalized polylactide-based materials by ROP can be achieved by using new reactive catalysts, e.g. tin(II)trifluoromethane sulfonate and 4-dimethylaminopyridine (Trimaille et al., 2004; Moller et al., 2001; Nederberg et al., 2001). These catalysts facilitate the ROP of very steric hindered monomers with a good control of molecular weight and molecular weight distribution. Next to other alkyl-substituted lactides the inventors described the synthesis and characterization of new polylactides obtained from mono-hexyl-substituted lactide and dihexyl-substituted lactide [poly(monohexyl-substituted lactide) and poly(dihexyl-substituted lactide)] which were shown to have low glass transition temperatures ($T_g$<−15° C.) compared to a standard PLA with the analogue molecular weight (Trimaille et al., 2004). Based on these initial results the new hydrophobic substituted polylactides could be favourable and interesting for applications as injectable semi-solid materials for drug delivery comparable to the reported hydrophobic poly(ortho esters) (Merkli et al., 1994; Schwach-Abdellaoui et al., 2001). Moreover, the increased hydrophobicity of these PLA-polymers could lead to further interesting properties in colloidal systems, e.g. in terms of encapsulation efficiency and release of hydrophobic drugs. The inventors' initial studies showed that nanoparticles can be obtained from these new polymers by the nanoprecipitation technique. The used ring-opening polymerization technique with its living character and functional end groups also gives the opportunity to synthesize various new PLA-based copolymers in combination with the established PLA-PLGA systems. By this an enlarged library of different functional PLAs with tailored material properties for biomedical applications can be easily obtained.

The inventors present in this Example a detailed study on these new hexyl-substituted polylactides, their physico-chemical properties, degradation kinetics and mechanism, identification of the degradation products, and release of tetracycline as a model drug, all in comparison to the analogue standard PLA.

Materials:

All materials here were prepared as described in EXAMPLE 1

Monomer Synthesis:

All synthesized monomers were prepared as described in Example 1

Polymer Synthesis and Characterization:

All synthesized polymers were prepared and characterized as described in EXAMPLE 1 and EXAMPLE 2, respectively.

Degradation Studies 40 mg of polymer were placed into flasks and gently heated above the $T_g$ of the polymers. 5 mL of 0.1 M phosphate buffer pH 7.4 were then added and the flasks were slowly agitated at the adequate temperature. At predetermined times polymers were collected, rinsed with milli-Q water and dried to constant weight prior to determination of mass loss and average molecular weight.

Mass loss (ML %) was evaluated by gravimetric analysis and calculated by:

$$ML\ \% = \frac{100(W_0 - W_t)}{W_0}$$

$W_0$ and $W_t$ are the initial weight and the residual weight of the dry polymer at time t.

The molecular weights were determined by GPC as described above.

Electrospray Ionization/Mass Spectrometry.

The degradation products were identified by ESI/MS analysis, which was performed on a Finnigan MAT SSQ7000 quadripole mass spectrometer. The residues present in the aqueous degradation medium, were dried under vacuum, dissolved in a $CH_2Cl_2$/MeOH 9/1 mixture and 150 μL/min were infused into the ESI part. A voltage of 4500 V was maintained on the ESI/MS electrode in order to form the multiprotonated ions of each product. Mass was scanned from 50 to 1500 mass/charge units and 20 scans in 1 min were averaged to obtain the mass spectra.

Tetracycline Release Studies 200 mg polymer and 20 mg tetracycline hydrochloride (TH) were dissolved in 1.7 mL THF and 1 mL methanol and well mixed. The mixture was dried in vacuo at 35° C. for 72 h. From this 30 mg of the tetracycline loaded polymer samples were incubated with 10 mL phosphate buffer 0.1 M pH=7.4 at 37° C. The releasing medium was replaced every day with fresh buffer solution and stored at 4° C. before analysis. The amount of drug released was determined by using a HPLC system with a pump (Waters 600E controller), an autoinjector (Waters 717 plus autosampler), a UV detector (Waters 2487) and an integrator (Millenium software, Waters). The column used was Nucleosil 100-5 C18 (Macherey-Nagel® Gmbh & Co., Duren, Germany) with 5 μm particle size, 250 mm length and 4 mm inner diameter. The mobile phase was a mixture of Milli-Q water and acetonitrile (81.5/18.5 v/v) containing 0.03 M EDTA, 0.011 M $KNO_3$ and acetic acid to give pH 3. A flow rate of 0.7 mL/min was used. The solution was degassed with helium prior to use. Standard solutions of TH of concentrations ranging from 5 to 50 μg/mL in phosphate buffer 0.1 M pH 7.4 were prepared for calibration. The typical retention time of TH was 15.7 min monitored at 353 nm.

Polymer Synthesis and Properties

Based on a quite versatile synthesis method new alkyl-substituted lactide monomers were synthesized for further ring-opening polymerization. The synthesis steps of the here investigated poly(monohexyl-(PmHLA 6) and dihexyl-(PdiHLA 7) substituted lactides) are presented in Scheme 4. The synthesis of the new monohexyl-substituted lactide (mHLA) 4 is based on a "two step one pot" reaction of 2-hydroxyoctanoic acid 2 with 2-bromopropionyl bromide leading to an intermediate ester 3, which undergoes ring-closing after changing to basic reaction conditions with triethylamine. The dihexyl-substituted lactide (diHLA) 5 was synthesized by the simple condensation reaction of the 2-hydroxyoctanoic 2 acid with p-toluenesulfonic acid. The 2-hydroxyoctanoic acid 2 was easily synthesized in large scale from heptanal 1 (Shiosaki and Rapoport, 1985).

Scheme 4

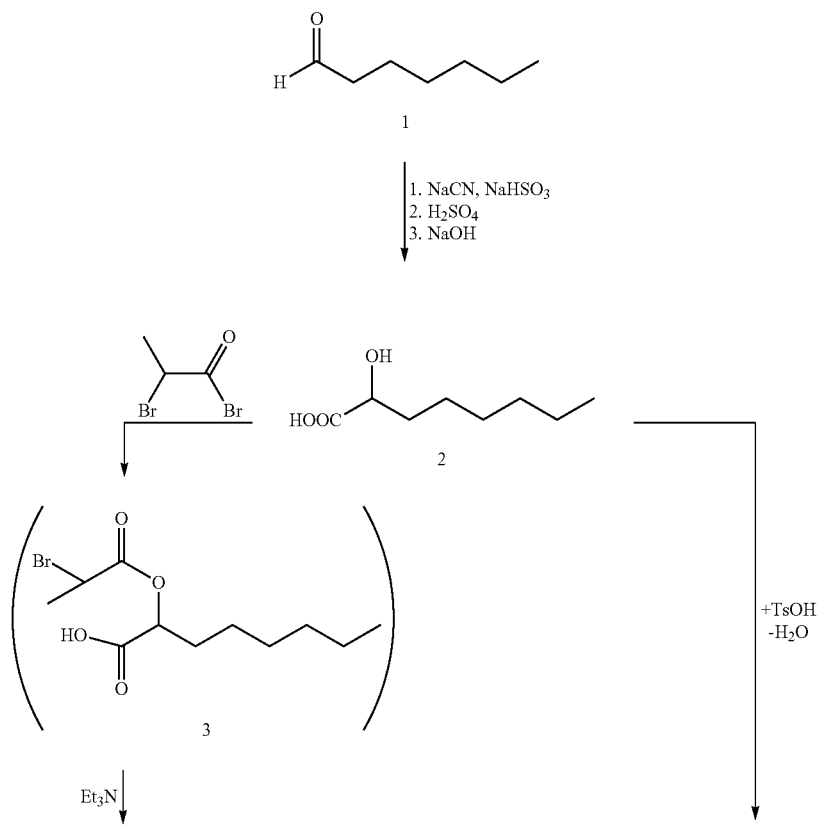

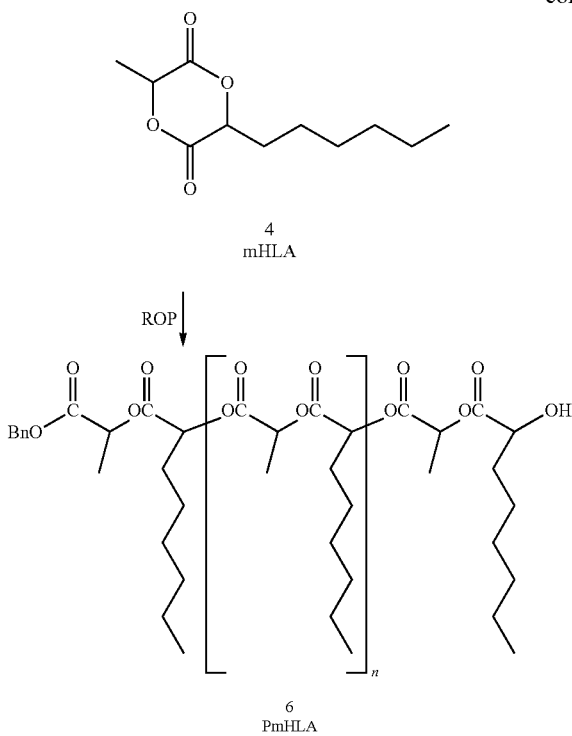

4
mHLA

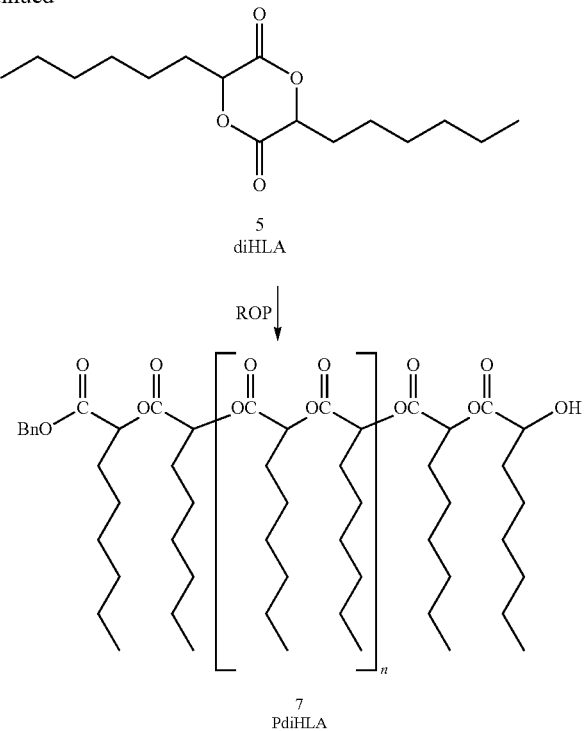

5
diHLA

6
PmHLA

7
PdiHLA

Ring-opening polymerizations of mHLA, diHLA and D,L-lactide were performed with the FDA-approved $Sn(Oct)_2$ catalyst (Food Drug Admin. (1975) and benzyl alcohol as an initiator. Benzyl alcohol was chosen for its suitability to be cleaved off with $H_2$/Pd and setting free the reactive carboxylic acid end group on the PLA polymer chain for possible further functionalizations. The molecular weight and degree of polymerization (DP) can be controlled by adjusting the ratio of [monomer]/[BnOH]. Polymerizations of the hexyl-substituted lactides could be run in solvent-free conditions at a relative moderate temperature of 100° C. due to their low melting point. In contrast for the D,L-lactide polymerizations a solvent is necessary at this reaction temperature and ideally toluene was used.

Figure 5:
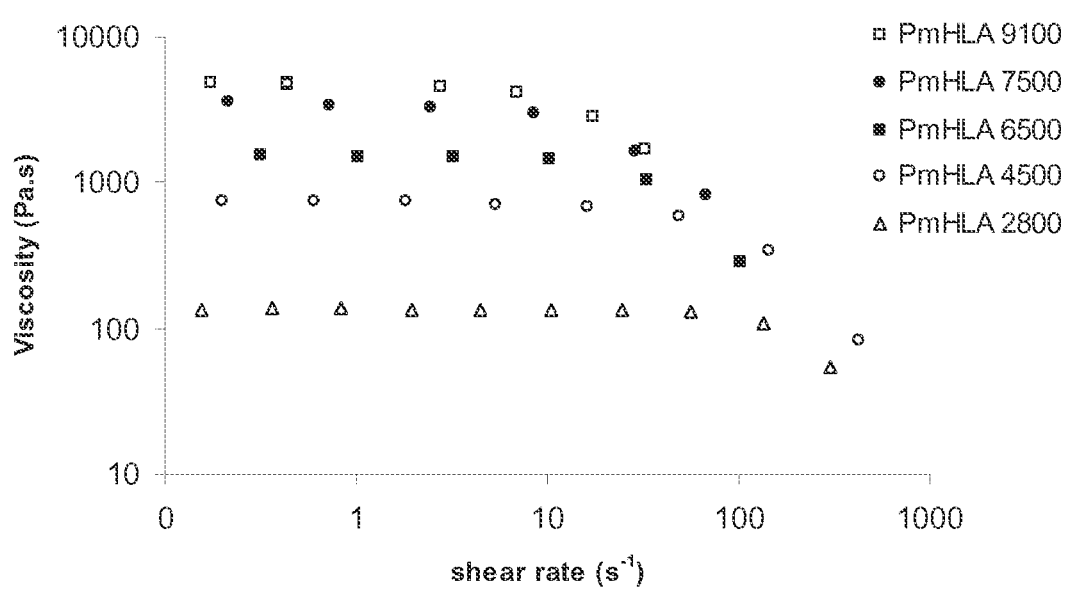
FIG. 5: Viscosity versus shear rate curves for PmHLA of different molecular weights at 25° C.

For the potential use as injectable drug delivery systems poly (hexyl-substituted lactides) with rather low viscosities, reasonable degradation times and drug release rates were desired. The favourable viscosities are given for these polymers having a molecular weight of 2000 to 10000 g/mol or in degree of polymerization DP=10 to 50. These polymers could be prepared with very good control and narrow polydispersities by ring-opening polymerization in bulk conditions. As shown in FIGS. 6A-B the obtained molecular weights correspond to the theoretically expected one up to a DP=60. For higher molecular weights a loss in the control of polymerization of mHLA (a) compared to that of D,L-lactide (b) appears, due to the increasing viscosity of the bulk reaction mixture leading to a loss in monomer reactivity. Here a better control can be achieved by changing the reactions conditions. The polymers selected for the inventors' investigations and their material properties are summarized in Table 7 and discussed in the following. PmHLA and PLA of same molecular weights of about 4500, 7500 and 9000 g/mol were prepared with quite narrow polydispersities by targeting the adequate DP and adjusting the polymerization times. A PdiHLA of 4500 g/mol was synthesized as a further comparison for studying the influence of the higher number of hexyl substituents along the PLA backbone. Polymerization times of 1.5 hours were sufficient to obtain D,L-lactide ROP conversions of about 90% whereas longer times were required for ROP of the substituted lactides due to the steric hindrance of the hexyl side groups (1.5 to 4 hours depending on the DP and the nature of the monomer). The glass transition temperatures ($T_g$) ranged from −17 to −10° C. for PmHLA and from 38 to 41° C. for standard PLA by varying the polymer molecular weights from 4500 to 9100 g/mol. The impact of the flexible hexyl groups on the glass transition temperature and other physical properties in comparison to standard PLA are obvious. The $T_g$ could be further decreased by increasing the number of hexyl groups on the polymer as shown for PdiHLA of 4500 g/mol with a $T_g$ of −42° C., which is 25° C. less than for the analogue monohexyl-substituted lactide. Due to their low $T_g$ the poly(hexyl-substituted lactides) are in a rubber viscous state at room temperature. For envisioned medical applications by injection the viscosity for these polymers can be controlled by choosing the appropriate molecular weight, as shown in FIG. 5. Also tailoring the number of hexyl side groups along the polymer backbone e.g. in random copolymers with PLA are possible. PmHLA typically behaved like a Newtonian fluid for a shear rate ranging from 0.1 to 10 $s^{-1}$, and a shear thinning behaviour was observed above this value, as it is known for many polymers. Looking at the Newtonian domain the viscosity ($\eta_0$) varied from 140 to 4850 Pa·s at 25° C. and from 45 to 720 Pa·s at 37° C. by increasing the molecular weight $M_n$ from 2800 to 9100 g/mol. PdiHLA shows the same behaviour as PmHLA under shear rate, but the Newtonian viscosity with 40 Pa·s was significantly lower than that observed for PmHLA with 715 Pa·s at 25° C. for a $M_n$ of about 4500 g/mol (see Table 7). This can be explained by the increasing flexibility of the whole polymer brought by the hydrophobic and higher number of hexyl side groups. In conclusion the physical properties or the "injectability" of the hexyl-substituted polylactides can be modulated and fine-tuned by varying the molecular weight or the number of hexyl groups on these polylactides.

TABLE 7

Reaction conditions (100° C.) and characteristics of PLA, PmHLA and PdiHLA.

| Monomer | ROP solvent | Time (h) | DP Targeted | DP Measured | $M_n$ (g/mol) | $M_w$ (g/mol) | $M_w/M_n$ | $T_g$ (° C.) | $\eta_0$ 25° C. (Pa · s) |
|---|---|---|---|---|---|---|---|---|---|
| D,L-LA | Tol. | 1.5 | 35 | 34 | 4820 | 6510 | 1.35 | 38 | glassy |
| D,L-LA | Tol. | 1.5 | 50 | 48 | 7200 | 9200 | 1.28 | 40 | glassy |
| D,L-LA | Tol. | 1.5 | 70 | 68 | 9000 | 11800 | 1.31 | 41 | glassy |
| mHLA | Bulk | 1.5 | 30 | 28 | 4800 | 6000 | 1.25 | −17 | 715 |
| mHLA | Bulk | 2 | 45 | 41 | 7500 | 9000 | 1.20 | −12 | 3500 |
| mHLA | Bulk | 3 | 60 | 59 | 9100 | 12070 | 1.32 | −10.5 | 4850 |
| diHLA | Bulk | 4 | 25 | 20 | 4500 | 5620 | 1.25 | −42 | 40 |

Degradation Studies

For the purpose of injectable drug delivery systems the degradability of the new poly(hexyl-substituted lactides) was investigated. Due to the hexyl side groups these new polylactides are much more hydrophobic than a comparable standard PLA and cause differences to the degradation of PLA. Moreover the degradation rate and degradation mechanism has important influence on the drug release profile. In the following the inventors present the results of the degradation studies of PmHLA and PLA at physiological conditions.

The degradation mechanism of PmHLA and PLA of comparable molecular weights was investigated in terms of molecular weight and weight loss as a function of time in phosphate buffer pH 7.4 at 37° C. The results are shown in FIGS. 6A-C. Independent of the chosen initial molecular weight of the polymers, the molecular weight decrease profile for PmHLA was similar to that of standard PLA. The hexyl groups on the PmHLA could be expected to decrease the rate of hydrolysis of the ester bonds, because of their higher steric hindrance and a possible hydrophobic protection against water and its hydroxyl ions. But in fact the degradation rate was slightly higher for the PmHLA, which can be explained by the physical state of the polymers at 37° C. Here PLA is a glassy rigid polymer ($T_g$=40° C.) whereas PmHLA is in a rubber viscous state ($T_g$~−15° C.). The latter state favours the penetration of the water into the polymer matrix, what is also reported by Ye et al. (1997) leading to a higher hydrolyzation rate.

Due to the ROP in the presence of benzyl alcohol as initiator, the synthesized polylactides are bearing benzyl ester end groups. PmHLA was alternatively synthesized with water as initiator for obtaining the analogue polylactides with carboxyl end groups for investigating the impact of these acid groups on the degradation rate. As shown in FIG. 6A no difference was observed for the degradation profile of the benzyl ester terminated and the carboxyl terminated PmHLAs.

Following up the degradation over the whole time period of seven weeks the degradation process could be divided into two phases. In the first weeks of degradation no mass loss was observed and the decrease in molecular weight was fast independent of the starting molecular weight. In the second phase the onset of the mass loss occurred together with a slower decrease of the molecular weight. This is typical for a "bulk erosion" mechanism, in which the hydrolysis first occurs in the inner polymer matrix with a random scission of the ester bonds due to water absorption, followed by the diffusion of the small oligomers formed out of the polymer bulk. This was corroborated by the visual aspect of the polymer, which got swollen in the first phase of degradation due to the water absorption. This "bulk erosion" mechanism is well-known for the poly(D,L-lactide) (Hakkarainen et al., 1996; Grizzi et al., 1995). Due to a possible strong hydrophobic effect of the hexyl side groups along the polymer backbone also a "surface erosion" mechanism could be considered as known for the hydrophobic poly(ortho-esters) (Gurny et al., 1999). In conclusion for the studied PmHLAs the mono-substitution pattern and the existing number of hexyl side groups on the polylactide backbone do not have a strong enough hydrophobic effect of being water repellent and protecting the inner polymer matrix against hydrolyzation.

The degradation studies showed further that with the higher molecular weight the polymers have a later onset of weight loss (FIGS. 6A-C). Despite both polymers had a similar degradation profile in terms of molecular weight decrease, the weight loss of PLA occurred earlier than that of PmHLA. This effect might most probably be due to the less water-soluble hexyl-substituted degradation residues from the PmHLA, which diffuse less good from the inner polymer matrix into the outer aqueous phase.

Further degradation studies were performed at 60° C., a temperature which is above the $T_g$ of both polymers (FIG. 7). As expected the degradation rates strongly increased, but now PmHLA degraded slower than PLA. This result confirms the above discussed influence of the physical state of the polymer on the degradation profile. At 60° C. PmHLA and PLA are both in a rubber state, and now the slower degradation for PmHLA can be attributed to the presence and influence of the hydrophobic hexyl groups on the polymer. This becomes even more evident when comparing the degradation of PmHLA with the doubled numbered hexyl-substituted PdiHLA of the same $M_n$ of about 4500 g/mol, as shown in FIG. 6A. Both polymers are in a rubber state and the molecular weight decrease was much slower for the PdiHLA with a time of latency at the beginning and a molecular weight plateau at 75% of the initial $M_n$ compared to a plateau at 45% for PmHLA. PdiHLA showed hardly degradability, neither at higher temperatures.

The identification of the degradation products is crucial in the perspective to toxicity issues for a potential use of these hexyl-substituted polylactides as injectable drug delivery systems in the human body. Degradation compounds present in the aqueous phase were analyzed by electrospray ionization/mass spectrometry (EIS/MS). The spectrum of PmHLA residues after 48 hours of degradation at 85° C. was determined. The higher temperature was chosen to accelerate the degradation. All molecular weight peaks were identified as being oligo-esters of different sizes arising from the hydrolysis of the ester bonds of the PmHLA (Table 8). The spectrum obtained after 60 hours degradation time revealed only the presence of the molecular weight peaks of 2-hydroxyoctanoic acid 2 (M=159) and lactic acid (M=89). Both compounds were used initially for the synthesis of these polymers, whereby lactic acid is as a natural compound present in the human body non toxic and 2-hydroxyoctanoic acid is approved by the FDA for topical applications (Hall and Hill, 1986).

TABLE 8

Structures and molecular weight assignment for the degradation products of PmHLA.

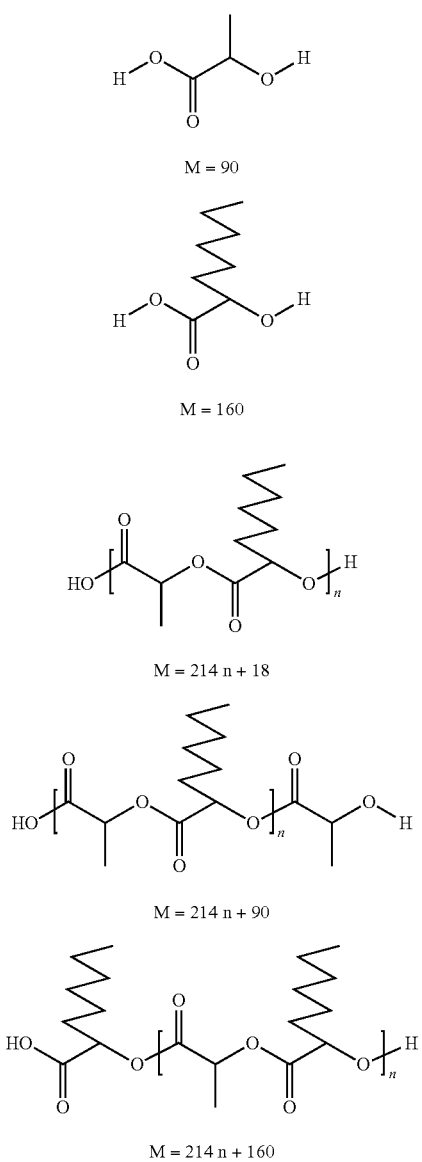

| structure | Peak | peak + 1[a] |
|---|---|---|
| I | 89 | 90 |
| II | 159 | 160 |
| III n = 1 | 231 | 232 |
| III n = 2 | 445 | 446 |
| III n = 3 | 659 | 660 |

TABLE 8-continued

| III n = 4 | 873 | 874 |
|---|---|---|
| III n = 5 | 1087 | 1088 |
| IV n = 1 | 303 | 304 |
| IV n = 2 | 517 | 518 |
| IV n = 3 | 731 | 732 |
| IV n = 4 | 945 | 946 |
| V n = 1 | 373 | 374 |
| V n = 2 | 587 | 588 |
| V n = 3 | 801 | 802 |
| V n = 4 | 1015 | 1016 |
| V n = 5 | 1229 | 1230 |

[a]Actual molecular weights are peak molecular weights plus atomic weight of one proton (negative polarization).

Tetracycline Release

Tetracycline hydrochloride (TH) and tetracycline free base (TB) were tested as a model drug for release studies from the hexyl-substituted polylactides. This broad-spectrum antibiotic has been extensively used in human medicine. Recently Heller and Gurny successfully applied it in the hydrophobic semi-solid poly(ortho esters) (POE) for injectable drug-delivery systems for the treatment of periodontal diseases (Schwach-Abdellaoui et al., 2001a; Schwach-Abdellaoui et al., 2001b). Here investigations with tetracycline hydrochloride (TH) should facilitate easy comparison with the inventors' previous data from the POE studies and check on similarities and differences for these two kinds of hydrophobic polymers.

Figure 8:
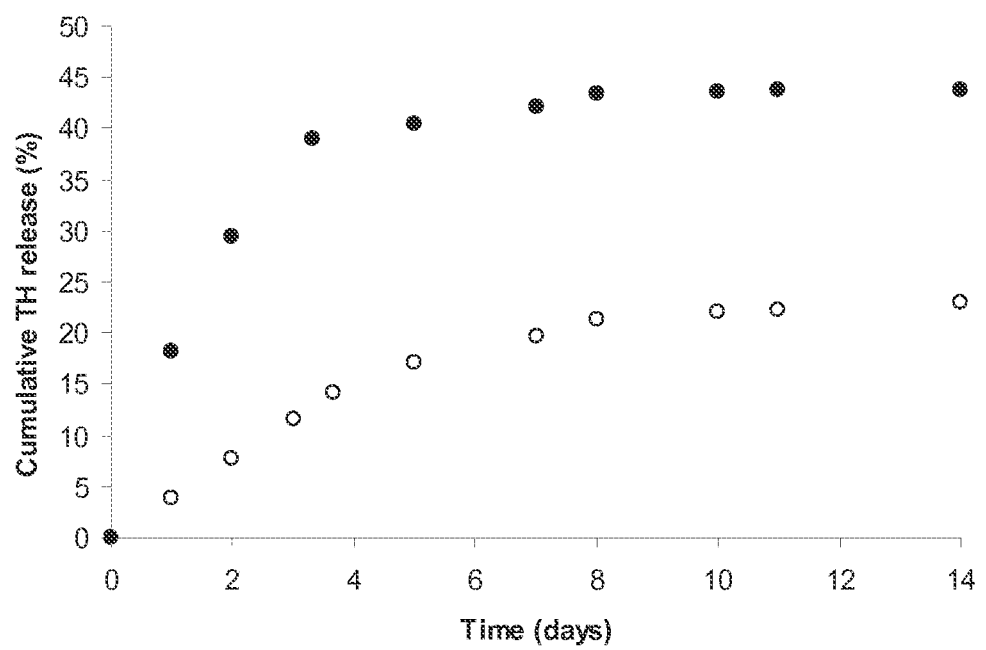
FIG. 8: Tetracycline hydrochloride (TH) release from PmHLA (●) and PLA (○) (10% w/w drug loading) in phosphate buffer pH 7.4 at 37° C.

TH-loaded PmHLA (10% w/w) was simply prepared by dissolution of the polymer and the drug in THF/methanol followed by drying under vacuum. PmHLA with the molecular weight of $M_n$=4500 g/mol was selected, because of its low viscosity and potential use as an injectable drug delivery system. Tetracycline-loaded PLA of the same molecular weight was prepared for a control. GPC analysis was performed after incorporation of tetracycline to check on the initial stability of the drug loaded polymers. Molecular weights remained constant at 37° C., no polymer degradation could be observed possibly induced by the acidic character of the TH. The release profile of the tetracycline from both PmHLA and PLA is shown in FIG. 8. The release of TH was faster from PmHLA than from PLA, and much higher in case of both polymers in the first 6 days than in the days afterwards. Interestingly the total amount of released TH was higher from PmHLA (45% of the initial TH loaded) than from the standard PLA (23%), although the polymers had the same degradation rate (FIG. 6A). The inventors attribute this to the easier diffusion of TH from the PmHLA bulk matrix to the outer phase and into the aqueous degradation medium, because of the rubber viscous state of PmHLA compared to the rigid PLA at 37° C. Comparable release studies were also performed with tetracycline free base (TB). The amount of released TB was again higher from PmHLA than from PLA. For both polymers the amounts of released TB were much lower than in the case of TH. The tetracycline free base (TB) is much less water-soluble than the corresponding hydrochloride (TH) thus the diffusion with water from the inner polymer matrix to the outer phase is slower. The total amount of the initial loaded TH in the polymers was not entirely recovered after release. In fact it could be shown that the TH was partly degraded into the less active epimer 4-epitetracycline. In all the HPLC analyses of the releasing media the signal of this by-product was found besides the active TH. It was previously reported that TH degraded quickly in acidic conditions leading to about 50% of the epimer form (Schwach-Abdellaoui et al., 2001). Therefore it is probable that also here TH is degraded inside the polymer matrix, which has an acidic environment while polymer degradation takes place. The released proportion of the medical active TH compared to 4-epitetracycline was systematically higher for PmHLA than for the standard PLA.

In conclusion the TH drug release from PmHLA with its higher rate and higher total amount of active TH is favourable to PLA. Interestingly the TH release profile from PmHLA is with 45% better than that reported for commercial Actisite fibers, which is loaded with 25% TH and releases about 30% active TH within 14 days (Schwach-Abdellaoui et al., 2001.

In this Example, the inventors present the controlled synthesis and properties of new poly(hexyl-substituted lactides) (PHLA). The hexyl side groups along the PLA-polymer backbone have a strong impact on the physical properties in terms of glass transition temperature ($T_g$) and viscosity. These values can be easily tailored by adjusting the polymers molecular weight. The presented poly(mono hexyl-substituted lactide) (PmHLA) shows low viscosity and is suitable for injectable drug delivery systems. Since these new hydrophobic polylactide based polymers are synthesized by ring-opening polymerization (ROP) a fine-tuning of this parameter can possibly be achieved by adjusting the number of hexyl side groups choosing the appropriate ratio of monohexyl lactide and D,L-lactide monomer for the resulting copolymers. Moreover the functional end groups of these new polymers can be used for adding and building up advanced molecular structures with further functionalities needed for optimized drug delivery systems.

Under physiological conditions the degradation mechanism of PmHLA can be described as "bulk erosion" and the degradation rate is similar to that of standard PLA. The initial release studies of tetracycline hydrochloride (TH) and tetracycline free base (TB) as model drugs showed an even better release of the active form of tetracycline from PmHLA than from the analogue PLA.

Further investigations on different poly(alkyl-substituted lactides), also in combination of copolymers with established PLA/PLGA polymers in various compositions and macromolecular architectures are currently in progress. The development and optimization of these hydrophobic substituted polylactide based polymers for different medical applications will be presented in the near future.

Example 4

Novel Amphiphilic Methoxy Poly(Ethylene Glycol)-Poly(Hexyl-Substituted Lactide) Block Copolymers as Hydrophobic Drug Carriers This Example presents novel amphiphilic methoxy-poly (ethylene glycol)-poly(hexyl-substituted lactides) block copolymers which were synthesized by ring-opening polymerization (ROP) of mono and dihexyl-substituted lactide (mHLA and diHLA) in bulk at 100° C. in the presence of tin(II) 2-ethylhexanoate ($Sn(Oct)_2$) as catalyst and methoxypoly(ethylene glycol) (MPEG) as initiator. MPEG-PmHLA and MPEG-PdiHLA copolymers of predictable molecular weights and narrow polydispersities were obtained, as shown by $^1$H NMR and GPC. DSC experiments showed that the MPEG-PHLA block-copolymer presents a bulk microstructure containing MPEG domains segregated from the PHLA domains. Micelles were successfully prepared from these block copolymers, with sizes ranging from 30 to 80 nm. As expected, the critical micellar concentration (CMC) is found to decrease with the increasing of number of hexyl groups on the polyester block (MPEG-PLA>MPEG-PmHLA>MPEG-PdiHLA) for copolymers of the same composition and molecular weight, allowing to envision these micelles as drug carriers in dilute conditions. The increased hydrophobicity of the micelle core by the higher number of hexyl groups on the PLA chain was evidenced by Nile Red absorbance experiments, with higher amounts of the dye incorporated in the micelles. These novel amphiphilic copolymers in micelle state are of a great interest for optimized hydrophobic drug loadings, as it was shown with the griseofulvin model drug.

Due to their safe and biodegradable properties, amphiphilic PEG-PLA or PEG-PLGA block copolymers have been extensively studied over the past few decades as drug carriers (Kataoka et al., 2001; Yasugi et al., 1999; Riley et al., 2001; Lin et al., 2003), particularly recently for the delivery of anti-cancer drugs (Yoo and Park, 2001; Zhang et al., 2005). Such di-block copolymers can self-assemble in aqueous medium to form spherical micelles (~50 nm) with a core formed by the hydrophobic polylactide segments and a surrounding shell consisting of the hydrophilic PEG chains. The latter stabilizes the surfaces in aqueous systems and ensures a long half-life in the blood compartment due to the reduced interaction with the biological components (Gref et al., 1995). Many potential hydrophobic drugs can be easily entrapped in the core of these micelles, but drug loadings are often low and need to be improved to be efficient for medical applications. The inventors recently described the potential of novel poly(hexyl-substituted lactides) PHLA as an alternative to standard PLA with regards to drug release, degradability and injectability (Trimaille et al., 2004; also see above Examples). The use of these hydrophobic alkyl-substituted PLA with PEG can be interesting for drug delivery due to their micelle size, drug loading and degradability. The inventors describe here the synthesis and characterization of these novel amphiphilic block copolymers, as well as the preparation and properties of the micelles in terms of encapsulation capacity of a hydrophobic drug (griseofulvin). The results are discussed and compared with standard PLA-PEG di-block copolymers, of same molecular weights and composition.

Materials:
All materials here were prepared as described in EXAMPLE 1.

Monomer Synthesis:
All synthesized monomers were prepared as described in EXAMPLE 1.

Polymer Synthesis and Characterization:
All synthesized polymers were prepared and characterized as described in the above EXAMPLES.

Micelle Preparation and Characterization
20 mg purified copolymer and different amounts of GF were dissolved in 2 mL acetone. The solution was then added dropwise (1 droplet/3 s) in 4 mL milli-Q water under stirring. The acetone and a part of the water were removed under reduced pressure to reach a typical micelle concentration of 5.2 mg/mL.

The mean size of the micelles was determined by quasi-elastic light scattering (QELS) with a scattering angle of 90° C. at 25° C. using a Malvern Zetasizer 3000HS (UK), equipped with a He—Ne laser (633 nm).

Nile Red absorbance experiments on blank micelles (no GF): 20 µL of a stock solution of Nile Red (0.97 mg/mL of THF/acetone 1/2) were added to 1.5 mL of micelle solutions from each copolymer (MPEG-PLA, -PmHLA, -PdiHLA of same $M_n$ and composition) of a given concentration (2.1 mg/mL). A PEG solution (2.1 mg/mL water), and pure water (instead of micelle solutions) were also incubated with Nile red, as references The solutions were equilibrated in the darkness for overnight, with removal of THF and acetone. UV-visible spectra of each solution were recorded from 450-650 nm and corrected with the corresponding blanks prepared without Nile red.

Critical micellar concentration (CMC) determination (blank micelles): Fluorescence measurements were performed with Nile Red to determine the CMC. Different dilutions were prepared from the 5 mg/mL stock solution of micelles to obtain samples of concentration ranging from 0.0001 to 1 mg/mL. Then 2 μL of a Nile Red stock solution in acetone (0.97 mg/mL) were added to 200 μL of each sample, and the acetone was evaporated. Fluorescence measurements were performed using a Safire (Tecan) microplate reader in a 96-well plate. Emission spectra were recorded from 560 to 750 nm using a $\lambda_{exc}$=550 nm. The CMC was determined at the inflection point on the plots representing the maximum emission wavelength as a function of the copolymer concentration, as previously described by Coutinho et al. (2002)

Measurements of GF Levels by HPLC

The micellar solutions were centrifuged at 6000 g for 7 minutes to remove the non-entrapped GF. Then 100 μL were dissolved in 900 μL acetonitrile to destroy the micelles and assay the GF which was encapsulated. The HPLC system consisted in a pump (Waters 600E controller), an autoinjector (Waters 717 plus autosampler), a UV detector (Waters 2487) and an integrator (Millenium software, Waters). The column used was Nucleosil 100-5 C18 (Macherey-Nagel® Gmbh & Co., Duren, Germany) with 5 μm particle size, 250 mm length and 4 mm inner diameter. The mobile phase was a mixture of 45 mM potassium dihydrogen phosphate solution (in Milli-Q water) and acetonitrile (45 v %). Pyrophosphoric acid was used to give pH 3. A flow rate of 1 mL/min was used. The solution was degassed with helium prior to use. Standard solutions of GF in water/acetonitrile (1/9) of concentrations ranging from 2 to 18 μg/mL were prepared for calibration. The typical retention time of GF was 9.5 min monitored at 293 nm. It was checked that PEG-P(H)LA copolymers caused no interference at this wavelength.

Synthesis and Characterization of Amphiphilic PEG-PHLA.

In the inventors' previous work the inventors reported the synthesis and ring-opening polymerization of novel alkyl-substituted lactide monomers for the design of functionalized polylactide materials (Trimaille et al., 2004). The inventors have particularly focused on the mono and di hexyl-substituted lactide (mHLA and diHLA, respectively), which led after ring-opening polymerization to new biodegradable polymers with interesting physical properties in comparison to standard PLA/PLGA. Here, studies are presented on the potential of these hydrophobic polylactides in combination with PEG as novel amphiphilic block copolymers. The mHLA synthesis is based on a "two step one pot" reaction of 2-hydroxyoctanoic acid 2, easily synthesized in large scale from heptanal 1, with 2-bromopropionyl bromide leading to an intermediate ester 3, which undergoes ring-closing after changing to basic reaction conditions with triethylamine (Scheme 5). The diHLA 5 was synthesized by the simple condensation reaction of the 2-hydroxyoctanoic acid with p-toluenesulfonic acid in a Dean-Stark apparatus. The di-block MPEG-PmHLA 6 and MPEG-PdiHLA 7 copolymers were synthesized by ring-opening polymerization of the mHLA and diHLA, respectively, in bulk at 100° C. using methoxy-PEG-OH 2000 g/mol (DP-45, referred as MPEG2) as an initiator and the FDA-approved catalyst $Sn(Oct)_2$ (molar ratio $Sn(Oct)_2$/MPEG=0.5), as described in Scheme 5. Both initiator and catalyst were used as stock solutions in THF, and the solvent being removed from the reaction flask in the beginning of the polymerization. D,L-lactide was polymerized under the same conditions as a reference.

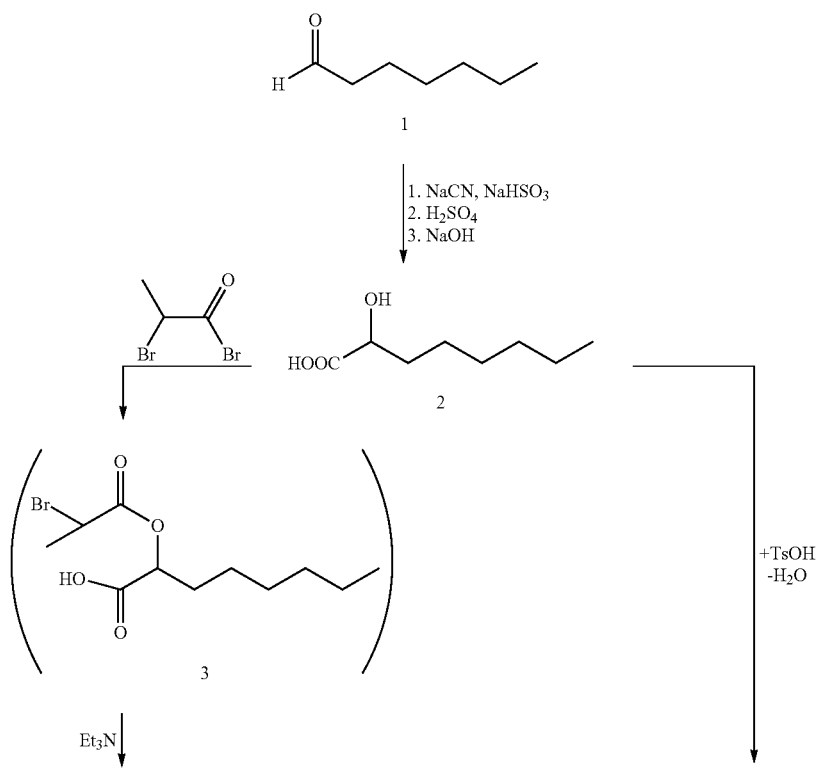

Scheme 5

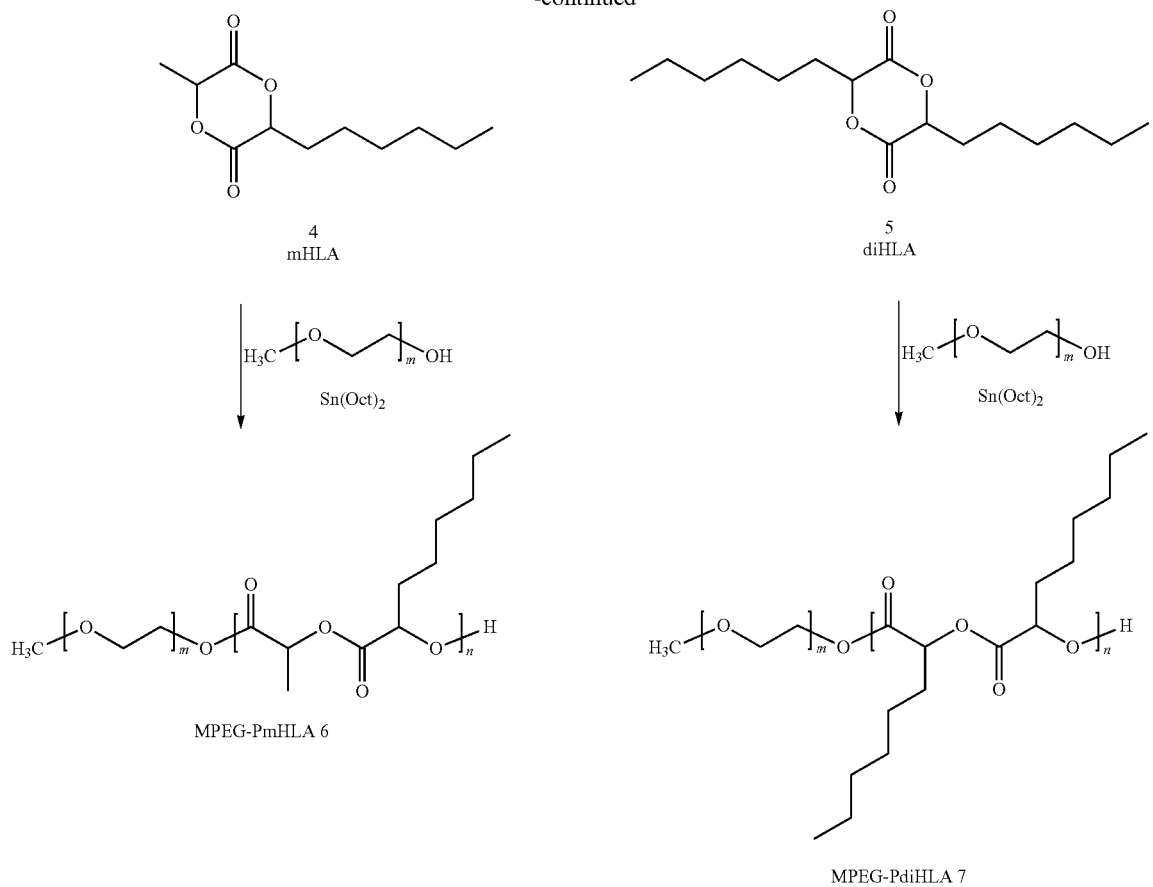

The results of the ROP of the different lactides are presented in Table 9. First, ROP was performed with a targeted DP of 15 for both mHLA and D,L-lactide. 1 hour polymerization time appeared sufficient to reach a nearly complete conversion for D,L-lactide (95%). The conversion obtained for mHLA after the same polymerization time was a bit lower (84%, data not shown), due to the steric hindrance brought by the hexyl side groups. Therefore the ROP of mHLA was performed for 1.5 hours and the conversion was nearly complete (94%). A polymerization time of 1.5 hours was also sufficient to reach an acceptable conversion of the mHLA for a targeted DP of 30 (90%). A prolonged time of 4 hours was required to obtain a good conversion (>90%) for the even more hindered diHLA. In the following, the copolymers will be referred as MPEG2-PLA3, MPEG2-PHLA3 and MPEG2-PHLA5, respectively (MPEGx-P(H)LAy, where x and y represent the $M_n$ of the MPEG and P(H)LA blocks in kg/mol, respectively).

TABLE 9

Characteristics of the copolymers obtained by ROP of the different lactides with MPEG 2000 g/mol as initiator (bulk, 100° C.)

| Name | Monomer | Time (h) | Lactide DP Targ. | Lactide DP exp | Lactide conv. (%) | PEG/PHLA (wt %) Feed | PEG/PHLA (wt %) Exp. | $M_n$ (g/mol) | $M_w/M_n$ |
|---|---|---|---|---|---|---|---|---|---|
| MPEG2-PLA3 | D,L-LA | 1 | 15 | 15 | 95 | 48/52 | 42/58 | 4800 | 1.18 |
| MPEG2-PmHLA3 | mHLA | 1.5 | 15 | 13 | 94 | 38/62 | 39/61 | 5050 | 1.18 |
| MPEG2-PmHLA5 | mHLA | 1.5 | 30 | 27 | 90 | 24/76 | 28/72 | 7100 | 1.17 |
| MPEG2-PdiHLA3 | diHLA | 4 | 20 | 12 | >90 | 26/74 | 38/62 | 4750 | 1.29 |

All copolymer molecular weights were close to those expected, with narrow polydispersities ($M_w/M_n$~1.15), indicating that the polymerizations were well controlled. The shift in retention time observed by GPC analysis for MPEG-PmHLA compared to MPEG showed that the MPEG "macro-alcohol" initiated the polymerization well. As an example for the polymer characterization, the $^1$H-NMR spectrum (300 MHz, CDCl$_3$) was determined for the MPEG-PHLA copolymer after purification by precipitation in hexane. Both MPEG and lactide proton peaks could be clearly identified, and the composition of the copolymer could be deduced from the peak integrals of the CH$_2$ protons of the PEG and the methine protons of the hexyl lactide. $^1$H-NMR spectrum of MPEG2-

PmHLA3 was also determined. Compositions were close to those expected (Table 9), confirming that the ROP were well controlled.

Analysis of the Copolymer Microstructure by DSC

Figure 9:
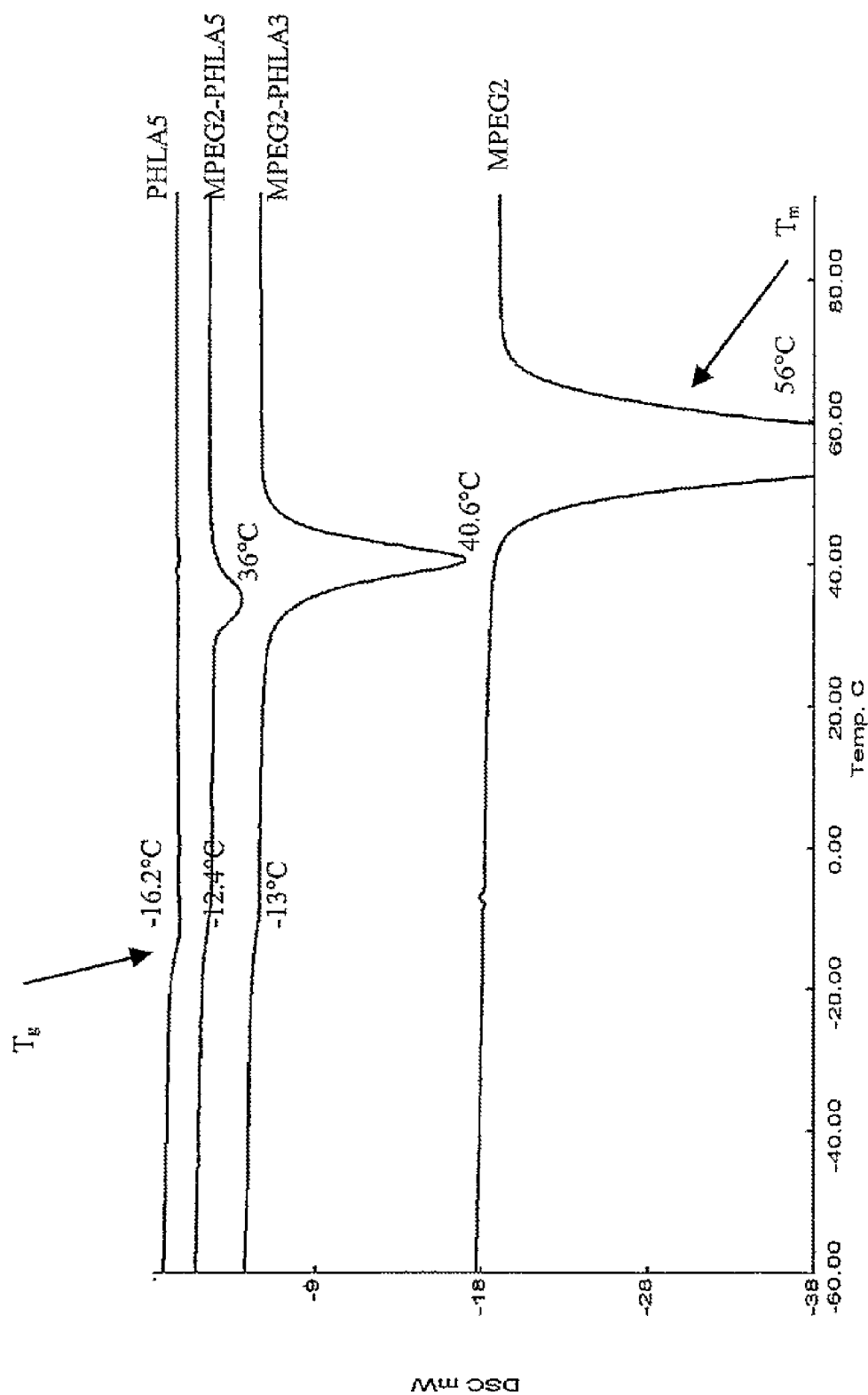
FIG. 9: DSC chromatograms of the MPEG-PmHLA copolymers.

DSC experiments were performed on MPEG-PHLA copolymers to elucidate the copolymer microstructure and the results are shown in FIG. 9 for the case of MPEG-PmHLA copolymers. As a reference, both PmHLA5 and MPEG2 homopolymers were analyzed. PmHLA5 is an amorphous polymer showing a low $T_g=16°$ C., whereas MPEG2 is highly crystalline, showing a melting peak $T_m=56°$ C. The DSC spectra of the MPEG-PHLA block-copolymers showed characteristic features of both homopolymers, demonstrating that the copolymer present a bulk microstructure containing MPEG domains segregated from PmHLA domains. However the shift in both melting and glass transition temperatures, compared to the homopolymers, show that there are interactions between both polymer chains. They can be attributed to their covalent attachment, limiting the mobility of the MPEG as well as the PmHLA chains. When increasing the chain length of the PmHLA in the block copolymer, the melting temperature shifted to lower values (from 56° C. to 36° C.), together with a decrease in the peak intensity. This demonstrates a less pronounced crystallinity in the block copolymer in comparison to the MPEG homopolymer. The $T_g$ of the copolymers (−12.5 and −13° C.) was slightly increased compared to the one of PmHLA homopolymer (−16.2° C.), which also is probably due to a reduced mobility of the PmHLA segments when incorporated in the copolymer, as discussed before.

DSC analysis for the MPEG2-PdiHLA3 copolymer showed typically the same profile as MPEG-PmHLA with a $T_m$ of 38° C. and a $T_g$ of −42° C. (the $T_g$ of the PdiHLA homopolymer of $M_n=5600$ g/mol is −47° C., as previously reported (Trimaille et al., 2004).

Micelle Preparation and Characterization

The amphiphilic nature of the diblock copolymers, consisting of a hydrophobic P(H)LA and a hydrophilic PEG segment, provides the opportunity to form micelles in water with a PLA core and a PEG shell. MPEG2-PLA3, MPEG2-PLA3, MPEG2-PLA3 copolymers, with the same molecular weight (~5000 g/mol) and composition (PEG/PLA~40/60 in wt %) were used for the micelle preparation. The polymeric micelles were prepared by a direct precipitation method using acetone (Yoo and Park, 2001). The latter was removed under reduced pressure after the micelle preparation. The mean size of the micelles was determined by QELS measurements at 90° C. and the results are presented in Table 10 (column 0 mg/g). The smallest micelles were observed for the MPEG2-PdiHLA3 copolymer with 30 nm mean diameter compared to about 70 nm for the analogs MPEG2-PLA3 and MPEG2-PmHLA3. This can be explained by the higher hydrophobicity of the polylactide block when increasing the number of hexyl groups along the chain, favouring a stronger shrinkage upon addition of the water, as the non-solvent, during the micelle preparation. It is to point out that the polydispersity index given by QELS was rather high (>0.2). In fact, a multimodal analysis showed the presence of few aggregates (400-700 nm) contributing to the increase in the polydispersity. These aggregates could be easily removed by filtration.

TABLE 10

Mean size (determined by quasi-elastic light scattering measurements, in triplicate) of the blank and GF-loaded micelles prepared from the different copolymers.

| Copolymer | Mean size in nm (PI$^a$) | | | |
|---|---|---|---|---|
| | 0 mg/g$^b$ | 10 mg/g$^b$ | 30 mg/g$^b$ | 40 mg/g$^b$ |
| MPEG2-PLA3 | 63.9 ± 1.2 (0.50) | 70.0 ± 0.5 (0.53) | 79.2 ± 0.1 (0.50) | 19.3 ± 0.1 (0.10) |
| MPEG2-PmHLA3 | 77.4 ± 0.6 (0.60) | 50.5 ± 0.1 (0.47) | 30.4 ± 0.7 (0.30) | 43.5 ± 1.1 (0.31) |
| MPEG-PdiHLA3 | 29.1 ± 0.2 (0.26) | 52.7 ± 0.4 (0.51) | 32.5 ± 0.6 (0.33) | 39.4 ± 0.4 (0.37) |

$^a$Polydipsersity ($\mu_2/\Gamma^2$) provided by quasi-elastic light scattering.
$^a$introduced amount of GF in milligram per gram of copolymer for micelle preparation In order to further characterize the properties of the micelles formed from these novel PHLA-based amphiphilic copolymers compared to those prepared from the standard MPEG-PLA, Nile Red probe incorporation experiments were performed. The maximum absorption wavelength of this dye is strongly influenced by its hydrophobic environment, as already reported by Davis et al. (1966). Nile red solution in each micelle solution (2.1 mg/mL), and the mixtures were slowly agitated for 24 hours. The micelle solutions turned quickly reddish as a result of the diffusion of the Nile red into the core of the micelles, whereas control solutions with pure PEG and pure water remained uncoloured. UV-visible spectra were recorded for MPEG2-PLA3, MPEG2-PmHLA3 and MPEG2-PdiHLA3. The maximum wavelength absorption is shifting from 545 nm to 540 nm and 535 nm, respectively, indicating clearly that the polarity of the micelle is decreasing as a result of the increasing density of hexyl groups on the PLA chain. Moreover, the Nile Red absorbance was higher with an increasing number of hexyl groups on the polyester, showing that higher amounts of the Nile Red hydrophobic molecule were incorporated in the micelle core. The quasi absence of absorbance observed for the sample made of pure PEG confirmed that the Nile Red has no affinity for the hydrophilic PEG block, and is only to observe in combination with the hydrophobic P(H)LA block, which is concentrated in the core of the micelle.

Figure 10A:
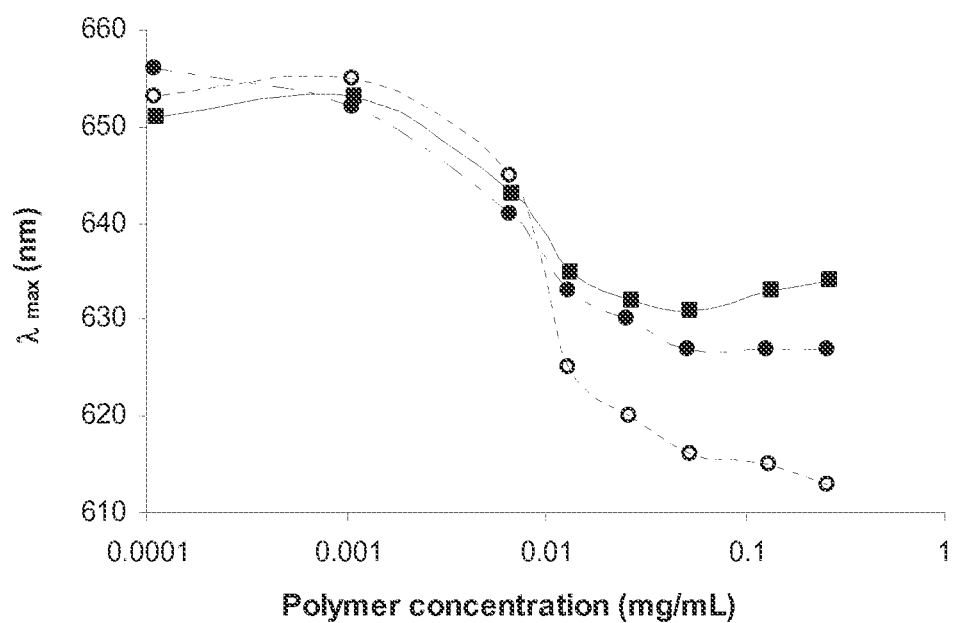
FIGS. 10A-B: Plot of the maximum emission wavelength (FIG. 10A) and fluorescence emission intensity (FIG. 10B) of the Nile red vs. copolymer concentration for MPEG2-PLA3 (○), MPEG2-PmHLA3 (●) and MPEG2-PdiHLA3 (■) micelles.
Figure 10B:
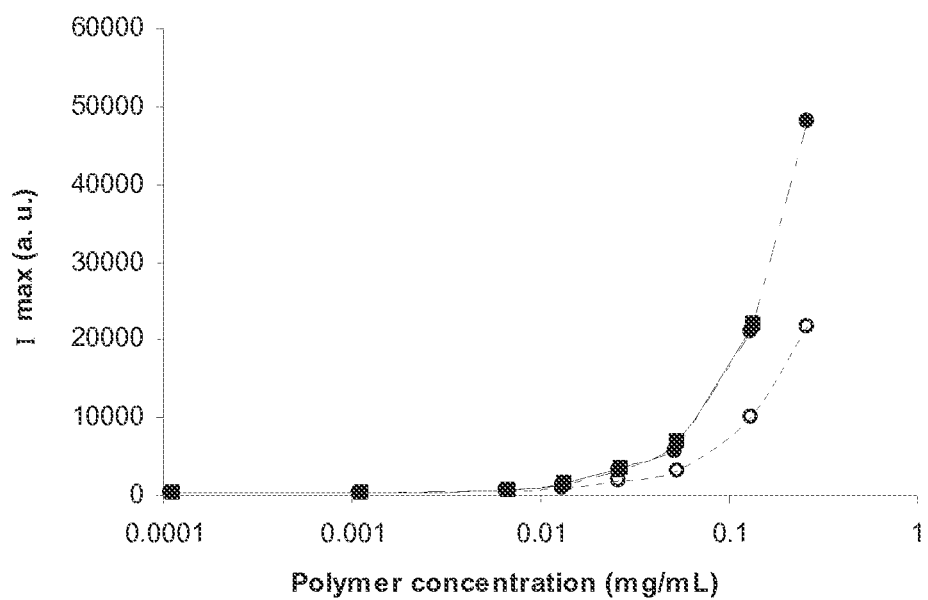

Critical micellar concentrations (CMC) were determined using Nile Red as a fluorescent probe. Based on the fact that this molecule is quasi insoluble in water and solubilizes itself only into the hydrophobic region of micelles, an intense fluorescence can be observed as soon as micelles are formed, as shown in FIG. 10B. Here the maximum fluorescence intensity is presented as a function of the polymer concentration. The CMC could be precisely determined at the inflection point of the plot of the maximum emission wavelength as a function of the polymer concentration (FIG. 19A.), a method developed by Coutinho et al. (2002). As expected, the CMC determined for MPEG2-PmHLA3 and MPEG2-PdiHLA3 was slightly lower with 8.5 and 8 mg/mL, respectively in comparison to the analog MPEG2-PLA3 with 10 mg/L, due to the increased hydrophobicity of the P(m/di)HLA3 segment. These low CMC values allow to envision the use of these novel micelles as drug carriers in very diluted conditions.

Figure 11:
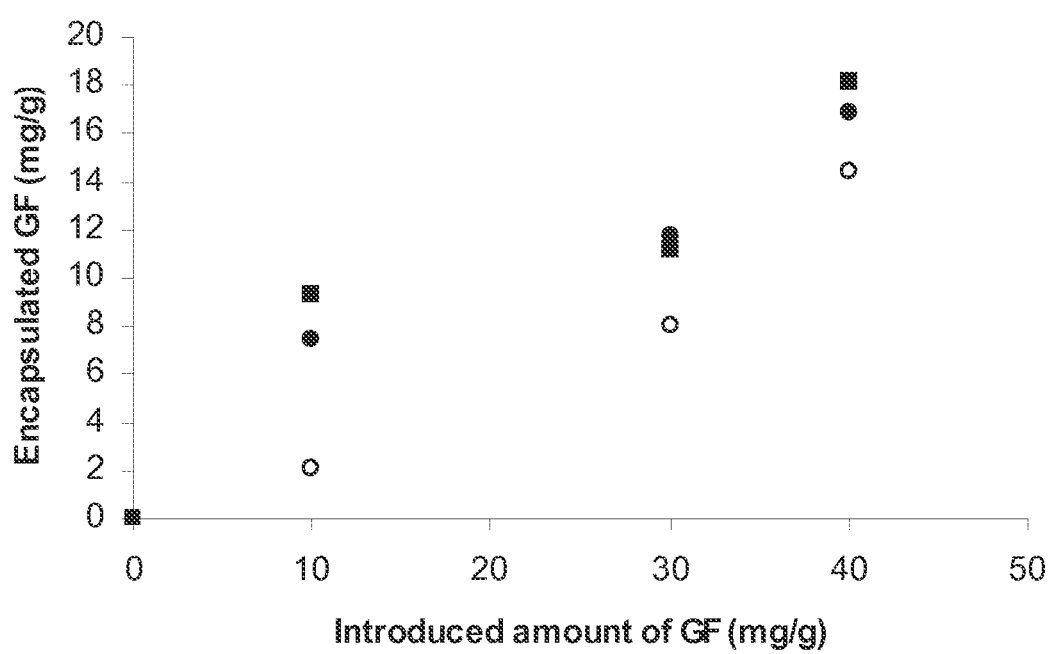
FIG. 11: Loading of micelles with griseofulvin (mg/g polymer) as a function of the griseofulvin introduced amount (mg/g polymer) for MPEG2-PLA3 (○), MPEG2-PmHLA3 (●) and MPEG2-PdiHLA3 (■).

The reinforced hydrophobic character of the micelle core of the hexyl-substituted PLA in comparison to standard PLA can especially be of interest for optimized hydrophobic drug loadings. For this purpose, the incorporation of griseofulvin (GF) in these novel micelles was investigated. The procedure to prepare the GF-loaded micelles was the same as for the blank ones, except that GF was dissolved with the copolymer in acetone prior to addition in the water phase. After removal of acetone, the non-entrapped GF was insoluble in water and easily eliminated by centrifugation. Whatever the amounts of GF used, the mean size was always comprised in the range of 30-80 nm. The amount of encapsulated GF in the different micelles was assessed by HPLC after destroying the micelles by solubilization of the copolymer in acetonitrile. As shown in FIG. 11, the levels of loaded GF were higher in the micelles with the more hydrophobic core, whatever the introduced amount of GF. A significant difference was observed between PLA-based micelles and PmHLA and PdiHLA-based ones. For the two latters, the levels of encapsulated GF were relatively similar.

This Example provides the synthesis and characterization of novel amphiphilic MPEG-PHLA di-block copolymers by ROP of the monohexyl-substituted lactide using a methoxy-terminated PEG as initiator and in the presence of $Sn(Oct)_2$ as a catalyst. Predictable molecular weights and narrow distributions were achieved. The physical properties of the copolymers were determined by DSC, showing the presence of amorphous and crystalline domains arising from both homopolymers. Micelles (~40-90 nm) were successfully prepared from these new copolymers. UV-visible experiments with Nile Red showed a reinforced hydrophobicity of the micelle core when increasing the density of hexyl groups on the polyester chain, with a shift observed in the maximum absorption wavelength and higher amounts of Nile Red incorporated. The CMC was very lower (8-8.5 mg/L) for the micelles based on the mono and di hexyl-substituted polylactide than that obtained for those based on the standard PLA (10 mg/mL), and allow to envision the use of these micelles as drug carriers in extremely diluted conditions. This reinforced hydrophobicity of the inner micelle core led to high hydrophobic drug loadings, as it was shown for the griseofulvin model drug. Finally, it is to point out that the copolymer composition and molecular weight can be easily tuned thanks to the flexibility of the ROP, depending on the final properties required for the material.

Example 5

Synthesis and Characterization of Novel Acrylated Star-Shaped Poly(Hexyl Substituted Lactides) for Obtention of Semi-Solid Biodegradable Networks Biodegradable PLA-based networks have recently received high attention due to their possible application as materials in key issues of tissue engineering and drug delivery (Barakat et al., 1996; Kelly et al., 2003). As for now, most of the biodegradable networks are based on acrylated star-shaped PLAs with further crosslinking (Robson et al., 1993; Helminen et al., 2001). The inventors describe here the possibility of tailoring the properties of such networks, based on the inventors' approach of the synthesis and ring-opening polymerization of new alkyl-substituted lactides, as already reported (Trimaille et al., 2004). Particularly, the inventors present here the synthesis and characterization of acrylated star-shaped poly(monohexyl-substituted lactides) leading to semi-solid low glass transition temperature networks.

The monohexyl-substituted lactide (mHLA), whose synthesis is described (Trimaille et al., 2005), was polymerized in the presence of 1,1,1-tris(hydroxymethyl)ethane (TE) and pentaerythritol (PE) as multifunctional alcohol initiators to achieve 3 arms and 4 arms star-shaped architectures, respectively. The FDA-approved $Sn(Oct)_2$ was used as a catalyst at a molar ratio catalyst-to-initiator of 0.25, and ROP were performed in convenient bulk conditions at 100° C. The results are presented in the Table 11. A first series of mHLA polymerizations was performed targeting a DP of 30 with TE (entry 2) and PE (entry 3). Conversions were nearly complete (95%) after 3 h reaction for both initiators, and predictable molecular weights and narrow polydispersities were obtained (Mw/Mn<1.20). As a reference, standard D,L-lactide was polymerized in the same conditions (except toluene was used as a solvent) with TE and the conversion was total (entry 1). The slightly higher polydispersity obtained (Mw/Mn=1.26) compared to that of mHLA (1.16) can be attributed to the beginning of side transesterification reactions at complete conversion (100%, Table 11).

TABLE 11

Characteristics of the star shaped poly(monohexyl-substituted lactides)

| entry | Monomer | Initiator | C/I | Temp (° C.) | Time (h) | Conv. (%) | DP Targeted | DP Meas.[b] | $M_n$ (g/mol) | $M_w/M_n$ |
|---|---|---|---|---|---|---|---|---|---|---|
| 1 | D,L-lac | TE | 0.25 | 100[a] | 3 | ~100 | 30 | 29 | 5090 | 1.26 |
| 2 | mHLA | TE | 0.25 | 100 | 3 | 95 | 30 | 31 | 5810 | 1.16 |
| 3 | mHLA | PE | 0.25 | 100 | 3 | 95 | 30 | n.d.[c] | 6500 | 1.19 |
| 4 | mHLA | TE | 0.25 | 100 | 5 | 85 | 60 | 38 | 7700 | 1.24 |
| 5 | mHLA | TE | 0.25 | 100 | 5 | 60 | 120 | 39 | 6950 | 1.31 |
| 6 | mHLA | PE | 0.25 | 100 | 5 | 85 | 60 | n.d.[c] | 6880[a] | 1.49 |
| 7 | mHLA | PE | 0.25 | 100 | 5 | 72 | 120 | n.d.[c] | 7770[a] | 1.35 |

[a]using toluene as solvent
[b]by $^1$H NMR
[c]not determined due to overlapping

$^1$H NMR was used to confirm the structure the 3-arms and 4-arms star-shaped PmHLA (CDCl$_3$, 300 MHz) of DP 30, as shown below.

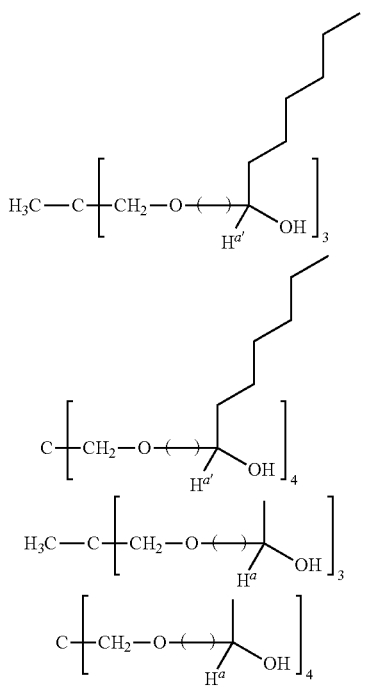

The $^1$H NMR spectra of the PmHLA of targeted DP 30 initiated with TE and PE are presented in FIGS. 23A-B, respectively. All the peaks were identified, particularly the C HOH end groups and CH$_2$ singlets from the TE and PE initiators showing that the latters were effective as initiating the polymerization and demonstrating the star-shaped architecture of the polymer. Nevertheless, for PE-initiated polymerizations, the overlapping of these peaks did not allow the calculation of the DP (from CH$_2$ and methine protons integrals). For TE-initiated polymerizations, the calculation was possible and the experimental DP obtained was really close to the expected one (Table 11). The CH$_3$ singlet (at about 1 ppm) from this initiator was also clearly identified.

The control of the polymerization of mHLA with TE and PE was then further investigated by targeting higher DPs of 60 and 120 (Table 11, entries 4-7), with a polymerization time of 5 hours. A loss in the polymerization control was observed, as evidenced by the lower MW and DP than that expected and higher polydispersities. Investigating in further details the GPC chromatograms of the polymers initiated by TE and PE, nice narrow and symmetric peaks were observed for a targeted DP of 30, whereas peaks with a slight shoulder were observed for higher targeted DPs, explaining a higher polydispersity and a lower MW than expected. However, this phenomenon was less marked for the polymerizations initiated with TE than for those initiated with PE, with a "shoulder" effect observed only for the highest targeted DP 120 (for PE, it was observed for both DPs 60 and 120). This can be attributed to the fact that TE alcohol was good soluble in the melting monomer during the polymerization whereas PE was insoluble in either melts or solvents as toluene and THF. Initiation with the latter alcohol was thus less efficient, and as a result all the chains can not be initiated and propagate at the same time, as required for a "living" polymerization process.

With a view to obtain biodegradable networks from PmHLA, the alcohol endgroups of the polymer were then acrylated through the use of acryloyl chloride, as described in Scheme 6. Star-shaped PLA was also tested as a reference. The acrylation yield was calculated by $^1$H NMR after purification (by precipitation in MeOH) comparing the peak integrals of vinyl protons with the one of the CH$_2$ originating from the initiator. $^1$H NMR was obtained for the purified star-shaped PHmLA before and after the acrylation in the presence of a large excess of acryloyl chloride (~75 eq. per alcohol endgroup of the polymer). Acrylation yield was very good (>95%), and the values of molecular weights and polydispersity were similar to those obtained before acrylation (Table 12).

Scheme 6: Acrylation reaction of the 3-arms star-shaped PmHLA

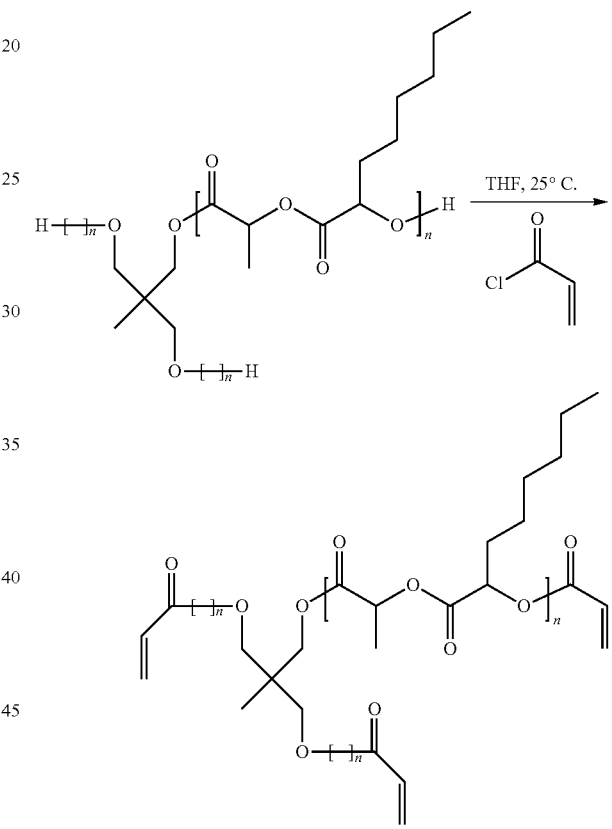

TABLE 12

Characteristics of the acrylated star-shaped (3 arms) PmHLA and PLA polymers.

|  | Acrylation yield (%) | M$_n$ (g/mol) | M$_w$/M$_n$ |
|---|---|---|---|
| Acryl st-PLA | 98 | 4810 | 1.17 |
| Acryl. st-PmHLA | 95 | 6290 | 1.09 |

Crosslinking of the obtained polymer was then performed using the conventional AIBN initiator (10 mol % per double bonds of the polymer). After 1 h reaction in THF at 70° C., the network was formed, as seen from the solid mixture insoluble in the THF and swollen by this solvent. The glass transition temperature of the obtained network (−20.5° C.) was significantly different of those of the st-PmHLA before or after acrylation (−13.7 and −14.2° C.), demonstrating the novel properties of the obtained network compared to the star-shaped polymer. This work shows the possibility to easily obtain biodegradable semi-solid networks.

Monohexyl-substituted lactide was synthesized as previously described (Trimaille et al., 2005). D,L-lactide from Purac Biochem (The Netherlands) was delivered under vacuum and directly transferred into a glove-box for storage. Tin(II) 2-ethylhexanoate ($Sn(Oct)_2$), pentaerythritol (PE) and 1,1,1-tris(hydroxymethyl)ethane (TE) were purchased from Aldrich (Buchs, Switzerland) and acryloyl chloride and $\alpha,\alpha'$-azoisobutyronitrile (AIBN) were from Fluka (Buchs, Switzerland). PE and TE were carefully dried over vacuum before use. Solvents were dried by standard methods and distilled prior to use.

Star-Shaped P(mH)LA Synthesis.

Polymerizations were typically run with 1 g of monomer in bulk (monohexyl-substituted lactide) or in toluene (D,L-lactide) in the presence of $Sn(Oct)_2$ as catalyst and PE or TE as multifunctional initiator (molar ratio $Sn(Oct)_2$/initiator=0.25). A reaction flask containing a stirbar was fitted with a septum, flamed under vacuum, and placed into a glove-box, where the monomer was filled in. In a typical procedure (for a targeted degree of polymerization [DP] of 30), 1.0 g monohexyl-substituted lactide (9.34 mmol) with 27.7 mg TE was heated for melting, and 120 μL $Sn(Oct)_2$ stock solution (0.20 g/mL in dry THF) were added under argon atmosphere, and the mixture was heated to 100° C. At the desired reaction time, ~100 mg of mixture was taken out and the reaction was quenched by adding non dry THF, followed by precipitation in cold MeOH and drying at 40° C. under vacuum.

Acrylated Star-Shaped P(mH)LA.

The rest of the reaction mixture was quenched by adding a large excess of acryloyl chloride with respect to the alcohol end groups of the polymer (3 mL) in dry THF. The solution was stirred at room temperature for 16 h, and 1 mL water was added to hydrolyze the remaining acryloyl chloride. The polymers were precipitated in methanol.

Crosslinking of the Acrylated Star-Shaped P(mH)LA.

The acrylated polymer was dissolved in THF with AIBN (10 mol % per double bonds). The solution was degassed with argon for 30 minutes and then heated to 70° C. The network was formed after 1 h-1 h30 (insolubility in THF).

Polymer Characterization.

Polymerization conversions and DP were determined by $^1$H NMR analysis, and molecular weights and polydispersities by Gel Permeation Chromatography (GPC). The $^1$H NMR spectra were recorded in deuterated chloroform with a Bruker spectrometer (300 MHz). GPC was carried out on a Waters chromatographer, mounted with Styragel HR 1-4 columns (Waters) and connected to a Waters 410 differential refractometer. THF was the continuous phase and polystyrenes of known molecular weights: 500, 2630, 5970, 9100, 37900, 96400 g/mol (Tosoh Corporation) were used as calibration standards.

Thermal analysis of the polymers was performed with a differential scanning calorimeter (SSC/5200, Seiko Instruments). Heating was performed at a flow rate of 10° C./min under nitrogen and the temperature was calibrated with an indium standard.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,792,451
U.S. Pat. No. 5,399,363
U.S. Pat. No. 5,466,468
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,641,515
U.S. Pat. No. 5,725,871
U.S. Pat. No. 5,756,353
U.S. Pat. No. 5,780,045
U.S. Pat. No. 5,804,212
U.S. Pat. No. 6,126,919
U.S. Pat. No. 6,469,133
U.S. Pat. No. 6,613,308
U.S. Pat. No. 6,753,514
Amsden et al., *Biomacromolecules*, 5:637, 2004.
Barakat et al., *J. Polym. Sci*. Part A, 37:2401-2411, 1996.
Bolte et al., *Acta Crystall. Sec. C*, C50:1717-1721, 1994.
Chrisholm and Delbridge, *J. Chem.*, 27:1167-1176, 2003.
Davis et al., *Biomaterials*, 24(14):2485-2495, 2003.
Deane and Hammond, *J. Dairy Sci.*, 43:1421-1429, 1960.
Dechy-Cabaret et al., *Chem., Rev.*, 104:6147-6176, 2004.
Degee et al., *J. Polym. Sci. A, Polym. Chem.*, 37:2413-2420, 1999.
Drumright et al., *Advanced Materials*, 12:1941-1846, 2000.
Food Drug Admin. Food Additives, Ref. Regist., 40(121)C, 1975.
Fox and Loshaek, *J. Appl. Phys.*, 26:1080, 1955.
Grizzi et al., *Biomaterials*, 16:305-311, 1995.
Gurny et al., *Macromolecules*, 32:301-307, 1999.
Hakkarainen et al., *Polym. Deg. Stab.*, 52:283-291, 1996.
Hall and Hill, *J. Soc. Cosmet. Chem.*, 37:397-407, 1986.
Hatefi and Amsden, *J. Control Rel.*, 80:9, 2002.
Helminen et al., *Polymer*, 42(8):3345-3353, 2001.
Hwang et al., *Crit. Rev. Ther. Drug Carrier Syst.*, 15(3):243-284, 1998.
Hyon et al., *Biomaterials.*, 18:1503-1508, 1997.
Jamshidi et al., *Polymer*, 29:2229-2234, 1988.
Jiang et al., *Adv. Drug Deliv. Rev.*, 57:391-410, 2005.
Kazunori et al., *Advanced Drug Deliv. Revs.*, 47(1):113-131, 2001.
Kowalski et al., *Macromol. Rapid Commun.*, 19:567-572, 1998.
Kricheldorf et al., *Macromolcules*, 33:702-709, 2000.
Kricheldorf et al., *Polymer*, 36:1253-1259, 1995.
Lin et al., *Pharm. Res.*, 20:668-673, 2003.
Liu and Ma, *Ann. Biomed. Eng.*, 32:477-486, 2004.
Lou et al., *Macromol. Rapid. Commun.*, 24:161-172, 2003.

Mathiowitz et al., *Nature*, 386(6623):410-414, 1997.
McGuinness et al., *J. Polym. Sci. A Polym. Chem.*, 41:3798-3803, 2003.
Merkli et al., *J. Control Rel.*, 29:105-112, 1994.
Möller et al., *J. Polym. Sci. A Polym. Chem.*, 38:2067-2074, 2000.
Möller et al., *J. Polym. Sci. A Polym. Chem.*, 39:3529-3538, 2001.
Mu and Feng, *J. Control. Release*, 86:33-48, 2003.
Mullen et al., *J. Polym. Sci. A Polym. Chem.*, 41:1978-1991, 2003.
Myers et al., *J. Polym. Sci. A Polym. Chem.*, 40:844-851, 2002.
Nederberg et al., *Chem. Int. Ed*, 40:2712-2715, 2001.
Ouchi et al., *J. Polym. Sci. A Polym. Chem.*, 40:1218-1255, 2002.
Penning et al., *Polymer*, 34:942-951, 1993.
Porter and Johnson, *Chem. Rev.*, 66:1, 1966.
*Remington's Pharmaceutical Sciences*, 15th ed., pages 1035-1038 and 1570-1580, Mack Publishing Company, Easton, Pa., 1980.
*Remington's Pharmaceutical Sciences*, 18th Ed. Mack Printing Company, 1289-1329, 1990.
Riley et al., *Langmuir*, 17(11):3168-3174, 2001.
Robson et al., *Polymer*, 34(20):4365-4372, 1993.
Ryner et al., *Macromolecules*, 34:7281-7287, 2001.
Schollkopf et al., *Chem.*, 91:329-330, 1979.
Schwach et al., *J. Polym. Sci. A Polym. Chem.*, 35:3431-3440, 1997.
Schwach-Abdellaoui et al., *Proc. Intern Symp. Control Rel. Bioact. Mater,* 28:3065-306, 2001.
Schwach-Abdellaoui et al., *Biomaterials*, 22:1659-1666, 2001.
Shiosaki and Rapoport, *J. Org. Chem.*, 50:1229-1239, 1985.
Shirahama et al., *J. Polym. Sci. A Polym. Chem.*, 40:302-316, 2002.
Simmons and Baker, *Biomacromolecules*, 2:658-663, 2001.
Stock and Mayer, *Long Ter Eff. Med. Implants*, 11:249-260, 2001.
Storey and Sherman, *Macromolecules*, 35:1504-1512, 2002.
Storey et al., *J. Polym. Sci. A Polym. Chem.*, 41:1296-1305, 2003.
Takenaga et al., *J. Control Release,* 52(1-2):81-87, 1998.
Trimaille et al., *J. Polym. Sci. A Polym. Chem.*, 42:4379-4391, 2004.
Traimaille et al., *Chimia*, 59:348-352, 2005.
Tsuji et al., *Macromolecules*, 24:2719-2724, 1991.
Uhrich et al., *Chem. Rev.,* 99:3181-3198, 1999.
Vert et al., In: *Macromolecular biomaterials*, Hastings et al. (Eds.), CRS Press, Fl, 119, 1984.
Vink et al., *Polym. Deg. Stab.,* 80:403-419, 2003.
Yasugi et al., *J. Controlled Release,* 62(1-2):89-100, 1999.
Ye et al., *React. Funct. Polym.,* 32:161-168, 1997.
Yin and Baker, *Macromolecules,* 32:7711-7718, 1999.
Yoo and Park, *J. Controller Release,* 70(1-2)63-70, 2001.

The invention claimed is:

1. A pharmaceutical composition comprising a polylactide and a drug, wherein the polylactide has the structure:

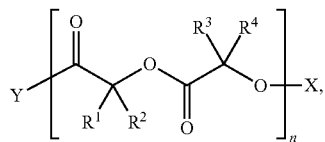

wherein:
  $R^1$, $R^2$, $R^3$, and $R^4$ are each independently chosen from the group consisting of unsubstituted $C_{1-20}$alkyl, hydrogen, $C_{2-20}$alkenyl, and —$(CH_2)_y$—$(C_6H_5)$, wherein y=1-20;
  n is 2 to 100;
  X is hydrogen or —C(O)—CH═$CH_2$;
  at least one of $R^1$, $R^2$, $R^3$, and $R^4$ is $C_{4-20}$ unsubstituted alkyl, $C_{2-20}$ alkenyl, or —$(CH_2)_y$—$(C_6H_5)$, wherein y=1-20;
  Y is —O—$(CH_2$—$CH_2$—$O)_p$—$CH_3$, wherein p is 1 to 700;
  and wherein the polylactide has a $T_g$ value of less than 15° C.

2. The composition of claim 1, wherein the pharmaceutical composition is formulated for parenteral, oral, topical, buccal, rectal, sublingual, intravenous, intradermal, transdermal, intrathecal, intraarterial, intraperitoneal, intranasal, mucosal, intravaginal, intrarectal, intramuscular, inhalation, injection, infusion, subcutaneous, or topical administration.

3. The composition of claim 2, wherein the pharmaceutical composition is formulated for buccal, mucosal, intravaginal, or intrarectal administration.

4. The composition of claim 2, wherein the pharmaceutical composition is formulated for topical administration.

5. The composition of claim 4, wherein the pharmaceutical composition is formulated as an ointment, paste, or cream.

6. The composition of claim 2, wherein the pharmaceutical composition is formulated for oral administration.

7. The composition of claim 2, wherein the pharmaceutical composition is formulated as a powder or a tablet.

8. The composition of claim 1, wherein the pharmaceutical composition is formulated as eye drops.

9. The composition of claim 1, wherein the pharmaceutical composition is formulated for inhalation or other aerosol delivery.

10. The composition of claim 1, wherein n is 2 to 75.

11. The composition of claim 10, wherein n is 2 to 50.

12. The composition of claim 11, wherein p is 1 to 250.

13. The composition of claim 10, wherein $R^1$ and $R^3$ are hydrogen; and $R^2$ and $R^4$ are $C_{4-20}$ alkyl.

14. The composition of claim 13, wherein $R^2$ and $R^4$ are —$(CH_2)_m$—$CH_3$, wherein m is from 3-19.

15. The composition of claim 14, wherein m is from 3 to 12.

16. The composition of claim 1, wherein $R^1$ and $R^3$ are hydrogen; and wherein $R^2$ and $R^4$ are —$(CH_2)_m$—$CH_3$ or —$CH_3$, wherein m=3-12.

17. The composition of claim 16, wherein m=3-9.

18. The composition of claim 1, wherein m=4-6.

19. The composition of claim 1, wherein m=5.

20. The composition of claim 11, wherein n is 2 to 25.

21. The composition of claim 1, wherein $R^1$ and $R^3$ are hydrogen; and wherein $R^2$ and $R^4$ are —$(CH_2)_m$—$CH_3$, wherein m=3-12.

22. The composition of claim 1, wherein $R^1$ and $R^3$ are hydrogen; and wherein $R^2$ and $R^4$ are —$CH_2$—$(C_6H_5)$ or —$CH_3$.

23. The composition of claim 1, wherein $R^1$ and $R^3$ are hydrogen; and wherein $R^2$ and $R^4$ are —$CH_2$—$(C_6H_5)$.

24. The composition of claim 1, wherein $R^1$ and $R^3$ are hydrogen; and wherein $R^2$ and $R^4$ are —$CH(CH_3)_2$ or —$CH_3$.

25. The composition of claim 1, wherein $R^1$ and $R^3$ are hydrogen; and wherein $R^2$ and $R^4$ are —$(CH_2)_3$—$CH_3$ or —$CH_3$.

26. The composition of claim 1, wherein $R^1$ and $R^3$ are hydrogen; and wherein $R^2$ and $R^4$ are —$(CH_2)_5$—$CH_3$ or —$CH_3$.

27. The composition of claim 26, wherein the pharmaceutical composition is formulated for topical administration, rectal administration, intranasal administration, oral administration, or the composition is formulated as eye drops.

28. The composition of claim 27, wherein $R^1$ and $R^3$ are hydrogen; and wherein $R^2$ and $R^4$ are —$(CH_2)_5$—$CH_3$ or —$CH_3$.

29. The composition of claim 27, wherein $R^1$ and $R^3$ are hydrogen; and wherein $R^2$ and $R^4$ are —$(CH_2)_5$—$CH_3$.

30. The composition of claim 29, wherein the composition is formulated for topical administration.

31. The composition of claim 29, wherein the composition is formulated as eye drops.

* * * * *